(12) United States Patent
Ma et al.

(10) Patent No.: US 11,192,835 B2
(45) Date of Patent: Dec. 7, 2021

(54) POLYOXOMETALATES COMPRISING NOBLE METALS AND CARBOXYLATE-BASED CAPPING GROUPS AND METAL-CLUSTERS THEREOF

(71) Applicant: ExxonMobil Chemical Patents Inc., Baytown, TX (US)

(72) Inventors: Tian Ma, Bremen (DE); Peng Yang, Changsha (CN); Wassim W. Ayass, Berlin (DE); Zhengguo Lin, Beijing (CN); Ulrich Kortz, Bremen (DE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 38 days.

(21) Appl. No.: 16/608,389

(22) PCT Filed: Apr. 17, 2018

(86) PCT No.: PCT/EP2018/059793
§ 371 (c)(1),
(2) Date: Oct. 25, 2019

(87) PCT Pub. No.: WO2018/202420
PCT Pub. Date: Nov. 8, 2018

(65) Prior Publication Data
US 2020/0216371 A1    Jul. 9, 2020

(30) Foreign Application Priority Data

May 5, 2017   (EP) .................................... 17169754

(51) Int. Cl.
*C07C 5/10*    (2006.01)
*B01J 29/035*   (2006.01)
(Continued)

(52) U.S. Cl.
CPC ............. *C07C 5/10* (2013.01); *B01J 29/0354* (2013.01); *B01J 35/0013* (2013.01);
(Continued)

(58) Field of Classification Search
CPC .............................. C07C 5/10; B01J 29/0354
(Continued)

(56) References Cited

U.S. PATENT DOCUMENTS

| 4,864,041 A | 9/1989 | Hill |
| 2005/0112055 A1 | 5/2005 | Shannon et al. |

(Continued)

FOREIGN PATENT DOCUMENTS

| WO | 2007/099449 A | 9/2007 |
| WO | 2007/105052 A | 9/2007 |

(Continued)

OTHER PUBLICATIONS

Abbet et al., "Acetylene Cyclotrimerization on Supported Size-Selected $Pd_n$ Clusters ($1 \leq n \leq 30$) One Atom is Enough!", J. am. Chem. Soc. 2000, vol. 122, pp. 3453-3457.

(Continued)

*Primary Examiner* — Douglas B Call

(57) ABSTRACT

The invention relates to polyoxometalates represented by the formula $(A_n)^{m+}[M'M_{12}O_y(RCOO)_zH_q]^{m-}$ or solvates thereof, corresponding supported polyoxometalates, and processes for their preparation, as well as corresponding metal clusters, optionally in the form of a dispersion in a liquid carrier medium or immobilized on a solid support, and processes for their preparation, as well as their use in reductive conversion of organic substrate.

12 Claims, 8 Drawing Sheets

Figure 1:
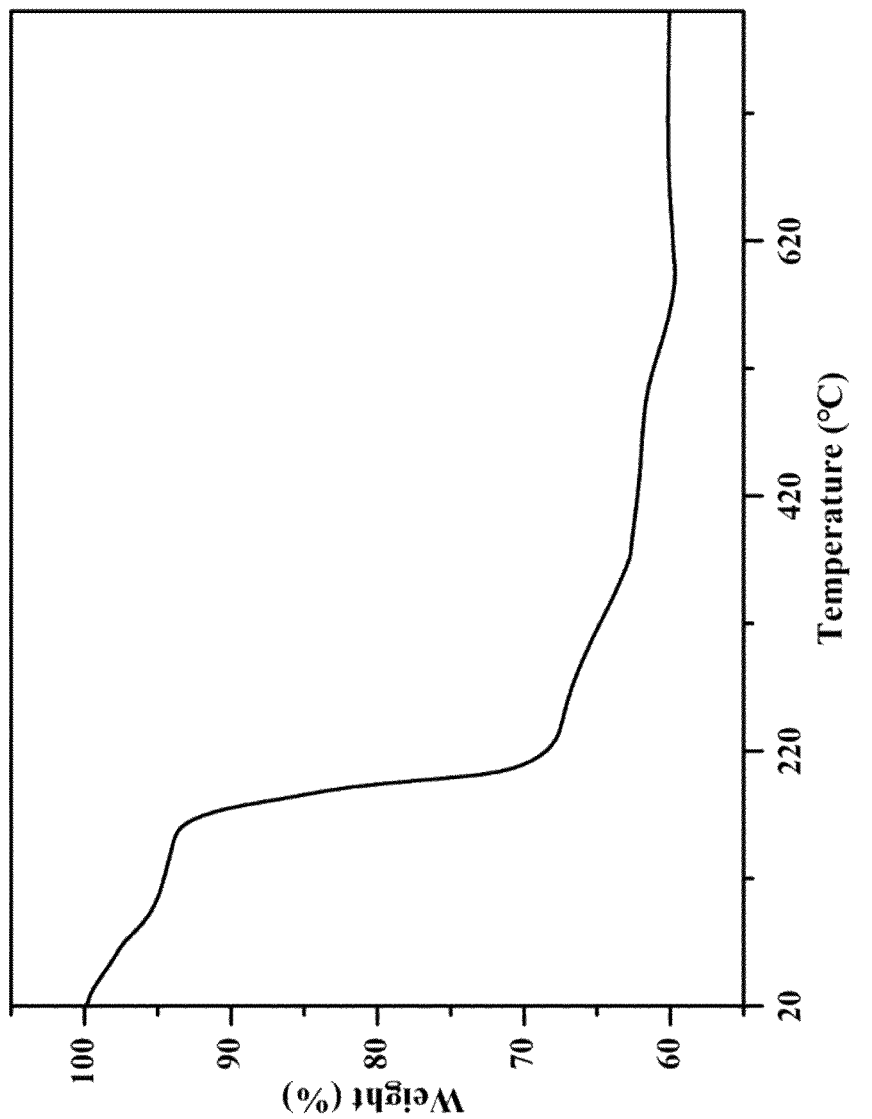

(51) Int. Cl.
  B01J 35/00      (2006.01)
  B01J 37/02      (2006.01)
  B01J 37/04      (2006.01)
  B01J 37/18      (2006.01)
(52) U.S. Cl.
  CPC .......... B01J 37/0219 (2013.01); B01J 37/04 (2013.01); B01J 37/18 (2013.01); *B01J 2231/646* (2013.01); *B01J 2531/0216* (2013.01); *B01J 2531/824* (2013.01); *C07C 2531/22* (2013.01); *C07C 2601/14* (2017.05)
(58) Field of Classification Search
  USPC .......................................................... 502/306
  See application file for complete search history.

(56) References Cited

U.S. PATENT DOCUMENTS

| | | | |
|---|---|---|---|
| 2006/0199986 | A1 | 9/2006 | McCarthy et al. |
| 2009/0216052 | A1 | 8/2009 | Chubarova et al. |
| 2019/0030517 | A1 | 1/2019 | Kortz et al. |
| 2019/0091663 | A1* | 3/2019 | Kortz ...................... B01J 21/08 |
| 2020/0070131 | A1 | 3/2020 | Ma et al. |

FOREIGN PATENT DOCUMENTS

| | | | |
|---|---|---|---|
| WO | 2007/139616 | A | 12/2007 |
| WO | 2007/142727 | A | 12/2007 |
| WO | 2007/142729 | A | 12/2007 |
| WO | 2008/089065 | A | 7/2008 |
| WO | 2008/118619 | A | 10/2008 |
| WO | 2009/155185 | A | 12/2009 |
| WO | 2010/021600 | A | 2/2010 |

OTHER PUBLICATIONS

Barsukova et al., "Polyoxopalladates Encapsulating Yttrium and Lanthanide Ions, $[X^{III}Pd^{II}_{12}(AsPH)_8O_{32}]^{5-}$ (X=Y, Pr, Nd, Sm, Eu, Gd, Tb, Dy, Ho, Er, Tm, Yb, Lu)", Chem. Eur. J. 2010, vol. 16, pp. 9076-9085.

Barsukova-Stuckart et al., "Synthesis and Characterization of the Dicopper(II)-Containing 22-Palladate(II)$[Cu^{II}_2Pd^{II}_{22}P^V_{12}O_{60}(OH)_8]^{20-}$", Angew. Chem. Int. Ed. 2 011, vol. 50, pp. 2639-2642.

Barsukova-Stuckart et al., "3d Metal Ions in Highly Unusual Eight-Coordination: The Phosphate-Capped Dodecapalladate(II) Nanocube", Chem. Eur. J. 2012, vol. 18, pp. 6167-6171.

Cameron et al., "Self-assembly and structural transformations of high-nuclearity palladium-rich polyoxometalates", Inorg. Chem. Front., 2014, vol. 1, pp. 178-185.

Chubarova et al., "Self-Assembly of a Heteropolyoxopalladate Nanocube $[Pd^{II}_{13}As^V_8O_{34}(OH)_6]^{8-}$", Angew. Chem. Int. Ed. 2008, vol. 47, pp. 9542-9546.

Izarova et al., "Heteropoly-13-Palladates(II) $[Pd^{II}_{13}(As^VPh)_8O_{32}]^{6-}$ and $[Pd^{II}_{13}Se^{IV}_8O_{32}]^{6-}$", Inorg. Chem. 2009, vol. 48, pp. 7504-7506.

Izarova et al., "Self-assembly of star-shaped heteropoly-15-palladate(II)", Dalton Transactions The International Journal for Inorganic, Organometallic and Bioinorganic Chemistry, No. 43, 2009, pp. 9385-9387.

Izarova et al., "A Noble-Metalate Bowl: The Polyoxo-6-vanado(V)-7-palladate(II) $[Pd_7V_6O_{24}(OH_2]^{6-}$", Angew. Chem. Int. Ed. 2010, vol. 49, pp. 7807-7811.

Izarova et al., "Noble Metals in Polyoxometalates", Angew. Chem. Int. Ed. 2012, vol. 51, pp. 9492-9510.

Izarova et al., "The Mixed Gold-Palladium Polyoxo-Noble-Metalate $[NaAu^{III}_4Pd^{II}_8O_8(AsO_4)_8]^{11-}$", Chem. Eur. J. 2014, vol. 20, pp. 8556-8560.

Lang et al., "Size and charge effect of guest cations in the formation of polyoxopalladates: a theoretical and experimental study", Chem. Sci., 2017, vol. 8, pp. 7862-7872.

Lin et al., "Chiral Dodecanuclear Palladium(II) Thio Cluster: Synthesis, Structure, and Formation Mechanism Explored by ESI-MS and DFT Calculations", Inorg. Chem. 2016, vol. 55, No. 16, pp. 7811-7813.

Liu et al., "Defective Graphene Supported MPd42 (M=Fe, Co, Ni, Cu, Zn, Pd) Nanoparticles as Potential Oxygen Reduction Electrocatalysts: A First-Principles Study", J. Phys. Chem. C 2013, vol. 117, pp. 1350-1357.

Nefedov et al., "The Role Water Molecules in Formation of Heterometallic Palladium Acetate Complexes with Cerium and Neodymium", Russian Journal of Inorganic Chemistry, 2011, vol. 56, No. 3, pp. 357-374.

Nefedov et al., "Unusual heterobimetallic palladium(II)-cerium(III acetate complexes", Inorg. Chem. C., vol. 14, 2011, pp. 554-557.

Okumura et al., "Energy-Dispersive XAFS Studies on the Spontaneous Dispersion of PdO and the Formation of Stable Pd Clusters in Zeolites", J. Phys. Chem. B 2004, vol. 108, pp. 6250-6255.

Posada-Borbon et al., "Cluster Size Effects in Ethylene Hydrogenation over Palladium", J. Phys. Chem. C, 2017, vol. 121, No. 20, pp. 10870-10875.

Putaj et al., "Polyoxometalates containing late transition and noble metal atoms", Coord. Chem. Rev. 2011, vol. 255, pp. 1642-1685.

Shibayama et al., "Effect of metal oxide supports on catalytic performance of supported ultrafine metal catalysts: density functional and tight-binding quantum chemical study", Database CA [Online] Chemical Abstracts Service, XP-002775950, Abstract, pp. 1-3.

Vogel et al., "In Situ X-Ray Analysis of CO- and $CH_3OH$-Induced Growth of Pd Particles Encaged in Zeolite Y", Studies in Surface Science and Catalysis, vol. 75, 1993, pp. 1641-1644.

Yang et al., "Alkaline Earth Guests in Polyoxopalladate Chemistry: From Nanocube to Nanostar via an Open-Shell Structure", Angew. Chem. Int. Ed. 2014, vol. 53, pp. 11974-11978.

Barsukova-Stuckart et al., "Polyoxopalladates Encapsulating 8-Coordinated Metal Ions, $[MO_8Pd^{II}_{12}L_8]^{n-}$ (M=$Sc^{3+}$, $Mn^{2+}$, $Fe^{3+}$, $Co^{2+}$, $Cu^{2+}$, $Zn^{2+}$, $Lu^{3+}$; L=$PhAsO_3^{2-}$, $PhPO_3^{2-}$, $SeO_3^{2-}$)", Inorg. Chem. 2012, vol. 51, pp. 13214-13228.

* cited by examiner

POLYOXOMETALATES COMPRISING NOBLE METALS AND CARBOXYLATE-BASED CAPPING GROUPS AND METAL-CLUSTERS THEREOF

CROSS REFERENCE TO RELATED APPLICATIONS

This application is a National Stage Application of International Application No. PCT/EP2018/059793, filed Apr. 17, 2018, which claims priority to and the benefit of European Patent Application Serial No. 17169754.3, filed May 5, 2017, which are incorporated herein by reference in their entireties.

FIELD OF THE INVENTION

This invention relates to new polyoxometalates (POMs, also known as polyanions) and metal clusters. Furthermore, this invention relates to processes for the preparation of said new POMs and metal clusters and to their use in catalytic reduction reactions with organic molecules.

BACKGROUND OF THE INVENTION

POMs are a unique class of inorganic metal-oxygen clusters. They consist of a polyhedral cage structure or framework bearing a negative charge which is balanced by cations that are usually external to the cage, and may also contain internally or externally located heteroatom(s) or guest atom(s). The framework of POMs comprises a plurality of metal atoms, which can be the same or different, bonded to oxygen atoms. In the plurality of known POMs, the framework metals are dominated by a few elements including transition metals from Group 5 and Group 6 in their high oxidation states, e.g., tungsten (VI), molybdenum (VI), vanadium (V), niobium (V) and tantalum (V).

The first example in the POM family is the so-called Keggin anion $[XM_{12}O_{40}]^{n-}$ with X being a heteroatom selected from a variety of elements, e.g., P, and M being a Group 5 or Group 6 metal such as Mo or W. These anions consist of an assembly of corner- and edge-shared $MO_6$ octahedra of the metals of Groups 5 or 6 around a central $XO_4$ tetrahedron.

There have been increasing efforts towards the modification of POMs with various organic and/or transition metal complex moieties with the aim of generating new catalyst systems as well as functional materials with interesting optical, electronic, magnetic and medicinal properties. In particular, transition metal-substituted POMs (TMSPs) have attracted continuously growing attention as they can be rationally modified on the molecular level including size, shape, charge density, acidity, redox states, stability, solubility etc.

For example, U.S. Pat. No. 4,864,041 in general demonstrates the potential of POMs as catalysts for the oxidation of organic compounds. A variety of different POMs with different metal species was investigated, including those with W, Mo, V, Cu, Mn, Fe, Fe and Co.

WO 2010/021600 A1 discloses a method for preparing POMs and reducing them. Thus, for example metallic nanoparticles can be derived. Specifically W-based POMs are discussed.

To date many 3d transition metal-containing POMs are known, but still only a minority of POMs contains 4d and 5d metals. However, the introduction of 4d and 5d metals, especially of late 4d and 5d metals, in a POM would be of fundamental interest en route to new, more efficient and more selective catalysts. Especially Rh, Ir, Pd, Pt, Ag and/or Au-containing POMs would be of high interest, because they are thermally and oxidatively stable and possess highly attractive catalytic properties.

Two reviews on POMs containing late transition metals and noble metals (Coord. Chem. Rev. 2011, 255, 1642-1685 and Angew. Chem. Int. Ed. 2012, 51, 9492-9510) reveal that, although there is a noticeable development in this area in recent years and decades, the POMs containing noble metals are almost exclusively still based on early transition metals, including Group 5 and 6 metals. Very few of these POMs are solely based on noble metals. In many cases the noble metals are incorporated in structural frameworks primarily composed of early transition metals, including Group 5 and 6 metals.

For example, Kortz and coworkers have found $[Pd_7V_6O_{24}(OH)_2]^{6-}$ containing compounds being stable in the solid state and after redissolution when exposed to air and light (Angew. Chem. Int. Ed. 2010, 49, 7807-7811).

For other POMs the proportion of noble metal atoms, based on the overall metal content of the POM framework is even far below 50%. For example, Cronin and coworkers found three Pd-containing POMs $K_{28}[H_{12}Pd_{10}Se_{10}W_{52}O_{206}]$, $K_{26}[H_{14}Pd_{10}Se_{10}W_{52}O_{206}]$ and $Na_{40}[Pd_6Te_{19}W_{42}O_{190}]$ demonstrating the structural complexity of some of the late transition metal-containing POMs (Inorg. Chem. Front. 2014, 1, 178-185).

WO 2007/142729 A1 discloses a class of Pd and W as well as Pt and W-based POMs and mixtures thereof with the general formula $[M_y(H_2O)_{(p\cdot y)}X_2W_{22}O_{74}(OH)_2]^{m-}$ with M being Pd, Pt, and mixtures thereof, y being 1 to 4, p being the number of water molecules bound to one M and being 3 to 5 and X being Sb, Bi, As, Se and Te. Protocols for the preparation of these POMs were provided. Furthermore, the POMs were found to be useful as catalysts.

WO 2008/089065 A1 discloses a class of W-based POMs including late transition metals with the formula $[M_y(H_2O)_pX_zZ_2W_{18}O_{66}]^{m-}$ with M being Cu, Zn, Pd and Pt, X being selected from the group of halides and Z being Sb, Bi, As, Se and Te. The POMs prepared are useful as catalysts.

WO 2007/142727 A1 discloses a class of transition metal-based POMs including W having the formula $[M_4(H_2O)_{10}(XW_9O_{33})_2]^{m-}$ with M being a transition metal and X being selected from As, Sb, Bi, Se and Te. These POMs are particularly useful as catalysts featuring high levels of conversion in selective alkane oxidation.

WO 2008/118619 A1 discloses another class of transition metal-based POMs including W which is illustrated by the general formula $[H_qM_{16}X_8W_{48}O_{184}(HO)_{32}]^{m-}$ with M being selected from the group of transition metals and X being selected from As and/or P. Protocols for the preparation of these POMs were developed. Furthermore, the POMs were found to be useful as catalysts.

US 2005/0112055 A1 discloses a POM including three different transition metals Ru, Zn and W with the formula $Na_{14}[Ru_2Zn_2(H_2O)_2(ZnW_9O_{34})_2]$. This particular POM was found to be highly efficient as an electrocatalyst in the generation of oxygen.

WO 2007/139616 A1 discloses a class of W-based POMs including Ru with the formula $[Ru_2(H_2O)_6X_2W_{20}O_{70}]^{m-}$ with X being selected from Sb, Bi, As, Se, and Te. Protocols for the preparation of these POMs are described. Furthermore, the POMs were found to be useful as catalysts.

WO 2009/155185 A1 discloses a class of Ru and W-based POMs provided by the general formula

[Ru$_2$L$_2$(XW$_{11}$O$_{39}$)$_2$WO$_2$]$^{m-}$ with L being a ligand and X being Si, Ge, B and mixtures thereof. The POMs are useful as catalysts and precursors for the preparation of mixed metal-oxide catalysts.

In pursuit of noble metal-rich POM frameworks having a significantly higher noble metal-content as compared to previously known noble metal atom-containing POMs, i.e., POM frameworks containing a major proportion of noble metal atoms based on the overall metal content of said POM frameworks, Kortz and coworkers prepared the star-shaped polyoxo-15-palladate(II) [Pd$_{0.4}$Na$_{0.6}$⊂Pd$_{15}$P$_{10}$O$_{50}$H$_{6.6}$]$^{12-}$ (Dalton Trans. 2009, 9385-9387), the double-cuboid-shaped copper(II)-containing polyoxo-22-palladate(II) [Cu$^{II}_2$Pd$^{II}_{22}$P$^V_{12}$O$_{60}$(OH)$_8$]$^{20-}$ comprising two {CuPd$_{11}$} fragments (Angew. Chem. Int. Ed. 2011, 50, 2639-2642), and the polyoxo-22-palladate [Na$_2$Pd$^{II}_{22}$O$_{12}$(As$^V$O$_4$)$_{15}$(As$^V$O$_3$OH)]$^{25-}$ comprising two {NaPd$_{11}$} units (Dalton Trans. 2016, 45, 2394-2398).

In 2008, Kortz and coworkers reported the first representative of a new and highly promising class of noble metal-rich POMs, i.e., the molecular palladium-oxo polyanion [Pd$_{13}$As$_8$O$_{34}$(OH)$_6$]$^{8-}$ (Angew. Chem. Int. Ed. 2008, 47, 9542-9546). Twelve palladium atoms surround the thirteenth, the central palladium atom, resulting in a distorted icosahedral arrangement {PdPd$_{12}$O$_8$}. Each oxygen atom of the 'inner' PdO$_8$ fragment is coordinated by the central Pd atom and by three 'external' palladiums being situated on a trigonal face of a cuboctahedron. In 2009, two further representatives of said class of POMs have been reported, the discrete anionic PhAsO$_3$H$_2$- and SeO$_2$-derived palladium(II)-oxo clusters [Pd$_{13}$(As$^V$Ph)$_8$O$_{32}$]$^{6-}$ and [Pd$_{13}$Se$^{IV}_8$O$_{32}$]$^{6-}$ (Inorg. Chem. 2009, 48, 7504-7506).

In US 2009/0216052 A1 closely related POM analogues are disclosed based on this common structural motif comprising [M$_{13}$X$_8$R$_q$O$_y$]$^{m-}$ with M being selected from Pd, Pt, Au, Rh, Ir, and mixtures thereof, while X is a heteroatom such as As, Sb, Bi, P, Si, Ge, B, Al, Ga, S, Se, Te, and mixtures thereof. These POMs were in general demonstrated to be promising candidates for the further development of useful catalysts and precursors for mixed metal-oxide catalysts and metal clusters (also referred to as metal-clusters).

Kortz and coworkers also developed a related subclass of POMs displaying a similar structural arrangement but a slightly different elemental composition. In the [MPd$_{12}$P$_8$O$_{40}$H$_z$]$^{m-}$ polyanions the 'inner' MO$_8$ motif is also surrounded by twelve square-planar PdO$_4$ units and M is represented by Mn$^{II}$, Fe$^{III}$, Co$^{II}$, Cu$^{II}$ and Zn$^{II}$ (Chem. Eur. J. 2012, 18, 6167-6171).

In this context, Kortz and coworkers found that in the [MO$_8$Pd$_{12}$L$_8$]$^{n-}$ polyanions the 8-fold coordinated guest metal ions M, which are incorporated in the cuboidal {Pd$_{12}$O$_8$L$_8$} shell, can be selected from Sc$^{III}$, Mn$^{II}$, Fe$^{III}$, Co$^{II}$, Ni$^{II}$, Cu$^{II}$, Zn$^{II}$ and Lu$^{III}$, while L is represented by PhAsO$_3^{2-}$, PhPO$_3^{2-}$ or SeO$_3^{2-}$ (Inorg. Chem. 2012, 51, 13214-13228).

Furthermore, Kortz and coworkers prepared a series of yttrium- and lanthanide-based heteropolyoxopalladate analogues containing [X$^{III}$Pd$^{II}_{12}$O$_{32}$(AsPh)$_8$]$^{5-}$ cuboid units with X being selected from Y, Pr, Nd, Sm, Eu, Gd, Tb, Dy, Ho, Er, Tm, Yb, and Lu (Chem. Eur. J. 2010, 16, 9076-9085).

In 2014, Kortz and coworkers published the first fully inorganic discrete gold-palladium-oxo polyanion [NaAu$_4$Pd$_8$O$_8$(AsO$_4$)$_8$]$^{11-}$ without the stabilization of any organic ligands and with both Au and Pd occupying the atom positions of the metal framework. With regard to the structure, the cubic 'NaO$_8$' moiety is surrounded by 12 noble metal centers, i.e., 4 Au and 8 Pd atoms, forming the classical cuboctahedron, which is capped by eight tetrahedral arsenate groups (Chem. Eur. J. 2014, 20, 8556-8560).

One common feature of the {M$_{13}$O$_8$}/{M'M$_{12}$O$_8$}-based class of noble metal-rich POMs is the nature of the eight capping groups; all representatives of said class comprise capping groups being exclusively based on P, As or Se. Further experiments by Kortz and coworkers indicate that the presence of these P, As or Se-based capping groups is essential for maintaining the structural integrity of the {M$_{13}$O$_8$}/{M'M$_{12}$O$_8$}-based POMs having the unique highly symmetrical structural arrangement with the 'inner' MO$_8$/M'O$_8$ motif and the surrounding cuboctahedral M$_{12}$ arrangement.

For example, by replacing the P, As or Se-based capping groups in a respective {LaPd$_{12}$}-motif by the naturally occurring amino acid cysteine a dodecanuclear palladium (II)-thio cluster [LaPd$_{12}$(C$_3$H$_5$NO$_2$S)$_3$(C$_3$H$_6$NO$_2$S)$_{21}$] is obtained (Inorg. Chem. 2016, 55, 7811-7813).

Even by replacing only two of the eight As-based capping groups in a {SrPd$_{12}$}-POM with acetate groups, an unusual low-symmetry open-shell structure [SrPd$_{12}$O$_6$(OH)$_3$(PhAsO$_3$)$_6$(OAc)$_3$]$^{4-}$ is obtained, wherein two of the eight 'inner' O$^{2-}$ ions are substituted by three OH$^-$ ions and thus the central Sr atom is nine-coordinated giving an 'inner' SrO$_6$(OH)$_3$ motif. Furthermore, [SrPd$_{12}$O$_6$(OH)$_3$(PhAsO$_3$)$_6$(OAc)$_3$]$^{4-}$ was found to be rather labile at least partially decomposing under aqueous conditions (Angew. Chem. Int. Ed. 2014, 53, 11974-11978).

In contrast, preliminary experiments indicated that the representatives of the {M$_{13}$O$_8$}/{M'M$_{12}$O$_8$}-based class of noble metal-rich POMs having the unique highly symmetrical structural arrangement with the 'inner' MO$_8$/M'O$_8$ motif, the surrounding cuboctahedral M$_{12}$-arrangement and P, As or Se-based capping groups are stable, e.g., under aqueous conditions. Furthermore, especially due to their high catalytic activity, which appears to stem from the unique combination of the 'inner' MO$_8$/M'O$_8$ and 'outer' M$_{12}$-cuboctahedral structural arrangement, and the variability of the elemental composition of the M$_{13}$/M'M$_{12}$ centers while maintaining said structural arrangement, the {M$_{13}$O$_8$}/{M'M$_{12}$O$_8$}-based class of noble metal-rich POMs has an exceptional potential in the development of new catalysts.

However, despite their highly promising catalytic activities and said exceptional potential in the development of new catalysts, representatives of said class of noble metal-rich POMs, also like other noble metal-rich POMs, still suffer from several drawbacks: (i) the synthesis of said POMs is tedious and expensive mostly due to the multiple reagents and substrates required in their preparation, (ii) activation of said POMs in order to enhance or enable their catalytic activity requires rather harsh conditions, i.e., significantly elevated temperatures, leading to various decomposition products and thus decreased catalyst quality, purity, concentration and performance, and (iii) most of said POMs contain elements or units that are highly toxic or liberate highly toxic compounds in the process of activation in order to enhance or enable their catalytic activity or in the catalytic process itself.

Thus, there is a need for new and improved POMs containing a major proportion of metals other than early transition metals, based on the overall metal content of said POMs, in particular noble metal-rich POMs, and showing useful properties in homogeneous or heterogeneous catalytic applications. In this regard, particularly those POMs which solely contain noble metals, i.e., which do not contain any other metal atoms than noble metal atoms, and those which contain more than one different type of noble metal atom species and in particular those POMs which contain a major proportion of noble metals, i.e., which contain a major proportion of noble metal atoms doped with a minor proportion of other metal atoms than noble metal atoms, and those which contain more than one different type of noble metal atom species doped with other metals are highly promising candidates en route to new, more efficient and more selective catalysts due to the well-established unique catalytic properties of noble metals.

Therefore, it is an object of the present invention to provide POMs containing inter alia a major proportion of noble metal atoms possibly doped with other metals, based on the overall metal content of said POMs. Furthermore, it is an object of the present invention to provide one or multiple processes for the preparation of said POMs. In addition, it is an object of the present invention to provide supported POMs containing a major proportion of noble metal atoms, based on the overall metal content of said POMs as well as one or multiple processes for the preparation of said supported POMs. Another object of the present invention is the provision of metal clusters, in particular the provision of highly dispersed metal cluster particles, and processes for the preparation of said metal clusters either in the form of a dispersion in a liquid carrier medium or in supported form, immobilized on a solid support. Finally, it is an object of the present invention to provide one or multiple processes for the homogeneous or heterogeneous reductive conversion of organic substrate using said optionally supported POM(s) and/or said optionally supported or dispersed metal cluster(s).

SUMMARY OF THE INVENTION

An objective of the present invention among others is achieved by the provision of POMs represented by the formula

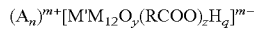

$(A_n)^{m+}[M'M_{12}O_y(RCOO)_zH_q]^{m-}$ or solvates thereof, wherein
  each A independently represents a cation,
  n is the number of cations,
  each M is independently selected from the group consisting of Pd, Pt, Rh, Ir, Ag and Au, and each M has $d^8$ valence electron configuration,
  M' is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg, lanthanide metal, Ga, In, Tl, Ge, Sn, Pb, Sb and Bi,
  each RCOO is a carboxylate-based group, wherein each R is independently selected from the group consisting of a hydrogen atom and a radical which is covalently bonded to the carbon atom of the carboxylate group COO, wherein each R that is not hydrogen provides a carbon atom for coordination to the carbon atom of the carboxylate group COO,
  y is a number from 8 to 16,
  z is a number from 12 to 24,
  q is a number from 0 to 8, and
  m is a number representing the total positive charge m+ of n cations A and the corresponding negative charge m− of the polyanion $[M'M_{12}O_y(RCOO)_zH_q]$.

These noble metal-rich POMs are inter alia based on square planar $MO_4$ building blocks, wherein each M has a $d^8$ valence electron configuration. Based on the $d^8$ valence electron configuration, the oxidation state of the respective M can be identified, so that M is $Pd^{II}$, $Pt^{II}$, $Rh^I$, $Ir^I$, $Ag^{III}$ or $Au^{III}$. Hence the requirement for M having a $d^8$ valence electron configuration is synonymous to M being selected from the group consisting of $Pd^{II}$, $Pt^{II}$, $Rh^I$, $Ir^I$, $Ag^{III}$, and $Au^{III}$.

An objective of the present invention among others is achieved by the provision of a process for the preparation of any one of the POMs provided by the present invention, said process comprising:
  (a) reacting at least one source of M and at least one source of M' with at least one RCOO-containing starting material to form a salt of the polyanion $[M'M_{12}O_y(RCOO)_zH_q]$ or a solvate thereof,
  (b) optionally adding at least one salt of A to the reaction mixture of step (a) to form a polyoxometalate $(A_n)^{m+}[M'M_{12}O_y(RCOO)_zH_q]^{m-}$ or a solvate thereof, and
  (c) recovering the polyoxometalate or solvate thereof.

An objective of the present invention among others is achieved by the provision of supported POMs comprising any one of the POMs provided by the present invention or prepared according to the present invention, on a solid support.

An objective of the present invention among others is achieved by the provision of a process for the preparation of the supported POMs provided by the present invention, said process comprising the step of contacting any one of the POMs provided by the present invention or prepared according to the present invention, with a solid support.

An objective of the present invention among others is achieved by the provision of metal clusters of the formula

$[M'M^0_{12}]$ wherein
  each $M^0$ is independently selected from the group consisting of $Pd^0$, $Pt^0$, $Rh^0$, $Ir^0$, $Ag^0$, and $Au^0$, preferably $Pd^0$ and $Pt^0$, most preferably $Pd^0$; in particular wherein all $M^0$ are the same, preferably wherein all $M^0$ are $Pd^0$, and
  M' is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg, lanthanide metal, Ga, In, Tl, Ge, Sn, Pb, Sb, and Bi, and the oxidation state of M' is 0 or greater than 0; preferably M' is Pd or Pt or is selected from the group consisting of Ga, In, Tl, Ge, Sn, Pb, Sb, and Bi; more preferably M' is Pd or is selected from the group consisting of Ga, In, Tl and Sn; most preferably M' is $Pd^0$ or $In^0$ or $Tl^0$, such as $In^0$.

An objective of the present invention among others is achieved by the provision of metal clusters of the formula $[M'M^0_{12}]$ obtainable by reduction of any one of the POMs provided by the present invention or prepared according to the present invention, wherein M and M' are the same as defined above for POMs represented by the formula $(A_n)^{m+}[M'M_{12}O_y(RCOO)_zH_q]^{m-}$.

An objective of the present invention among others is achieved by the provision of the metal clusters provided by the present invention in the form of a dispersion in a liquid carrier medium.

An objective of the present invention among others is achieved by the provision of supported metal clusters comprising any one of the metal clusters provided by the present invention immobilized on a solid support.

An objective of the present invention among others is achieved by the provision of a process for the preparation of any one of the metal clusters provided by the present invention, in the form of a dispersion of said metal clusters dispersed in a liquid carrier medium, said process comprising the steps of
(a) dissolving any one of the POMs provided by the present invention or prepared according to the present invention in a liquid carrier medium,
(b) optionally providing additive means to prevent agglomeration of the metal cluster to be prepared, and
(c) subjecting the dissolved POM to chemical or electrochemical reducing conditions sufficient to at least partially reduce said POM into corresponding metal clusters.

An objective of the present invention among others is achieved by the provision of a process for the preparation of supported metal clusters, i.e., any one of the metal clusters provided by the present invention, in the form of metal clusters immobilized on a solid support, said process comprising the steps of
(a) contacting the dispersion of metal clusters provided by the present invention or prepared according to the present invention, with a solid support, thereby immobilizing at least part of the dispersed metal clusters onto the support and obtaining supported metal clusters; and
(b) optionally isolating the supported metal clusters.

An objective of the present invention among others is achieved by the provision of a process for the preparation of supported metal clusters, i.e., any one of the metal clusters provided by the present invention, in the form of metal clusters immobilized on a solid support, said process comprising the steps of
(a) subjecting any one of the supported POM provided by the present invention or prepared according to the present invention to chemical or electrochemical reducing conditions sufficient to at least partially reduce said POM into corresponding metal clusters provided by the present invention; and
(b) optionally isolating the supported metal clusters.

An objective of the present invention among others is achieved by the provision of a process for the homogeneous or heterogeneous reductive conversion of organic substrate comprising contacting said organic substrate under addition of hydrogen with any one of the optionally supported POMs provided by the present invention or prepared according to the present invention, and/or with any one of the optionally dispersed or supported metal clusters provided by the present invention or prepared according to the present invention.

In the context of the present invention the term noble metal comprises the following elements: Rh, Ir, Pd, Pt, Ag, and Au.

In the context of the present invention the term noble metal-rich as being used in describing the noble metal content of a compound, in particular a POM, means that the major proportion of the metal atoms, based on the overall metal content of said compound, are noble metal atoms, in particular ≥60%, ≥70%, ≥80%, ≥90% or 100%, wherein the foregoing %-values are to be understood as referring to atom % based on the overall metal content of said compound. In the context of the POMs according to the present invention the overall metal content of said POM is to be understood as referring to the metal atoms within the POM framework, but not to any counterions outside the POM framework, i.e., any metal atom within the $[M'M_{12}O_y(RCOO)_zH_q]$ polyanion, but not the cations A.

In the context of the present invention the term post-transition metal comprises the following elements: Ga, In, Tl, Ge, Sn, Pb, Sb, and Bi.

In the context of the present invention the term carboxylate-based group comprises carboxylate ions which can be bonded to one or more metal ions, preferably to one or two metal ions, via one or both of the two oxygen atoms of the carboxylate ion. As is well-established in the art, carboxylate ions in general can serve as monodentate or bidentate ligands. Carboxylate ions can also be easily obtained by common techniques well-established in the art, such as deprotonation of a carboxylic acid, hydrolysis of a carboxylic acid ester under basic conditions or dissociation of carboxylate salts.

With regard to the present invention the expressions Group 1, Group 2, Group 3 etc. refer to the Periodic Table of the Elements and the expressions 3d, 4d and 5d metals refer to transition metals of respective Periods 4, 5 and 6 of the Periodic Table of the Elements, i.e., the 4d metal in Group 10 is Pd.

With regard to the present invention the term cuboctahedron describes the structural arrangement of the 12 M atoms in $(A_n)^{m+}[M'M_{12}O_y(RCOO)_zH_q]^{m-}$.

With regard to the present invention the term guest atom describes the centrally located M' atom within the cuboctahedron in $(A_n)^{m+}[M'M_{12}O_y(RCOO)_zH_q]^{m-}$.

With regard to the present invention the term polyanion describes the negatively charged structural arrangement $[M'M_{12}O_y(RCOO)_zH_q]$.

With regard to the present invention the term metal cluster describes the structural arrangement $[M'M^0_{12}]$.

With regard to the present invention the term nanocube describes the structural arrangement formed by the M and M' atoms and the RCOO groups $M'M_{12}(RCOO)_z$.

With regard to the present invention the term immobilizing means to render immobile or to fix the position. In the context of a solid support the term immobilizing describes the adhesion to a surface by means of adsorption, including physisorption and chemisorption. Adsorption is based on interactions between the material to be adsorbed and the surface of the solid support such as van-der-Waals interactions, hydrogen-bonding interactions, ionic interactions, etc.

With regard to the present invention the expression primary particles of POM or POMs primary particles describes isolated particles that contain exactly one negatively charged polyanion $[M'M_{12}O_y(RCOO)_zH_q]$. The POMs primary particles of the present invention are substantially mono-dispersed particles, i.e., the POMs primary particles have a uniform size, corresponding to the size of one polyanion. The expression POMs secondary particles describes agglomerates of POMs primary particles.

With regard to the present invention the term supported POM describes POM immobilized on a solid support.

With regard to the present invention the expression primary particles of metal cluster or metal cluster primary particles describes isolated particles that contain exactly one metal cluster $[M'M^0_{12}]$. The metal cluster primary particles of the present invention are substantially mono-dispersed particles, i.e., the metal cluster primary particles have a substantially uniform size, corresponding to the size of one metal cluster. The expression metal cluster secondary particles describes agglomerates of metal cluster primary particles.

The particle size of the non-aggregated and aggregated POMs, and of the non-aggregated and aggregated metal clusters, respectively, can be determined by various physical methods known in the art. If the particles are dispersed in a liquid medium, the particle size can be determined by light scattering. If the particles are supported on a solid support, solid state techniques are required for determining the particle size of the supported particles, and to distinguish between primary particles (non-aggregated) and secondary particles (aggregated). Suitable solid state techniques include scanning electron microscopy (SEM), transmission electron microscopy (TEM), powder X-ray diffraction or crystallography (powder XRD), etc. Another suitable technique for determining the particle size is pulsed chemi-/physisorption.

With regard to the present invention the term supported metal cluster describes metal clusters immobilized on a solid support.

BRIEF DESCRIPTION OF THE FIGS. 1-8

FIG. 1: Thermogravimetric analysis (TGA) curve of $K_5[In^{III}Pd^{II}_{12}O_8(H_3CCOO)_{16}] \cdot K_2Pd(H_3CCOO)_4 \cdot 4K(H_3CCOO) \cdot 20H_2O$ ("K—InPd$_{12}$") from 20° C. to 800° C.

Figure 2:
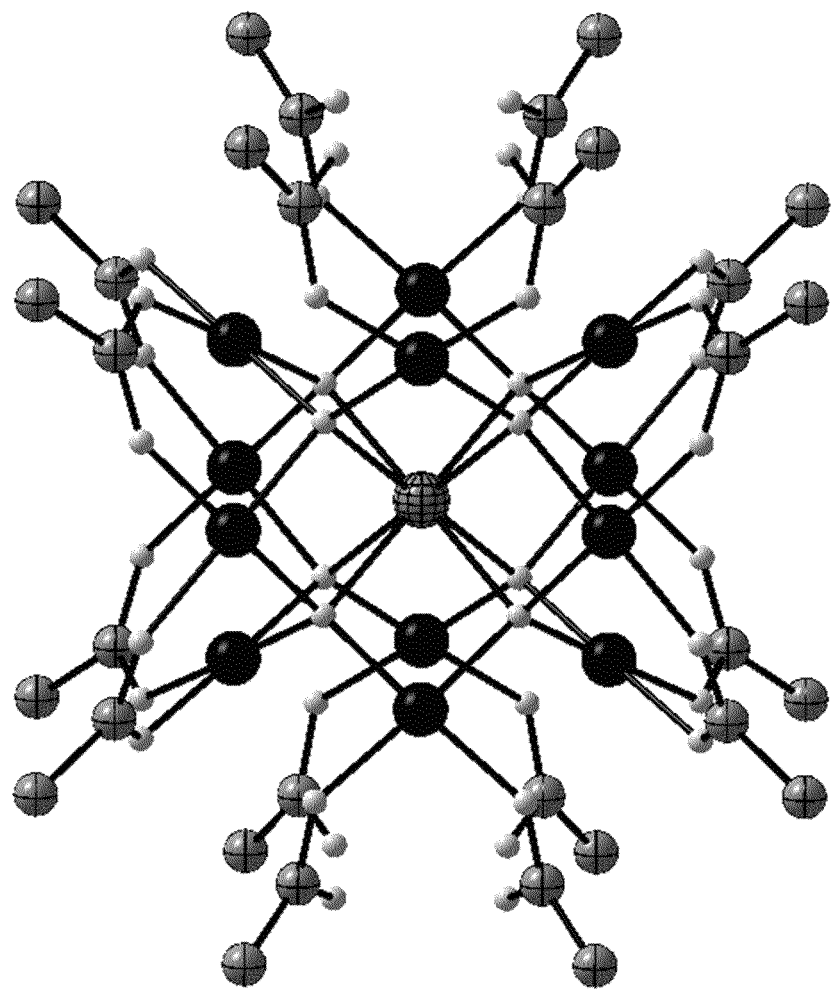

FIG. 2: Ball-and-stick representation of the $[In^{III}Pd^{II}_{12}O_8(H_3CCOO)_{16}]^{5-}$ polyanion ("InPd$_{12}$"). Legend: Pd, black spheres; In, grey sphere with gridding; C, grey spheres with cross-line; O, grey spheres.

Figure 3:
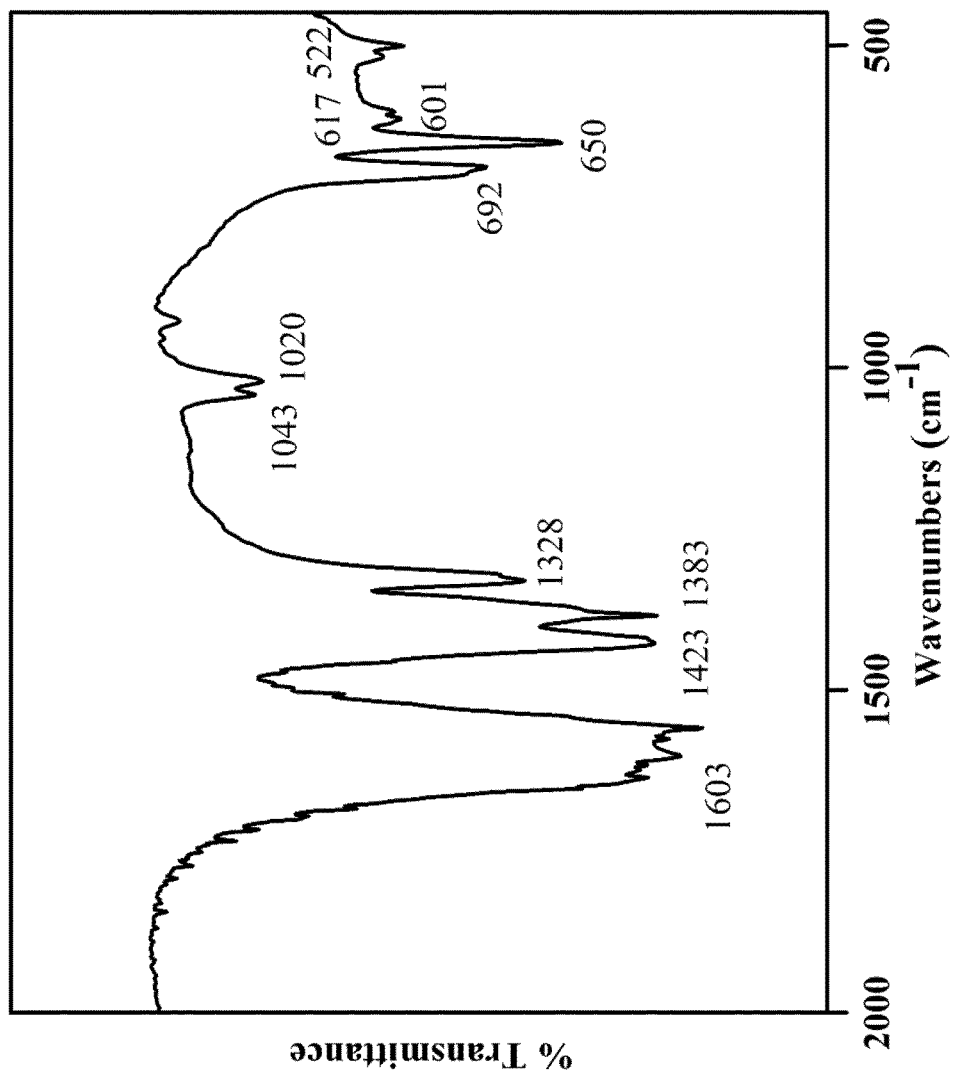

FIG. 3: Fourier Transform Infrared (FT-IR) Spectrum of $K_5[In^{III}Pd^{II}_{12}O_8(H_3CCOO)_{16}] \cdot K_2Pd(H_3CCOO)_4 \cdot 4K(H_3CCOO) \cdot 20H_2O$ ("K—InPd$_{12}$").

Figure 4:
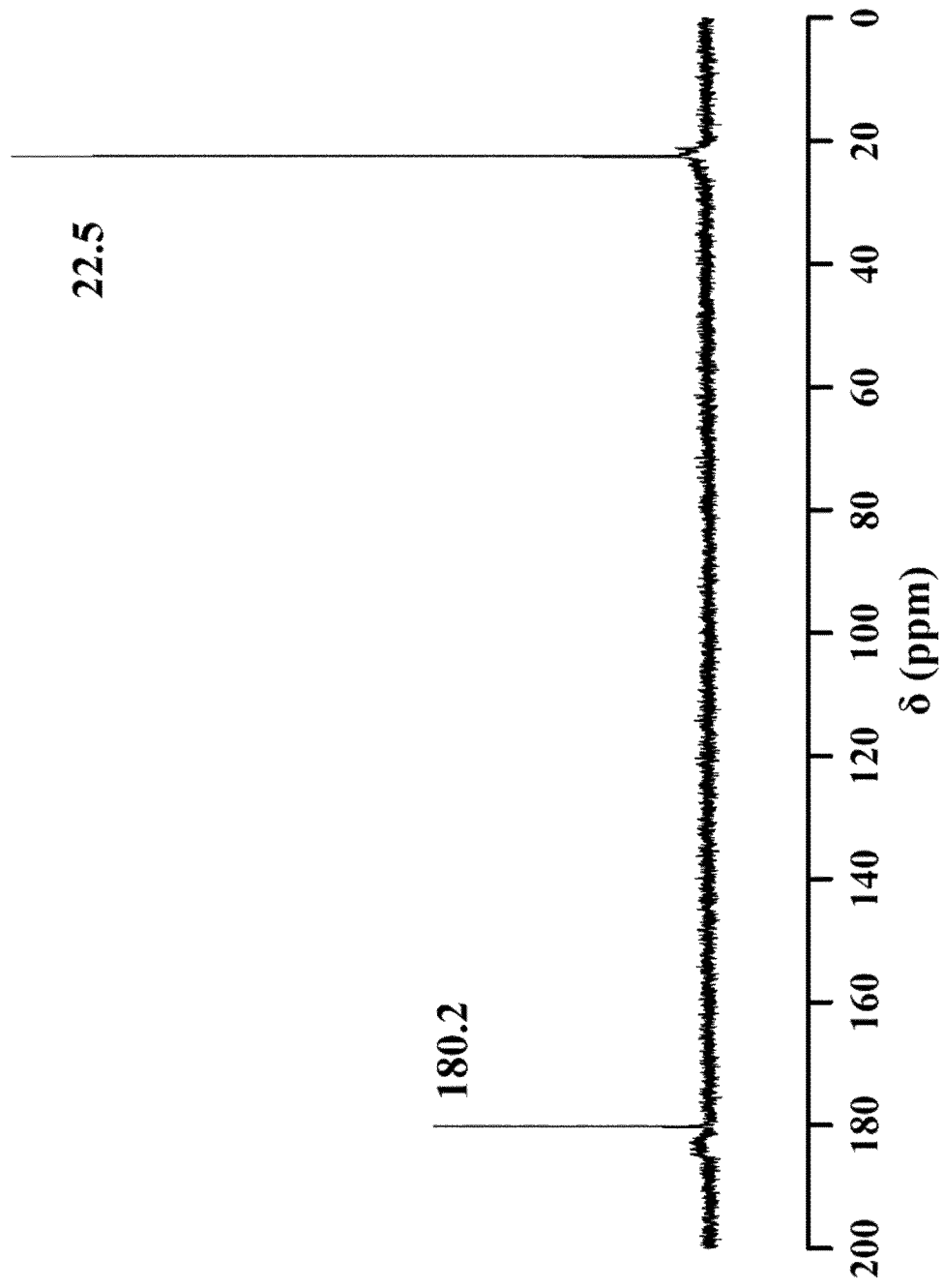

FIG. 4: $^{13}C$ NMR spectrum of $K_5[In^{III}Pd^{II}_{12}O_8(H_3CCOO)_{16}] \cdot K_2Pd(H_3CCOO)_4 \cdot 4K(H_3CCOO) \cdot 20H_2O$ ("K—InPd$_{12}$")

Figure 5:
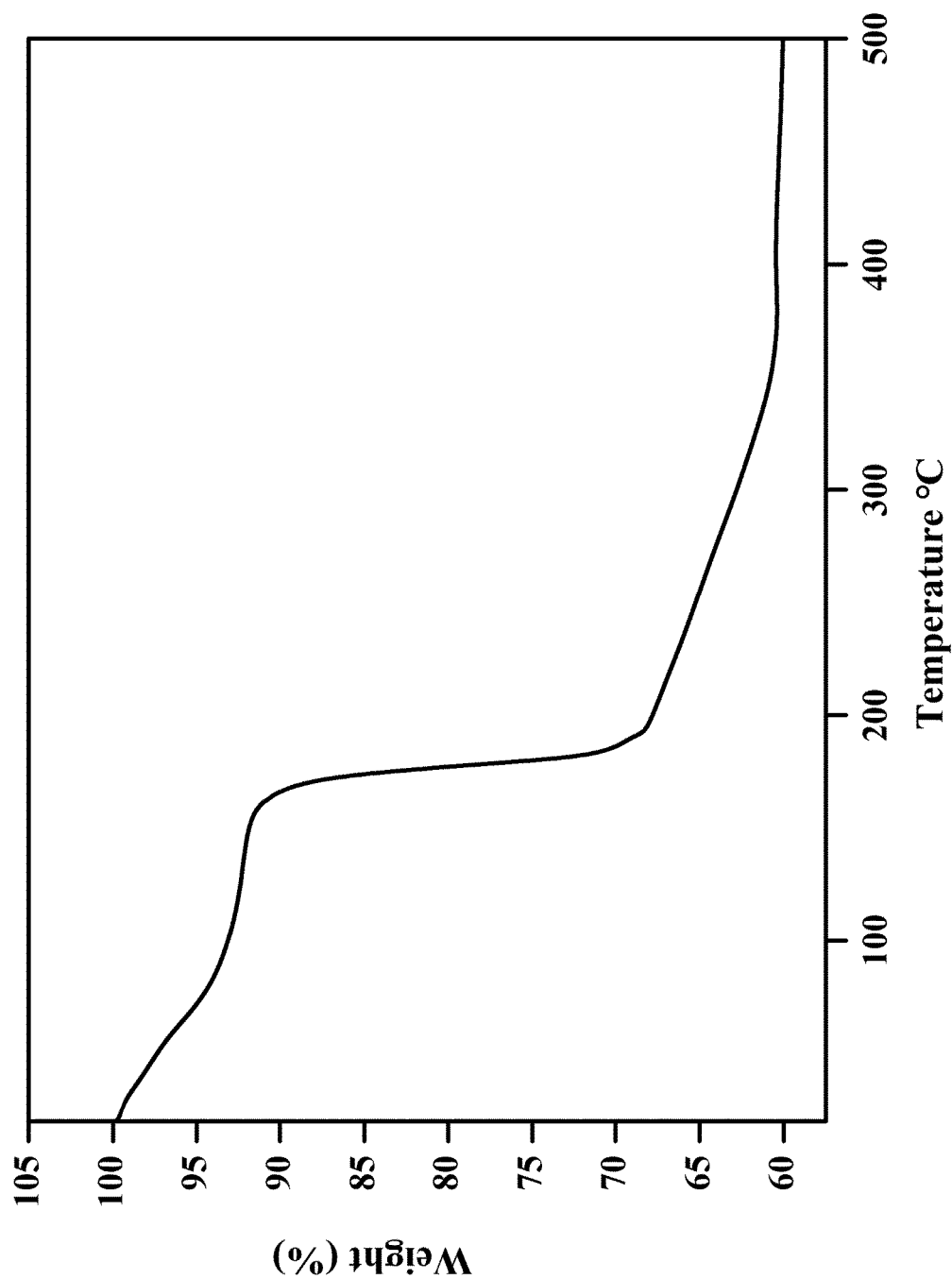

FIG. 5: Thermogravimetric analysis (TGA) curve of $K_5[Tl^{III}Pd^{II}_{12}O_8(H_3CCOO)_{16}] \cdot K_2Pd(H_3CCOO)_4 \cdot 4K(H_3CCOO) \cdot 20H_2O$ ("K—TlPd$_{12}$") from 20° C. to 800° C.

Figure 6:
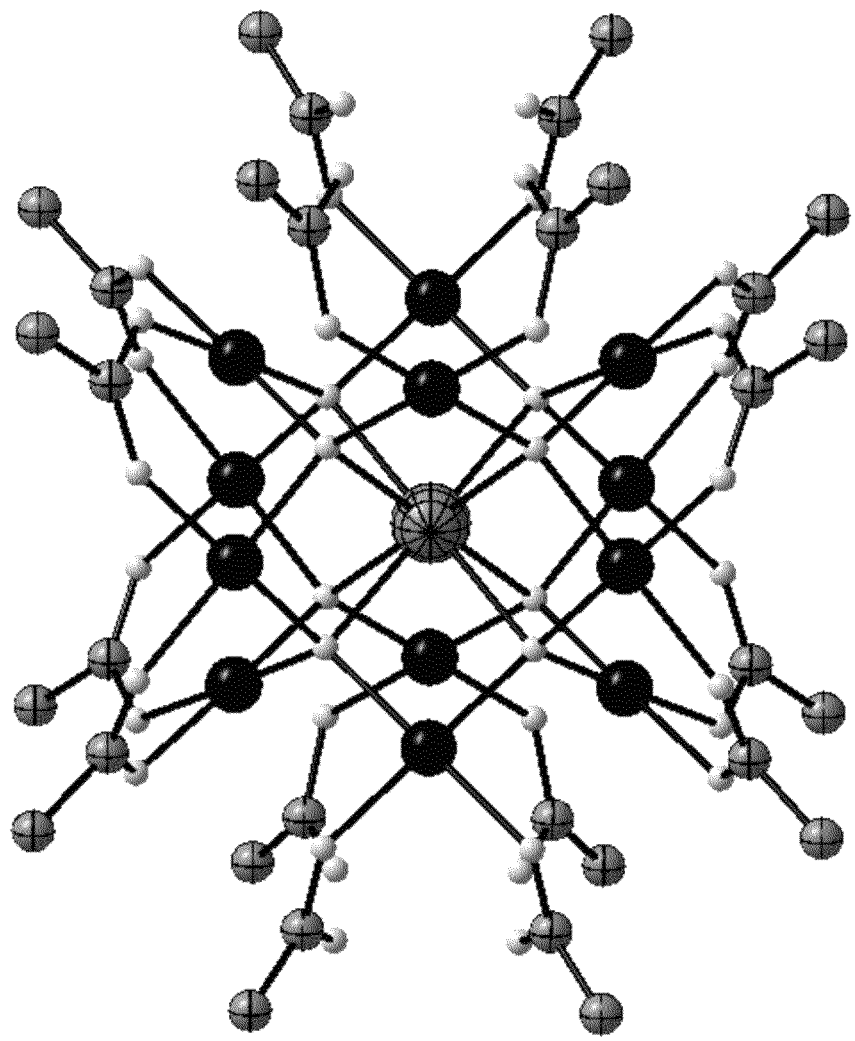

FIG. 6: Ball-and-stick representation of the $[Tl^{III}Pd^{II}_{12}O_8(H_3CCOO)_{16}]^{5-}$ polyanion ("TlPd$_{12}$"). Legend: Pd, black spheres; Tl, grey sphere with gridding; C, grey spheres with cross-line; O, grey spheres.

Figure 7:
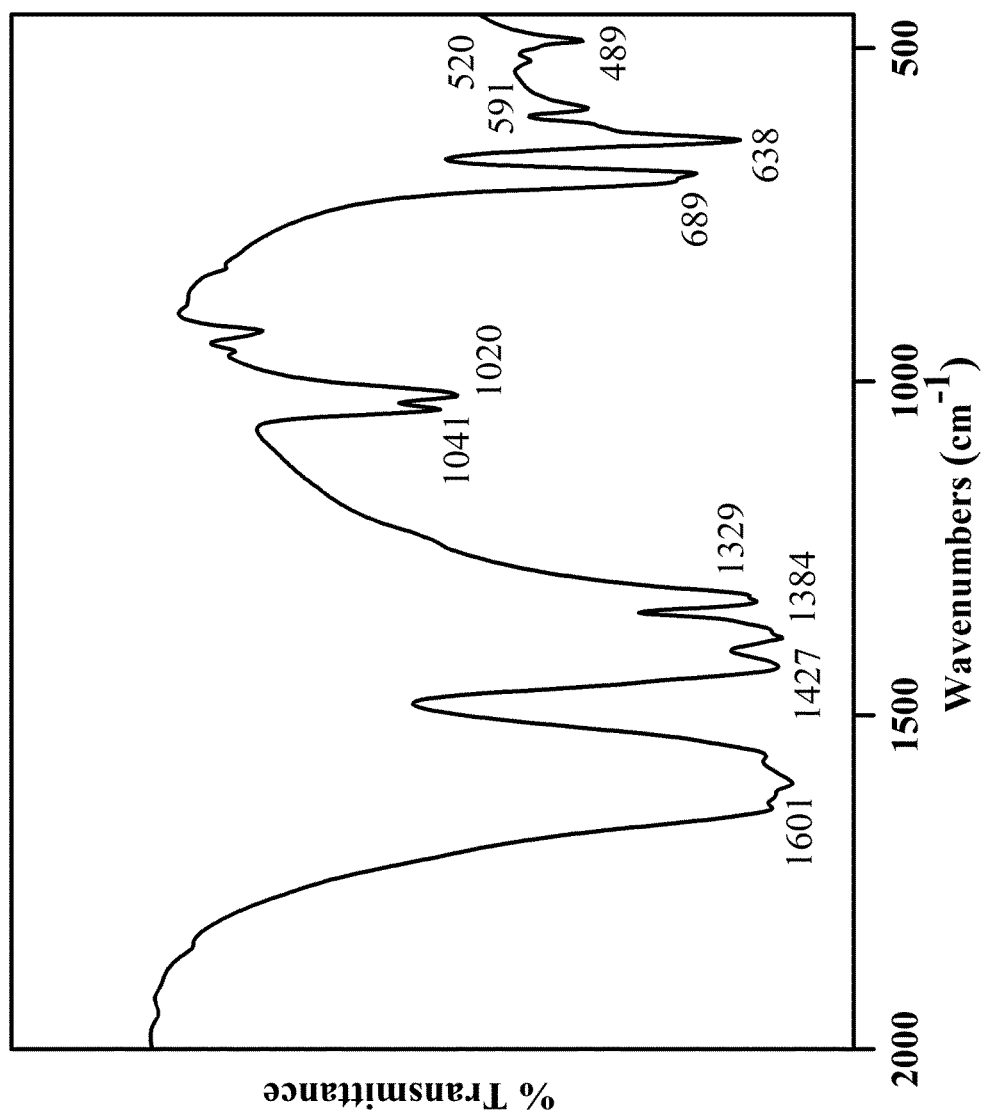

FIG. 7: Fourier Transform Infrared (FT-IR) Spectrum of $K_5[Tl^{III}Pd^{II}_{12}O_8(H_3CCOO)_{16}] \cdot K_2Pd(H_3CCOO)_4 \cdot 4K(H_3CCOO) \cdot 20H_2O$ ("K—TlPd$_{12}$").

Figure 8:
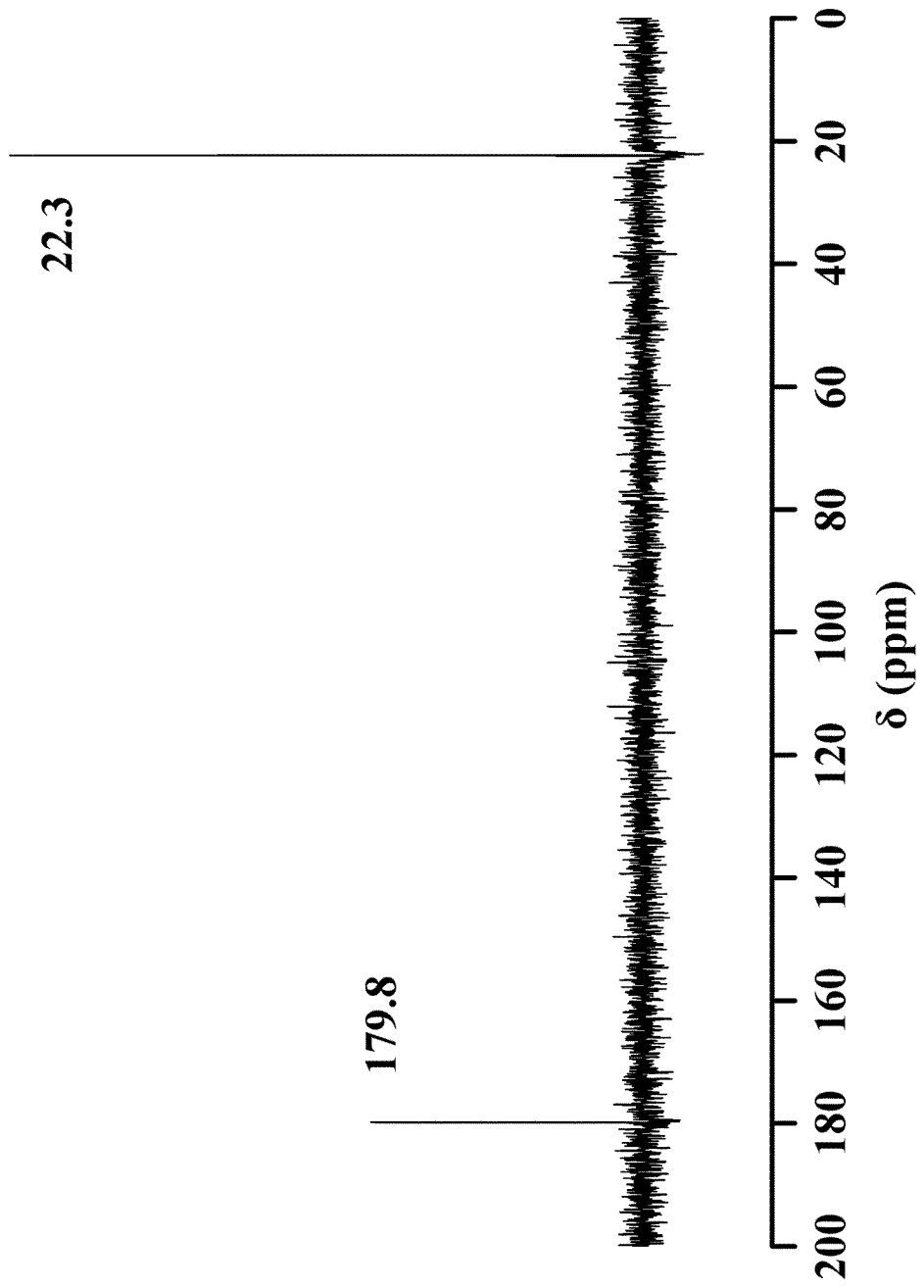

FIG. 8: $^{13}C$ NMR spectrum of $K_5[Tl^{III}Pd^{II}_{12}O_8(H_3CCOO)_{16}] \cdot K_2Pd(H_3CCOO)_4 \cdot 4K(H_3CCOO) \cdot 20H_2O$ ("K—TlPd$_{12}$").

DETAILED DESCRIPTION

According to one embodiment, the POMs of the present invention are represented by the formula

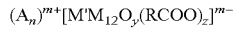

or solvates thereof, wherein
  each A independently represents a cation, preferably each A is independently selected from the group consisting of cations of Li, Na, K, Rb, Cs, Mg, Ca, Sr, Ba, Sc, Ti, V, Cr, Mn, Fe, Co, Ni, Cu, Zn, Y, Zr, Ru, Rh, Pd, Pt, Ag, Cd, Lu, Hf, Re, Os, Ir, Pt, Au, Hg, La, lanthanide metal, actinide metal, Ga, In, Tl, Ge, Sn, Pb, Sb, Bi, Te; or phosphonium, ammonium, guanidinium, tetraalkylammonium, protonated aliphatic amines, protonated aromatic amines, or combinations thereof; more preferably, A is selected from lithium, potassium, sodium cations and combinations thereof, n is the number of cations,
  each M is independently selected from the group consisting of Pd, Pt, Rh, Ir, Ag, and Au, preferably Pd, Pt, Rh, Ir, and Au, more preferably Pd, Pt and Rh, most preferably Pd and Pt, in particular Pd, and each M has $d^8$ valence electron configuration,
  M' is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg, lanthanide metal, Ga, In, Tl, Ge, Sn, Pb, Sb and Bi; preferably Sr, Sc, Ti, V, Cr, Mn, Fe, Co, Ni, Cu, Zn, Y, Zr, Ru, Rh, Pd, Ag, Cd, Lu, Re, Os, Ir, Pt and Au, more preferably Ti, V, Cr, Mn, Fe, Co, Ni, Cu, Zn, Ru, Rh, Pd, Ag, Re, Os, Ir, Pt and Au, even more preferably Rh, Pd, Ag, Ir, Pt and Au, still more preferably Pd, Pt and Au, most preferably Pd and Pt, in particular Pd; or preferably Ga, In, Tl, Ge, Sn, Pb, Sb and Bi, more preferably Ga, In, Tl, Sn, Pb, Sb and Bi, even more preferably Ga, In, Tl, Sn and Pb, most preferably Ga, In, Tl and Sn, in particular In and Tl, such as In,
  y is a number from 8 to 16, preferably 8, 9, 10, 11, 12 or 16, more preferably 8, 10, 12 or 16, most preferably 8, 12 or 16, in particular 8 or 16, more particularly 8.
  m is a number representing the total positive charge m+ of n cations A and the corresponding negative charge m− of the polyanion $[M'M_{12}O_y(RCOO)_z]$,
  each RCOO is a carboxylate-based group, wherein each R is independently selected from the group consisting of a hydrogen atom and a radical which is covalently bonded to the carbon atom of the carboxylate group COO, wherein each R that is not hydrogen provides a carbon atom for coordination to the carbon atom of the carboxylate group COO and
  z is a number from 12 to 24, preferably 12, 14, 16, 18, 20, 22 or 24, more preferably 12, 16, 20 or 24, most preferably 12, 16 or 24, in particular 12 or 16, more particularly 16.

According to a second embodiment, the POMs of the present invention are represented by the formula

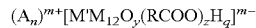

or solvates thereof, wherein
  A, n, m, M, M', y, RCOO and z are the same as defined above, and
  q is a number from 0 to 8, preferably 0 to 6, more preferably 0 to 4, most preferably 0.

In a first preferred variant of the first or second embodiments, all M are the same; preferably wherein all M are the same, and are selected from Pd, Pt, Rh, Ir, and Au, more preferably Pd, Pt and Rh, most preferably Pd and Pt, in particular Pd.

In a second preferred variant of the first or second embodiments or of the first preferred variant of said embodiments, M' has $d^8$ valence electron configuration and is selected from Pd, Pt, Rh, Ir, and Au, more preferably Pd, Pt and Au, most preferably Pd and Pt, in particular Pd.

In a third preferred variant of the first or second embodiments or of the preferred variants of said embodiments, all M are Pd or Pt, M' is selected from the group consisting of Pd, Pt and Au, and y is 8, preferably wherein q is 0, 2, 4, 6 or 8 and z is 16, more preferably wherein q is 0 and z is 16; in particular all M are Pd, M' is Pd and y is 8; more particularly wherein q is 0 and z is 16.

In a fourth preferred variant of the first or second embodiments or of the first preferred variant of said embodiments, M' is selected from the group of post-transition metals Ga, In, Tl, Ge, Sn, Pb, Sb, and Bi having an oxidation state of +3 or higher, preferably M' is selected from the group of post-transition metals having an oxidation state of +3, +4 or +5, preferably M' is selected from the group of post-transition metals having an oxidation state of +3; in particular M' is selected from the group consisting of $Ga^{III}$, $In^{III}$, $Tl^{III}$, $Ge^{IV}$, $Sn^{IV}$, $Pb^{IV}$, $Sb^{III}$, $Sb^{V}$, $Bi^{III}$ and $Bi^{V}$, preferably M' is selected from the group consisting of $Ga^{III}$, $In^{III}$, $Tl^{III}$, $Sn^{IV}$, $Pb^{IV}$, $Sb^{III}$, $Sb^{V}$, $Bi^{III}$ and $Bi^{V}$, more preferably M' is selected from the group consisting of $Ga^{III}$, $In^{III}$, $Tl^{III}$, $Sn^{IV}$ and $Pb^{IV}$, even more preferably M' is selected from the group consisting of $Ga^{III}$, $In^{III}$, $Tl^{III}$ and $Sn^{IV}$, most preferably M' is selected from the group consisting of $In^{III}$ and $Tl^{III}$, such as $In^{III}$.

In a fifth preferred variant of the first or second embodiments or of the first or fourth preferred variant of said embodiments, M' is selected from the group consisting of Ga, In, Tl, Ge, Sn, Pb, Sb and Bi, preferably Ga, In, Tl, Sn, Pb, Sb and Bi, more preferably Ga, In, Tl, Sn and Pb, even more preferably Ga, In, Tl and Sn, most preferably In and Tl, such as In; in particular all M are Pd, M' is In and y is 8; more particularly wherein q is 0 and z is 16.

The polyanion $[M'M_{12}O_y(RCOO)_zH_q]$ of the POMs according to the invention has been found to show structural analogies to the Keggin anion described above. It comprises twelve noble metal atoms M forming a distorted icosahedron (or distorted cuboctahedron) around the thirteenth central guest atom M'. In contrast to other known POMs in which the framework metal atom geometry is distorted octahedral (or more rarely, tetrahedral, square-pyramidal, or seven-coordinated), the 12 noble metal atoms M have a square-planar coordination sphere. The M cations provide a $d^8$ valence electron configuration. In a preferred embodiment, the large positive charge of the M and M' metal cations is compensated by oxo anions $O^{2-}$ incorporated in the $M'M_{12}$ assembly having approximately cuboctahedral symmetry (e.g., FIG. 2).

In a preferred embodiment, the polyanion $[M'M_{12}O_y(RCOO)_zH_q]$ is composed of a $M'M_{12}(RCOO)_z$ nanocube, with the central M' being 4 to 8-coordinated by the incorporated oxo anions $O^{2-}$, preferably 4, 6 or 8-coordinated, more preferably 4 or 8-coordinated, most preferably 8-coordinated. In a preferred embodiment, the framework of the polyanion $[M'M_{12}O_y(RCOO)_zH_q]$ can be divided into three parts (e.g., FIG. 2): the central 8-coordinated M' ion encapsulated in the classic $M_{12}$ cuboctahedron and then surrounded by 12 to 24, preferably 12, 14, 16, 18, 20, 22 or 24, more preferably 12, 16, 20 or 24, most preferably 12, 16 or 24, in particular 12 or 16, more particularly 16, carboxylate-based groups RCOO. According to the present invention, none of the RCOO groups is centrally located. All RCOO groups are external to the $M_{12}$ cuboctahedron.

In a preferred embodiment, in the solid state, each polyanion is surrounded by n, preferably 1 to 50, more preferably 1 to 30, most preferably 1 to 20, in particular 1 to 10, cations A to compensate the charge balance, and those cations, together with optional crystal water molecules and optional co-crystallizing entities, isolate the polyanions from each other.

The carboxylate-based groups RCOO can be monodentate or bidentate ligands, i.e., the carboxylate-based groups RCOO can be bonded via one or via both of the two oxygen atoms, respectively. The bidentate carboxylate-based groups RCOO can be bonded to either one or two different atoms. In a preferred embodiment, the bidentate carboxylate-based groups RCOO are bonded to two different atoms via each of the two oxygen atoms, respectively, i.e., each of the two oxygen atoms of the bidentate carboxylate-based group RCOO is bonded to a different atom. Monodentate carboxylate-based groups RCOO are bonded to one atom only, whereas bidentate carboxylate-based groups RCOO are bonded to two atoms.

The POMs according to the present invention contain only monodentate carboxylate-based groups RCOO, only bidentate carboxylate-based groups RCOO or a combination of monodentate and bidentate carboxylate-based groups RCOO. In a preferred embodiment, the POMs according to the present invention contain a combination of monodentate and bidentate carboxylate-based groups RCOO (see, e.g., FIG. 2).

In a preferred embodiment, two adjacent coordination sites of the square-planar coordination sphere of each of the 12 noble metal atoms M are occupied by carboxylate-based groups RCOO. In a more preferred embodiment, two adjacent coordination sites of the square-planar coordination sphere of each of the 12 noble metal atoms M are occupied by monodentate and/or bidentate carboxylate-based groups RCOO, wherein the bidentate carboxylate-based groups RCOO are bonded to two different M atoms, and thus, each of the vertices of the cuboctahedron, i.e., each of the 12 M atoms, is capped by two carboxylate-based groups RCOO irrespective of whether the carboxylate-based groups RCOO are monodentate or bidentate.

Group R covalently bonded to the C atom of the carboxylate-based group RCOO allows for inter alia tuning of (i) the steric and electrostatic parameters on the surface of the POM, and (ii) the solubility properties of the POM ranging from hydrophilic to hydrophobic. Furthermore, if group R is a radical bonded to the carbon atom of the carboxylate group via a carbon atom of said radical and if said radical is further substituted by one or more additional moieties X comprising, e.g., a —COOH⁻ containing group, a POM polyanion can be linked via such a moiety X to one or more other POM polyanions, thus, forming chains or networks of POM polyanions.

The POMs of the present invention are in the form of primary and/or secondary particles. In an especially preferred embodiment, the POMs provided by the present invention are mainly in the form of primary particles (i.e., non-agglomerated primary particles), that is at least 90 wt % of the POMs are in the form of primary particles, preferably at least 95 wt %, more preferably at least 99 wt %, in particular substantially all the POMs particles are in the form of primary particles.

The size of the present POMs primary particles has been found to be about 1 nm³ determined by single-crystal X-ray diffraction analysis.

A specific example of a structure of a specific POM of the present invention is illustrated in FIG. 2.

In comparison to known TMSPs (transition metal-substituted POMs), the present POMs are characterized in that at least a major proportion of the metal atom positions of the POM framework is occupied by noble metal atoms selected from Rh, Ir, Pd, Pt, Ag, Au, and mixtures thereof, i.e., the POMs according to the present invention are noble metal-rich POMs.

Moreover, in contrast to known POMs, the present POMs are further characterized in that they feature one centrally located metal atom position in the POM framework, which position is occupied by metal atom selected from variety of different metal atoms, preferably a noble metal atom selected from Rh, Ir, Pd, Pt, Ag and Au, or a post-transition metal atom selected from Ga, In, Tl, Ge, Sn, Pb, Sb, and Bi, more preferably a noble metal atom selected from Rh, Ir, Pd, Pt, Ag and Au, such as Pd, or a post-transition metal atom selected from Ga, In, Tl and Sn, such as In. The combination of the one centrally located metal guest atom and the surrounding noble metal cuboctahedron provides for POMs having (i) an exceptionally robust polyanion framework and (ii) a unique catalytic performance in reduction reactions. Said unique catalytic performance of the POMs of the present invention stems from (i) the exceptionally high concentration and accessibility of the noble metal centers in the nanosized molecular entity described herein, from (ii)

the presence of the centrally located metal guest atom, in particular a noble metal or post-transition metal guest atom, and from (iii) the unique highly symmetrical structural arrangement with the 'inner' $MO_8/M'O_8$ motif and the surrounding cuboctahedral $M_{12}$-motif. While the inventors do not wish to be bound by any particular theory, the presence and nature of the metal guest atom also impacts the properties of the surrounding noble metal cuboctahedron, e.g., electronic properties, and thus in particular the catalytic performance of the POMs of the present invention. Hence, the overall properties of the POMs and in particular the catalytic performance in said reduction reactions can be fine-tuned by the specific choice of noble metal(s) M in combination with the centrally located metal guest atom M'.

In the POMs of the present invention, the cation A can be a Group 1, 2, 3, 4, 5, 6, 7, 8, 9, 10, 11, 12, 13, 14, 15 and 16 metal cation or an organic cation. Preferably, each A is independently selected from the group consisting of cations of Li, Na, K, Rb, Cs, Mg, Ca, Sr, Ba, Sc, Ti, V, Cr, Mn, Fe, Co, Ni, Cu, Zn, Y, Zr, Ru, Rh, Pd, Pt, Ag, Cd, Lu, Hf, Re, Os, Ir, Pt, Au, Hg, La, lanthanide metal, actinide metal, Ga, In, Tl, Ge, Sn, Pb, Sb, Bi, Te; or phosphonium, ammonium, guanidinium, tetraalkylammonium, protonated aliphatic amines, protonated aromatic amines; or combinations thereof. More preferably, A is selected from lithium, potassium, sodium cations and combinations thereof.

The number n of cations is dependent on the nature of cation(s) A, namely its/their valence, and the negative charge m of the polyanion which has to be balanced. In any case, the overall charge of all cations A is equal to the charge of the polyanion. In turn, the charge m of the polyanion is dependent on the nature and oxidation state of the metals M and M', the nature and oxidation state of the heteroatoms X and the number of oxygen atoms y. Thus, m depends on the oxidation state of the atoms present in the polyanion, e.g., it follows from the oxidation states of inter alia O (−2), M and M' (normally ranging from +1 to +5 such as +1 for Ag, Au, Rh, Ir, Na and K, +2 for Pd, Pt, Mg, Ca and Sr, +3 for Ag, Au, Ga, In and Tl, +4 for Ge, Sb and Pb, and +5 for Sb and Bi). In some embodiments, m ranges from 1 to 45. In particular, m is 3, 5, 6, 9, 10, 12, 14, 22, 30 or 35. In a preferred embodiment, m is 5 or 6. Thus, n can generally range from 1 to 45. In particular, n ranges from 3 to 30 and more particularly is 3, 5, 6, 10, 12, 14, 22 or 30. In a preferred embodiment, n is 5 or 6.

Generally, A is acting as counterion of the polyanion and is positioned outside of the polyanion. However, it is also possible that some of the cations A are located within the polyanion.

In contrast, if one or multiple protons are present as counterion(s) in a preferred embodiment, said one or multiple protons are located within the polyanion, and said one or multiple protons can be covalently bonded to oxygen atom(s) of the polyanion with the proviso that no more than one proton is bonded per oxygen. Thus, each proton being located on a POM and, preferably, being bonded to one or more of the oxygen atoms of the polyanion framework, is represented by one of q protons of the polyanion $[M'M_{12}O_y(RCOO)_zH_q]$.

Generally, q is ranging from 0 to 8. In particular, q is 0 or 4. In a preferred embodiment q is 0, i.e., no group H is present. In another embodiment q is 1, 2, 3, 4, 5, 6, 7, or 8. In a preferred embodiment of the present invention, wherein q is preferably 1, 2, 3, 4, 5, 6, 7, or 8, the q protons are bonded to oxygen atoms of the polyanion framework, with the proviso that each of said protons is bonded to a different oxygen atom of the polyanion framework. Thus, in this specific preferred embodiment the POM is best represented by the formulae

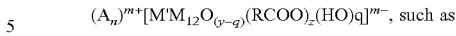, such as

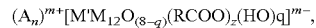, or solvates thereof, wherein A, n, m, M, M', y, R, z and q are the same as defined above.

The M atoms have a square-planar coordination sphere, and they provide a $d^8$ valence electron configuration. Preferably M is selected from $Pt^{II}$ or $Pd^{II}$, most preferably M is $Pd^{II}$. In a most preferred embodiment, all M are the same, and all M are $Pd^{II}$ at the same time. Preferably M' is selected from Pd, Pt, Rh, Ir, Ag and Au, most preferably M' is Pd, or M' is selected from Ga, In, Tl, Ge, Sn, Pb, Sb and Bi, preferably from Ga, In, Tl and Sn, most preferably M' is In or Tl, such as In. In a most preferred embodiment, M' is Pd, especially $Pd^{II}$, or M' is In or Tl, especially $In^{III}$.

In the context of the present invention each R is selected from the group consisting of a hydrogen atom and a radical which is covalently bonded to the C atom of the carboxylate group COO, wherein each R that is not hydrogen provides a carbon atom for coordination to the C atom of the carboxylate group COO, wherein each R may be the same or different. Preferably each R that is not hydrogen is a radical that is independently selected from the group consisting of alkyl, alkenyl, alkynyl, aryl, heteroaryl, cycloalkyl, heterocycloalkyl, and combinations thereof such as aryalkyl, arylalkenyl, cycloalkylalkyl, heterocycloalkylalkyl or heteroarylalkyl, preferably an alkyl. Each of said radicals can optionally be substituted with one or more moieties X which can be the same or different. In a first aspect, said moieties X can be selected from the group consisting of halogens, in particular F, Cl, Br or I, more particularly F or Cl, resulting in groups such as $—CF_3$ or $—CH_2Cl$. In a second aspect, said moieties X can be selected from the group consisting of $—CN$, $—C(O)OR^2$, $—C(O)R^2$, $—C(O)NR^2R^3$ and a further carboxylate group $—COO^-$, each of $R^2$ and $R^3$ being selected from the group consisting of H, alkyl, alkenyl, alkynyl, aryl, heteroaryl, cycloalkyl, and heterocycloalkyl, especially H or $C_1$-$C_6$ alkyl, such as H or $C_1$-$C_4$ alkyl. $COO^-$ containing moieties are especially suitable as a polyanion can be linked to one or more other polyanions through such an additional $COO^-$ group. In a third aspect, said moieties X can be bonded to the radical via an oxygen atom, said moieties X being selected from the group consisting of $—OR^2$, $—O(SO_2)R^2$, $—O(SO)R^2$, $—O(SO_2)OR^2$, $—O(SO)OR^2$, $—OS(O_2)NR^2R^3$, $—OS(O)NR^2R^3$, $—OPO(OR^2)_2$, $—OPO(OR^2)OR^3$, $—OPO(R^2)OR^3$, $—OC(O)R^2$, $—OC(O)NR^2R^3$ and $—OC(O)OR^2$; in particular $—OR^2$, $—O(SO_2)R^2$, $—O(SO_2)OR^2$, $—OS(O_2)NR^2R^3$, $—OPO(OR^2)_2$, $—OC(O)R^2$, $—OC(O)NR^2R^3$ and $—OC(O)OR^2$; more particularly $—OR^2$, $—O(SO_2)R^2$, $—OC(O)R^2$, $—OC(O)NR^2R^3$ and $—OC(O)OR^2$, wherein $R^2$ and $R^3$ are independently selected from the group consisting of H, alkyl, alkenyl, alkynyl, aryl, heteroaryl, cycloalkyl, and heterocycloalkyl, especially H or $C_1$-$C_6$ alkyl, such as H or $C_1$-$C_4$ alkyl. In a fourth aspect, said moieties X can be bonded to the radical via a sulfur atom, said moieties X being selected from the group consisting of $—SO_3R^2$, $—SR^2$, $—S(O_2)R^2$, $—S(O)R^2$, $—S(O)OR^2$, $—S(O)NR^2R^3$ and $—S(O_2)NR^2R^3$; in particular $—SO_3R^2$, $—SR^2$, $—S(O_2)R^2$ and $—S(O_2)NR^2R^3$; more particularly $—SR^2$ and $—S(O_2)R^2$, wherein $R^2$ and $R^3$ are independently selected from the group consisting of H, alkyl, alkenyl, alkynyl, aryl, heteroaryl, cycloalkyl, and heterocycloalkyl, especially H or $C_1$-$C_6$ alkyl, such as H or $C_1$-$C_4$ alkyl. In a fifth aspect, said moieties X can be bonded to the radical via a phosphorus atom, said moieties X being selected from the group consisting of —$POR^2R^3$, —$P(R^2)S(O_2)R^3$, —$P(R^2)S(O_2)PR^3R^4$, —$P(R^2)S(O_2)OR^3$, —$P(R^2)S(O)R^3$, —$P(R^2)S(O)PR^3R^4$, —$P(R^2)S(O)OR^3$, —$P(R^2)PO(OR^3)_2$, —$P(R^2)PO(OR^3)OR^4$, —$P(R^2)PO(R^3)OR^4$, —$P(R^2)C(O)R^3$, —$P(R^2)C(O)OR^3$ and —$P(R^2)C(O)PR^3R^4$; in particular —$POR^2R^3$, —$P(R^2)S(O_2)PR^3R^4$, —$P(R^2)S(O)R^3$, —$P(R^2)S(O)OR^3$, —$P(R^2)PO(OR^3)_2$, —$P(R^2)PO(R^3)OR^4$, —$P(R^2)C(O)R^3$, —$P(R^2)C(O)OR^3$ and —$P(R^2)C(O)PR^3R^4$; more particularly —$POR^2R^3$, —$P(R^2)S(O)R^3$, —$P(R^2)PO(OR^3)_2$, —$P(R^2)C(O)R^3$, and —$P(R^2)C(O)PR^3R^4$, wherein $R^2$, $R^3$ and $R^4$ are independently selected from the group consisting of H, alkyl, alkenyl, alkynyl, aryl, heteroaryl, cycloalkyl, and heterocycloalkyl, especially H or $C_1$-$C_6$ alkyl, such as H or $C_1$-$C_4$ alkyl. In a sixth aspect, said moieties X can be bonded to the radical via a nitrogen atom, said moieties X being selected from the group consisting of —$NR^2R^3$, —$N(R^2)S(O_2)R^3$, —$N(R^2)S(O_2)NR^3R^4$, —$N(R^2)S(O_2)OR^3$, —$N(R^2)S(O)R^3$, —$N(R^2)S(O)NR^3R^4$, —$N(R^2)S(O)OR^3$, —$N(R^2)PO(OR^3)_2$, —$N(R^2)PO(OR^3)OR^4$, —$N(R^2)PO(R^3)OR^4$, —$N(R^2)C(O)R^3$, —$N(R^2)C(O)OR^3$, —$N(R^2)C(O)NR^3R^4$ and —$NO_2$; in particular —$NR^2R^3$, —$N(R^2)S(O_2)R^3$, —$N(R^2)S(O_2)NR^3R^4$, —$N(R^2)S(O_2)OR^3$, —$N(R^2)PO(OR^3)_2$, —$N(R^2)C(O)R^3$, —$N(R^2)C(O)OR^3$, —$N(R^2)C(O)NR^3R^4$ and —$NO_2$; more particularly —$NR^2R^3$, —$N(R^2)S(O_2)R^3$, —$N(R^2)C(O)R^3$, —$N(R^2)C(O)OR^3$ and —$N(R^2)C(O)NR^3R^4$, wherein $R^2$, $R^3$ and $R^4$ are independently selected from the group consisting of H, alkyl, alkenyl, alkynyl, aryl, heteroaryl, cycloalkyl, and heterocycloalkyl, especially H or $C_1$-$C_6$ alkyl, such as H or $C_1$-$C_4$ alkyl. If a radical is substituted with more than one moiety X, said moieties X can be the same or different and can be independently selected from the first, second, third, fourth, fifth and sixth aspects as defined above.

In a preferred embodiment each R may be the same or different and is selected from the group consisting of a hydrogen atom and a radical which is covalently bonded to the C atom of the carboxylate group COO, wherein each R that is not hydrogen provides a carbon atom for coordination to the C atom of the carboxylate group COO, wherein each R that is not hydrogen is a radical that is independently selected from the group consisting of alkyl, aryl, heteroaryl, cycloalkyl, heterocycloalkyl, and combinations thereof, preferably alkyl, aryl, and cycloalkyl.

In a very preferred embodiment each R may be the same or different and is selected from the group consisting of a hydrogen atom and a radical which is covalently bonded to the C atom of the carboxylate group COO, wherein each R that is not hydrogen provides a carbon atom for coordination to the C atom of the carboxylate group COO, wherein each R that is not hydrogen is alkyl.

As used herein, "alkyl" represents a straight or branched aliphatic hydrocarbon group with 1 to about 20 carbon atoms. Preferred alkyl groups contain 1 to about 12 carbon atoms. More preferred alkyl groups contain 1 to about 6 carbon atoms such as 1 to about 4 carbon atoms. Non-limiting examples of suitable alkyl groups include methyl, ethyl, n-propyl, isopropyl and t-butyl. "Alkenyl" represents a straight or branched aliphatic hydrocarbon group containing at least one carbon-carbon double bond and having 2 to about 15 carbon atoms. Preferred alkenyl groups have 2 to about 12 carbon atoms; and more preferably 2 to about 4 carbon atoms. Non-limiting examples of suitable alkenyl groups include ethenyl, propenyl and 2-butenyl. "Alkynyl" represents a straight or branched aliphatic hydrocarbon group containing at least one carbon-carbon triple bond and having 2 to about 15 carbon atoms. Preferred alkynyl groups have 2 to about 12 carbon atoms; and more preferably 2 to about 4 carbon atoms. Non-limiting examples of suitable alkynyl groups include ethynyl, propynyl, 2-butynyl and 3-methylbutynyl. "Aryl" represents an aromatic monocyclic or multicyclic ring system comprising about 6 to about 14 carbon atoms, preferably about 6 to about 10 carbon atoms. Non-limiting examples of suitable aryl groups include phenyl and naphthyl. "Heteroaryl" represents an aromatic monocyclic or multicyclic ring system comprising about 5 to about 14 ring atoms, preferably about 5 to about 10 ring atoms, in which one or more of the ring atoms is an element other than carbon, for example, nitrogen, oxygen or sulfur, alone or in combination. Preferred heteroaryls contain about 5 to about 6 ring atoms. Non-limiting examples of suitable heteroaryls include pyridyl, pyrazinyl, furanyl, thienyl, pyrimidinyl, pyridine (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzo-furazanyl, indolyl, azaindolyl, benzimidazolyl, benzothienyl, quinolinyl, imidazolyl, thieno-pyridyl, quinazolinyl, thienopyrimidyl, pyrrolopyridyl, imidazopyridyl, isoquinolinyl, benzo-azaindolyl, 1,2,4-triazinyl, benzothiazolyl and the like. "Cycloalkyl" represents a non-aromatic mono- or multicyclic ring system comprising 3 to about 10 carbon atoms, preferably about 5 to about 10 carbon atoms. Preferred cycloalkyl rings contain about 5 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like. "Heterocycloalkyl" represents a non-aromatic saturated monocyclic or multicyclic ring system comprising 3 to about 10 ring atoms, preferably about 5 to about 10 ring atoms, in which one or more of the atoms in the ring system is an element other than carbon, for example, nitrogen, oxygen or sulfur, alone or in combination. Preferred heterocycloalkyls contain about 5 to about 6 ring atoms. Non-limiting examples of suitable monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Arylalkyl" represents an aryl-alkyl-group in which the aryl and alkyl are as previously described. Non-limiting examples of suitable arylalkyl groups include benzyl, 2-phenethyl and naphthalenylmethyl. In the context of the present invention, when R is arylalkyl, the bond between the arylalkyl radical and the C atom of the carboxylate group COO is through a carbon atom of the alkyl part of the arylalkyl radical. Likewise, when R is selected from "cycloalkylalkyl", "heterocycloalkylalkyl" and "heteroarylalkyl", these radicals are bound to the C atom of the carboxylate group COO via a carbon atom of their alkyl part.

In the context of the present invention, R can for instance be selected from H, —$CH_3$, —$C_2H_5$, —$C_3H_7$, —$C_4H_9$, —$C_6H_5$, —$CH_2COOH$, —$CH_2NH_2$, —$CH_2CH_2COOH$, —$CH_2CH_2Cl$, —$CH_2CH_2CH(NH_2)COOH$, -(p-$C_6H_4NH_2$), -(p-$C_6H_4NO_2$), -(p-$C_6H_4OH$) or 3-nitro-4-hydroxyphenyl. In an especially preferred embodiment, R is selected from the group consisting of H and alkyl groups containing 1 to 6 carbon atoms, preferably from H and alkyl groups containing 1 to 4 carbon atoms, more preferably from H, —CH$_3$, —C$_2$H$_5$, -nC$_3$H$_7$, -iC$_3$H$_7$ and -tC$_4$H$_9$, such as —CH$_3$.

Generally, z is ranging from 12 to 24, preferably 12, 14, 16, 18, 20, 22 or 24, more preferably 12, 16, 20 or 24, most preferably 12, 16 or 24. In particular, z is 12 or 16, more particularly 16. In another embodiment z is 12, 13, 14, 15, 16, 17, 18, 19, 20, 21, 22, 23 or 24.

The number of oxygen atoms y depends on the number z and nature of carboxylate-based groups RCOO present in the POM. In a preferred embodiment, in which the central M' is coordinated by 8 oxo anions O$^{2-}$ incorporated in the M$_{12}$-cuboctrahedron and two adjacent coordination sites of the square-planar coordination sphere of each of the 12 noble metal atoms M ('the 24 inner coordination sites') are occupied by two of said 8 oxo anions O$^{2-}$, i.e., each f said 8 oxo anions O$^{2-}$ coordinates 3 M atoms and the M' atom, each of the two remaining adjacent coordination sites of the square-planar coordination sphere of each of the 12 noble metal atoms M ('the 24 outer coordination sites') which is not occupied by carboxylate-based groups RCOO is occupied by an additional oxo anions O$^{2-}$, wherein preferably each of said additional oxo anions O$^{2-}$ independently can occupy 1, 2, 3, or 4, preferable 1 or 2, in particular only 1, of 'the 24 outer coordination sites', e.g., if 20 of 'the 24 outer coordination sites' are occupied by carboxylate-based groups RCOO, such as 8 monodentate and 6 bidentate carboxylate-based groups RCOO, the remaining 4 of 'the 24 outer coordination sites' are occupied by preferably 4 additional oxo anions O$^{2-}$, i.e., the resulting POM contains in total 12 oxo anions O$^{2-}$ with 8 oxo anions O$^{2-}$ being incorporated in the M$_{12}$-cuboctrahedron and 4 additional 'outer' oxo anions O$^{2-}$. In a more preferred embodiment all of said two remaining adjacent coordination sites of the square-planar coordination sphere of each of the 12 noble metal atoms M are occupied by carboxylate-based groups RCOO, i.e., no additional oxo anions O$^{2-}$ but only the 8 oxo anions O$^{2-}$ incorporated in the M$_{12}$-cuboctrahedron are present in the POM. In a most preferred embodiment all of said two remaining adjacent coordination sites of the square-planar coordination sphere of each of the 12 noble metal atoms M are occupied by monodentate and/or bidentate carboxylate-based groups RCOO; preferably 12 bidentate, 2 monodentate and 11 bidentate, 4 monodentate and 10 bidentate, 6 monodentate and 9 bidentate, 8 monodentate and 8 bidentate, 10 monodentate and 7 bidentate, 12 monodentate and 6 bidentate, 14 monodentate and 5 bidentate, 16 monodentate and 4 bidentate, 18 monodentate and 3 bidentate, 20 monodentate and 2 bidentate, 22 monodentate and 1 bidentate, or 24 monodentate carboxylate-based groups RCOO; more preferably 6 monodentate and 9 bidentate, 8 monodentate and 8 bidentate, 10 monodentate and 7 bidentate, 12 monodentate and 6 bidentate, 14 monodentate and 5 bidentate, 16 monodentate and 4 bidentate, or 18 monodentate and 3 bidentate carboxylate-based groups RCOO; most preferably 6 monodentate and 9 bidentate, 8 monodentate and 8 bidentate, or 10 monodentate and 7 bidentate carboxylate-based groups RCOO; in particular 8 monodentate and 8 bidentate carboxylate-based groups RCOO.

Thus, in a preferred embodiment the invention relates to a POM $(A_n)^{m+}[M'M_{12}O_y(RCOO)_zH_q]^{m-}$, wherein M is Pd$^{II}$.

Thus, in a preferred embodiment the invention relates to a POM $(A_n)^{m+}[M'M_{12}O_y(RCOO)_zH_q]^{m-}$, wherein M' is selected from the group consisting of Pd, Ga, In, Tl and Sn, in particular Pd or In or Tl, especially In.

Thus, in a preferred embodiment the invention relates to a POM $(A_n)^{m+}[M'M_{12}O_y(RCOO)_zH_q]^{m-}$, wherein R is an alkyl group or a hydrogen atom, in particular R is selected from the group consisting of H and an alkyl group containing 1 to 6 carbon atoms, more particularly from H and alkyl groups containing 1 to 4 carbon atoms, most particularly from H, —CH$_3$, —C$_2$H$_5$, -nC$_3$H$_7$, -iC$_3$H$_7$ and -tC$_4$H$_9$, especially CH$_3$.

Thus, in a preferred embodiment the invention relates to a POM $(A_n)^{m+}[M'M_{12}O_y(RCOO)_zH_q]^{m-}$, wherein M is Pd$^{II}$, M' is selected from the group consisting of Pd$^{II}$, Ga$^{III}$, In$^{III}$, Tl$^{III}$ and Sn$^{IV}$, in particular Pd$^{II}$ or In$^{III}$, especially In$^{III}$, and R is selected from the group consisting of H, —CH$_3$, —C$_2$H$_5$, -nC$_3$H$_7$, -iC$_3$H$_7$ and -tC$_4$H$_9$, especially CH$_3$.

Thus, in a preferred embodiment the invention relates to a POM $(A_n)^{m+}[M'M_{12}O_y(RCOO)_zH_q]^{m-}$, wherein M is Pd$^{II}$, M' is selected from the group consisting of Pd$^{II}$, Ga$^{III}$, In$^{III}$, Tl$^{III}$ and Sn$^{IV}$, in particular Pd$^{II}$ or In$^{III}$ or Tl$^{III}$, especially In$^{III}$, and R is selected from the group consisting of H, —CH$_3$, —C$_2$H$_5$, -nC$_3$H$_7$, -iC$_3$H$_7$ and -tC$_4$H$_9$, especially CH$_3$, wherein all M are the same.

Thus, in a preferred embodiment the invention relates to a POM $(A_n)^{m+}[M'M_{12}O_y(RCOO)_zH_q]^{m-}$, wherein M is Pd$^{II}$, M' is selected from the group consisting of Pd$^{II}$, Ga$^{III}$, In$^{III}$, Tl$^{III}$ and Sn$^{IV}$, in particular Pd$^{II}$ or In$^{III}$ or Tl$^{III}$, especially In$^{III}$, and R is selected from the group consisting of H, —CH$_3$, —C$_2$H$_5$, -nC$_3$H$_7$, -iC$_3$H$_7$ and -tC$_4$H$_9$, especially CH$_3$, and y is 8.

Thus, in a preferred embodiment the invention relates to a POM $(A_n)^{m+}[M'M_{12}O_y(RCOO)_zH_q]^{m-}$, wherein M is Pd$^{II}$, M' is selected from the group consisting of Pd$^{II}$, Ga$^{III}$, In$^{III}$, Tl$^{III}$ and Sn$^{IV}$, in particular Pd$^{II}$ or In$^{III}$ or Tl$^{III}$, especially In$^{III}$, R is selected from the group consisting of H, —CH$_3$, —C$_2$H$_5$, -nC$_3$H$_7$, -iC$_3$H$_7$ and -tC$_4$H$_9$, especially CH$_3$, and z is 16.

Thus, in a preferred embodiment the invention relates to a POM $(A_n)^{m+}[M'M_{12}O_y(RCOO)_zH_q]^{m-}$, wherein M is Pd$^{II}$, M' is selected from the group consisting of Pd$^{II}$, Ga$^{III}$, In$^{III}$, Tl$^{III}$ and Sn$^{IV}$, in particular Pd$^{II}$ or In$^{III}$ or Tl$^{III}$, especially In$^{II}$, R is selected from the group consisting of H, —CH$_3$, —C$_2$H$_5$, -nC$_3$H$_7$, -iC$_3$H$_7$ and -tC$_4$H$_9$, especially CH$_3$, y is 8, and z is 16.

Accordingly, in a preferred embodiment the invention relates to POMs represented by the formula

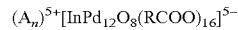
$(A_n)^{5+}[InPd_{12}O_8(RCOO)_{16}]^{5-}$ or solvates thereof, wherein R is selected from the group consisting of H, —CH$_3$, —C$_2$H$_5$, -nC$_3$H$_7$, -iC$_3$H$_7$ and -tC$_4$H$_9$, especially CH$_3$, and A and n are the same as defined above.

Further, suitable examples of POMs according to the invention are represented by the formulae

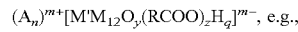
$(A_n)^{m+}[M'M_{12}O_y(RCOO)_zH_q]^{m-}$, e.g.,

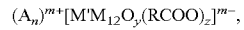
$(A_n)^{m+}[M'M_{12}O_y(RCOO)_z]^{m-}$,

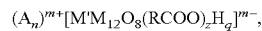
$(A_n)^{m+}[M'M_{12}O_8(RCOO)_zH_q]^{m-}$,

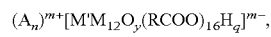
$(A_n)^{m+}[M'M_{12}O_y(RCOO)_{16}H_q]^{m-}$,

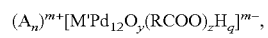
$(A_n)^{m+}[M'Pd_{12}O_y(RCOO)_zH_q]^{m-}$,

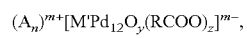
$(A_n)^{m+}[M'Pd_{12}O_y(RCOO)_z]^{m-}$,

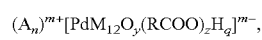
$(A_n)^{m+}[PdM_{12}O_y(RCOO)_zH_q]^{m-}$,

$(A_n)^{6+}[M'M_{12}O_y(RCOO)_zH_q]^{6-}$, or

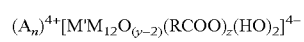
$(A_n)^{4+}[M'M_{12}O_{(y-2)}(RCOO)_z(HO)_2]^{4-}$ $(A_6)^{6+}[M'M_{12}O_y(RCOO)_z]^{6-}$, $(A_n)^{m+}[PdPd_{12}O_y(RCOO)_zH_q]^{m-}$, such as $(A_n)^{m+}[PdPd_{12}O_y(RCOO)_z]^{m-}$, $(A_n)^{m+}[PdPd_{12}O_8(RCOO)_z]^{m-}$, $(A_n)^{6+}[PdPd_{12}O_8(RCOO)_z]^{6-}$, or $(A_n)^{4+}[PdPd_{12}O_6(RCOO)_z(HO)_2]^{4-}$, $(A_6)^{6+}[PdPd_{12}O_8(RCOO)_z]^{6-}$, $(A_n)^{m+}[PdPt_{12}O_y(RCOO)_zH_q]^{m-}$, such as $(A_n)^{m+}[PdPt_{12}O_y(RCOO)_z]^{m-}$, $(A_n)^{6+}[PdPt_{12}O_8(RCOO)_z]^{6-}$, or $(A_n)^{4+}[PdPt_{12}O_6(RCOO)_z(HO)_2]^{4-}$, $(A_6)^{6+}[PdPt_{12}O_8(RCOO)_z]^{6-}$, $(A_n)^{m+}[GaPd_{12}O_y(RCOO)_zH_q]^{m-}$, such as $(A_n)^{m+}[GaPd_{12}O_y(RCOO)_z]^{m-}$, $(A_n)^{m+}[GaPd_{12}O_8(RCOO)_z]^{m-}$, $(A_n)^{7+}[GaPd_{12}O_8(RCOO)_z]^{7-}$, or $(A_n)^{5+}[GaPd_{12}O_6(RCOO)_z(HO)_2]^{5-}$, $(A_7)^{7+}[GaPd_{12}O_8(RCOO)_z]^{7-}$, $(A_n)^{m+}[InPd_{12}O_y(RCOO)_zH_q]^{m-}$, such as $(A_n)^{m+}[InPd_{12}O_y(RCOO)_z]^{m-}$, $(A_n)^{m+}[InPd_{12}O_8(RCOO)_z]^{m-}$, $(A_n)^{7+}[InPd_{12}O_8(RCOO)_z]^{7-}$, or $(A_n)^{5+}[InPd_{12}O_6(RCOO)_z(HO)_2]^{5-}$, $(A_7)^{7+}[InPd_{12}O_8(RCOO)_z]^{7-}$, $(A_n)^{m+}[TlPd_{12}O_y(RCOO)_zH_q]^{m-}$, such as $(A_n)^{m+}[TlPd_{12}O_y(RCOO)_z]^{m-}$, $(A_n)^{m+}[TlPd_{12}O_8(RCOO)_z]^{m-}$, $(A_n)^{7+}[TlPd_{12}O_8(RCOO)_z]^{7-}$, or $(A_n)^{5+}[TlPd_{12}O_6(RCOO)_z(HO)_2]^{5-}$, $(A_7)^{7+}[TlPd_{12}O_8(RCOO)_z]^{7-}$, $(A_n)^{m+}[PdAu_{12}O_y(RCOO)_zH_q]^{m-}$, such as $(A_n)^{m+}[PdAu_{12}O_y(RCOO)_z]^{m-}$, $(A_n)^{m+}[PdAu_{12}O_8(RCOO)_z]^{m-}$, $(A_n)^{18+}[PdAu_{12}O_8(RCOO)_z]^{18-}$, or $(A_n)^{16+}[PdAu_{12}O_6(RCOO)_z(HO)_2]^{16-}$, $(A_{18})^{18+}[PdAu_{12}O_8(RCOO)_z]^{18-}$, $(A_n)^{m+}[M'Pd_{12}O_y(RCOO)_{16}H_q]^{m-}$, such as $(A_n)^{m+}[M'Pd_{12}O_y(RCOO)_{16}]^{m-}$, $(A_n)^{m+}[M'Pd_{12}O_8(RCOO)_{16}]^{m-}$, $(A_n)^{6+}[M'Pd_{12}O_8(RCOO)_{16}]^{6-}$, or $(A_n)^{4+}[M'Pd_{12}O_6(RCOO)_{16}(HO)_2]^{4-}$, $(A_6)^{6+}[M'Pd_{12}O_8(RCOO)_{16}]^{6-}$, $(Na_6)^{6+}[M'Pd_{12}O_y(RCOO)_z]^{6-}$, or $(Na_4)^{4+}[M'Pd_{12}O_{(y-2)}(RCOO)_z(HO)_2]^{-4}$, $(K_6)^{6+}[M'Pd_{12}O_y(RCOO)_z]^{6-}$, or $(K_4)^{4+}[M'Pd_{12}O_{(y-2)}(RCOO)_z(HO)_2]^{-4}$, $(K_6)^{6+}[M'Pt_{12}O_y(RCOO)_z]^{6-}$, or $(K_4)^{4+}[M'Pt_{12}O_{(y-2)}(RCOO)_z(HO)_2]^{4-}$, $(A_6)^{6+}[M'Pd_{12}O_y(RCOO)_z]^{6-}$, or $(A_4)^{4+}[M'Pd_{12}O_{(y-2)}(RCOO)_z(HO)_2]^{4-}$, $(A_n)^{6+}[M'Pd_{12}O_8(RCOO)_z]^{6-}$, or $(A_n)^{4+}[M'Pd_{12}O_6(RCOO)_z(HO)_2]^{4-}$, $(A_n)^{5+}[GaPd_{12}O_8(RCOO)_z]^{5-}$, or $(A_n)^{5+}[GaPd_{12}O_6(RCOO)_z(HO)_2]^{5-}$, $(A_n)^{5+}[InPd_{12}O_8(RCOO)_z]^{5-}$, or $(A_n)^{5+}[InPd_{12}O_6(RCOO)_z(HO)_2]^{5-}$, $(A_n)^{5+}[TlPd_{12}O_8(RCOO)_z]^{5-}$, or $(A_n)^{5+}[TlPd_{12}O_6(RCOO)_z(HO)_2]^{5-}$, $(A_n)^{6+}[PdPd_{12}O_8(RCOO)_z]^{6-}$, or $(A_n)^{4+}[PdPd_{12}O_6(RCOO)_z(HO)_2]^{4-}$, preferably wherein R is selected from the group consisting of H, —CH$_3$, —C$_2$H$_5$, -nC$_3$H$_7$, -iC$_3$H$_7$ and -tC$_4$H$_9$, and $(A_6)^{6+}[PdPd_{12}O_8(H_3CCOO)_{16}]^{6-}$, such as $(K_6)^{6+}[PdPd_{12}O_8(H_3CCOO)_{16}]^{6-}$, or $(A_4)^{4+}[PdPd_{12}O_8(H_3CCOO)_{16}(HO)_2]^{4-}$, such as $(K_4)^{4+}[PdPd_{12}O_8(H_3CCOO)_{16}(HO)_2]^{4-}$, $(A_6)^{6+}[PdPt_{12}O_8(H_3CCOO)_{16}]^{6-}$, such as $(K_6)^{6+}[PdPt_{12}O_8(H_3CCOO)_{16}]^{6-}$, or $(A_4)^{4+}[PdPt_{12}O_8(H_3CCOO)_{16}(HO)_2]^{4-}$, such as $(K_4)^{4+}[PdPt_{12}O_8(H_3CCOO)_{16}(HO)_2]^{4-}$, $(A_7)^{5+}[GaPd_{12}O_8(H_3CCOO)_{16}]^{5-}$, such as $(K_7)^{5+}[GaPd_{12}O_8(H_3CCOO)_{16}]^{5-}$, or $(A_7)^{5+}[InPd_{12}O_8(H_3CCOO)_{16}]^{5-}$, such as $(K_7)^{5+}[InPd_{12}O_8(H_3CCOO)_{16}]^{5-}$, or $(A_7)^{5+}[TlPd_{12}O_8(H_3CCOO)_{16}]^{5-}$, such as $(K_7)^{5+}[TlPd_{12}O_8(H_3CCOO)_{16}]^{5-}$, or $(A_5)^{5+}[PdPd_{12}O_8(H_3CCOO)_{16}(HO)_2]^{5-}$, such as $(K_5)^{5+}[PdPd_{12}O_8(H_3CCOO)_{16}(HO)_2]^{5-}$, $(A_7)^{7+}[AuPd_{12}O_8(H_3CCOO)_{16}]^{7-}$, such as $(K_7)^{7+}[AuPd_{12}O_8(H_3CCOO)_{16}]^{7-}$, or $(A_5)^{5+}[AuPd_{12}O_8(H_3CCOO)_{16}(HO)_2]^{5-}$, such as $(K_5)^{5+}[AuPd_{12}O_8(H_3CCOO)_{16}(HO)_2]^{5-}$, $(A_7)^{5+}[InPt_{12}O_8(H_3CCOO)_{16}]^{5-}$, such as $(K_7)^{5+}[InPt_{12}O_8(H_3CCOO)_{16}]^{5-}$, or $(A_5)^{5+}[PtPd_{12}O_8(H_3CCOO)_{16}(HO)_2]^{5-}$, such as $(K_5)^{5+}[PtPd_{12}O_8(H_3CCOO)_{16}(HO)_2]^{5-}$, $(InA_3)^{6+}[PdPd_{12}O_8(H_3CCOO)_{16}]^{6-}$, such as $(InK_3)^{6+}[PdPd_{12}O_8(H_3CCOO)_{16}]^{6-}$, or $(InA)^{4+}[PdPd_{12}O_8(H_3CCOO)_{16}(HO)_2]^{4-}$, such as $(InK)^{4+}[PdPd_{12}O_8(H_3CCOO)_{16}(HO)_2]^{4-}$.

The invention also includes solvates of the present POMs. A solvate is an association of solvent molecules with a POM. Preferably, water is associated with the POMs and thus, the POMs according to the invention can in particular be represented by the formulae $(A_n)^{m+}[M'M_{12}O_y(RCOO)_zH_q]^{m-}\cdot wH_2O$, e.g., $(A_n)^{m+}[M'M_{12}O_y(RCOO)_z]^{m-}\cdot wH_2O$, or $(A_n)^{m+}[M'M_{12}O_{(y-q)}(RCOO)_z(HO)q]^{m-}\cdot wH_2O$, such as $(A_n)^{m+}[M'M_{12}O_{(8-q)}(RCOO)_z(HO)q]^{m-}\cdot wH_2O$ and $(A_n)^{m+}[M'M_{12}O_{(y-q)}(RCOO)_{16}(HO)q]^{m-}\cdot wH_2O$, wherein
A, n, m, M, M', y, R, z and q are the same as defined above, and
w represents the number of attracted water molecules per polyanion and mostly depends on the type of cations A. In some embodiments w is an integer from 1 to 100, preferably 1 to 80, more preferably 10 to 60, most preferably 20 to 50 such as 20 or 30.

Suitable examples of the POM solvates according to the invention are represented by the formulae $(A_n)^{m+}[M'M_{12}O_y(RCOO)_zH_q]^{m-}\cdot wH_2O$, e.g., $(A_n)^{m+}[M'M_{12}O_y(RCOO)_z]^{m-}\cdot wH_2O$, $(A_n)^{m+}[M'M_{12}O_8(RCOO)_zH_q]^{m-}\cdot wH_2O$, $(A_n)^{m+}[M'M_{12}O_y(RCOO)_{16}H_q]^{m-}\cdot wH_2O$, $(A_n)^{m+}[M'Pd_{12}O_y(RCOO)_zH_q]^{m-}\cdot wH_2O$, $(A_n)^{m+}[M'Pd_{12}O_y(RCOO)_z]^{m-}\cdot wH_2O$, $(A_n)^{m+}[PdM_{12}O_y(RCOO)_zH_q]^{m-}\cdot wH_2O$, $(A_n)^{6+}[M'M_{12}O_y(RCOO)_zH_q]^{6-}\cdot wH_2O$, or $(A_n)^{4+}[M'M_{12}O_{(y-2)}(RCOO)_z(HO)_2]^{4-}\cdot wH_2O$, $(A_6)^{6+}[M'M_{12}O_y(RCOO)_z]^{6-}\cdot wH_2O$, $(A_n)^{m+}[PdPd_{12}O_y(RCOO)_zH_q]^{m-}\cdot wH_2O$, such as $(A_n)^{m+}[PdPd_{12}O_y(RCOO)_z]^{m-}\cdot wH_2O$, $(A_n)^{m+}[PdPd_{12}O_8(RCOO)_z]^{m-}\cdot wH_2O$, $(A_n)^{6+}[PdPd_{12}O_8(RCOO)_z]^{6-}\cdot wH_2O$, or $(A_n)^{4+}[PdPd_{12}O_6(RCOO)_z(HO)_2]^{4-}\cdot wH_2O$, $(A_6)^{6+}[PdPd_{12}O_8(RCOO)_z]^{6-}\cdot wH_2O$, $(A_n)^{m+}[InPd_{12}O_y(RCOO)_zH_q]^{m-}\cdot wH_2O$, such as $(A_n)^{m+}[InPd_{12}O_y(RCOO)_z]^{m-}\cdot wH_2O$, $(A_n)^{m+}[InPd_{12}O_8(RCOO)_z]^{m-}\cdot wH_2O$, $(A_n)^{5+}[InPd_{12}O_8(RCOO)_z]^{5-}\cdot wH_2O$, or $(A_n)^{3+}[InPd_{12}O_6(RCOO)_z(HO)_2]^{3-}\cdot wH_2O$, $(A5)^{5+}[InPd_{12}O_8(RCOO)_z]^{5-}\cdot wH_2O$, preferably wherein R is selected from the group consisting of H, —$CH_3$, —$C_2H_5$, -n$C_3H_7$, -i$C_3H_7$ and -t$C_4H_9$, $(A_6)^{6+}[PdPd_{12}O_8(H_3CCOO)_{16}]^{6-}\cdot wH_2O$, such as $(K_6)^{6+}[PdPd_{12}O_8(H_3CCOO)_{16}]^{6-}\cdot 30H_2O$, or $(A_4)^{4+}[PdPd_{12}O_8(H_3CCOO)_{16}(HO)_2]^{4-}\cdot wH_2O$, such as $(K_4)^{4+}[PdPd_{12}O_8(H_3CCOO)_{16}(HO)_2]^{-}4\cdot 30H_2O$, $(A_6)^{6+}[PdPt_{12}O_8(H_3CCOO)_{16}]^{6-}\cdot wH_2O$, such as $(K_6)^{6+}[PdPt_{12}O_8(H_3CCOO)_{16}]^{6-}\cdot 30H_2O$, or $(A_4)^{4+}[PdPt_{12}O_8(H_3CCOO)_{16}(HO)_2]^{4-}\cdot wH_2O$, such as $(K_4)^{4+}[PdPt_{12}O_8(H_3CCOO)_{16}(HO)_2]^{-}4\cdot 30H_2O$, or $(A_5)^{5+}[InPd_{12}O_8(H_3CCOO)_{16}]^{5-}\cdot wH_2O$, such as $(K_5)^{5+}[InPd_{12}O_8(H_3CCOO)_{16}]^{5-}\cdot 20H_2O$, or $(A_3)^{3+}[InPd_{12}O_8(H_3CCOO)_{16}(HO)_2]^{3-}\cdot wH_2O$, such as $(K_3)3+[InPd_{12}O_8(H_3CCOO)_{16}(HO)_2]^{3-}\cdot 20H_2O$.

In a preferred embodiment, water molecules, if present at all, are coordinated to protons and/or A cations, while the M and M' cations are not coordinated by water. In a preferred embodiment, a proportion of the water molecules is not directly attached to the POM framework $(A_n)^{m+}[M'M_{12}O_y(RCOO)_zH_q]^{m-}$ by coordination, but rather indirectly by hydrogen-bonding as water of crystallization. Thus, in a preferred embodiment, the attracted water molecules, if present at all, are coordinated to A cations and/or possibly exhibit weak interactions by hydrogen bonding to protons of the POM and/or the attracted water molecules, if present at all, are water of crystallization.

The invention also includes the present POMs or solvates thereof further associated with optional co-crystallizing entities such as RCOO salts. For instance, if the POMs are synthesized in the presence of a source of Pd, a source of K and a $H_3CCOO$-containing starting material, the resulting POMs may be associated with co-crystallizing entities such as $K^+(H_3CCOO)^-$ and/or $K_2^{2+}[Pd(H_3CCOO)_4]^{2-}$ and/or $Pd(H_3CCOO)_2$.

The guest atom M' cannot be replaced or removed without destroying the structural framework of the polyanion, once the polyanion framework is formed.

In another embodiment, the POMs may be further calcined at a temperature not exceeding the transformation temperature of the POM, i.e., the temperature at which decomposition of the POM starts to take place (usually about 150-180° C. for the present POMs according to their corresponding TGA). Thus, in a preferred embodiment the POMs of the present invention are thermally stable up to temperatures of around 150-180° C. Without being bound by any theory, it is believed that below 150-180° C. the POMs according to the present invention only loose water of crystallization present in the POM without affecting the structural integrity of the POM framework. For the calcination, common equipment may be used, that is commercially available. Calcination of the POMs may be conducted under an oxygen containing gas such as air, under vacuum, under hydrogen or under an inert gas such as argon or nitrogen, preferably under an oxygen containing gas such as air or an inert gas such as nitrogen, more preferably in air. Calcination may help to activate a POM pre-catalyst by forming active sites. Upon heating, POM salts first loose water molecules (of water of crystallization) and then organic groups (if present) before they start to transform/decompose, e.g., by oxidation. TGA can be used to study the weight loss of the POM salts, and Differential Scanning Calorimetry (DSC) indicates if each step is endo- or exothermic. Such measurements may be carried out, e.g., under nitrogen gas, air, oxygen or hydrogen.

In many cases, however, and in particular if the POM is used as a catalyst or pre-catalyst under reductive conditions, drying of the POM without calcination may be sufficient. In other cases calcination might significantly improve the catalytic performance of the POMs according the present invention.

In a further embodiment, the POMs may be calcined at a temperature exceeding the transformation temperature of the POM, i.e., the temperature at which decomposition of the POM starts to take place (usually about 150-180° C. for the present POMs according to their corresponding TGA). Without being bound by any theory, it is believed that calcination of the POMs according to the present invention at a temperature exceeding the transformation temperature of the POM, i.e., above 180° C., and below 800° C. is accompanied by the loss of carboxylate-based capping groups RCOO, as is evident from their corresponding TGA. The removal of carboxylate-based capping groups RCOO from the POMs of the present invention increases the accessibility of the noble metal atoms and thus is in many cases a suitable measure to specifically enhance or enable their catalytic activity.

Hence, the POMs of the present invention allow for their carboxylate-based capping groups RCOO to be removed under acceptably mild conditions which in turn provides for the possibility to efficiently and mildly derivatise or convert them in general, and more specifically to activate them in order to enhance or enable their catalytic activity.

In contrast, the corresponding related POMs known in the art comprising capping groups being based on P, As, or Se, are in general stable up to a temperature of about 600-700° C. Thus, the capping groups being based on P, As, or Se can only be removed under exceptionally harsh conditions. Also as opposed to the corresponding related POMs known in the art comprising capping groups being based on P, As, or Se, the capping carboxylate-based capping groups RCOO of the POMs of the present invention can also be removed under rather mild conditions by oxidation of the RCOO group and/or acidification, i.e., protonation of the RCOO group.

In general, it has been found that the removal of the carboxylate-based capping groups RCOO according to the present invention can be accomplished under far milder conditions, e.g., at lower temperatures, as compared to the removal of capping groups known in the art being based on P, As, or Se.

In conclusion, as opposed to the POMs known in the art, i.e., highly symmetrical POMs comprising capping groups being solely based on P, As, or Se, and structurally distorted POMs comprising a minor proportion of carboxylate-based capping groups, the inventors surprisingly found that sufficiently stable noble metal-rich POMs maintaining the structural integrity of the unique highly symmetrical structural arrangement with the 'inner' $MO_8$/M' 8 motif and the surrounding cuboctahedral $M_{12}$-motif, can also be obtained without P, As or Se-based capping groups, but by using the carboxylate-based capping groups RCOO according to the present invention. However, despite their sufficient stability, e.g., thermal stability of up to about 180° C., permitting their use under a variety of reaction conditions, the POMs of the present invention can be further derivatised or converted, e.g., activated in order to enhance or enable their catalytic activity, under also acceptably mild conditions. Consequently, the POMs of the present invention provide an exceptionally desirable balance between stability and convertibility.

The invention is further directed to a process for preparing POMs according to the invention. A process for preparing POMs according to the present invention comprises:

(a) reacting at least one source of M and at least one source of M' with at least one RCOO-containing starting material to form a salt of the polyanion $[M'M_{12}O_y(RCOO)_zH_q]$ or a solvate thereof, (b) optionally adding at least one salt of A to the reaction mixture of step (a) to form a POM of formula $(A_n)^{m+}[M'M_{12}O_y(RCOO)_zH_q]^{m-}$ or a solvate thereof, and (c) recovering the POM or solvate thereof, wherein A, n, m, M, M', y, R, z and q are the same as defined above.

In step (a) of said process at least one source of M' is used, especially one source of M'. Generally, in a preferred embodiment of the present invention, salts of the following metals Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg, lanthanide metal, Ga, In, Tl, Ge, Sn, Pb, Sb, and Bi such as chlorides, fluorides, hydroxides, nitrates, acetates and/or sulfates can be used as source for M'. More preferably, if M' is a noble metal selected from the group consisting of Pd, Pt, Rh, Ir, Ag and Au, $Pd^{II}$ salts such as $PdCl_2$, $Pd(NO_3)_2$, $Pd(CH_3COO)_2$ and $PdSO_4$; $Pt^{II}$ salts such as $PtCl_2$; $Rh^I$ salts such as $[(C_6H_5)_3P]_2RhCl(CO)$ and $[Rh(CO)_2Cl]_2$; $Ir^I$ salts such as $[(C_6H_5)_3P]_2IrCl(CO)$; $Au^{III}$ salts such as $AuCl_3$, $Au(OH)_3$ and $HAuCl_4$.aq; and $Ag^{III}$ salts preferably generated with oxidizing reagents from $Ag^I$ salts such as $AgNO_3$, AgF and AgCl can be used as source for the noble metal M' atoms. More preferably, if M' is Ga, $GaCl_3$, $Ga(CH_3COO)_3$, $GaBr_3$, and/or $Ga(NO_3)_3$ are used; if M' is In, $InCl_3$, $In(CH_3COO)_3$, $InBr_3$, and/or $In(NO_3)_3$ are used; if M' is Tl, $TlCl_3$, $Tl(CH_3COO)_3$, $TlBr_3$, and/or $Tl(NO_3)_3$ are used; if M' is Sn, $SnCl_4$, $Sn(CH_3COO)_4$, $SnBr_4$, and/or $Sn(NO_3)_4$ are used; if M' is Ge, $GeCl_4$ is used; if M' is Pb, $PbCl_4$ and/or Pb(CH$_3$COO)$_4$ are used; if M' is Bi, BiCl$_3$, Bi(NO$_3$)$_3$ and/or BiBr$_3$ are used; if M' is Sb, SbCl$_5$ and/or Sb(CH$_3$COO)$_3$ are used. Most preferably, M' is Pd and the Pd source is Pd(CH$_3$COO)$_2$ or M' is In and the In source is In(NO$_3$)$_3$.

In step (a) of said process at least one source of M is used, especially one source of M. Generally, in a preferred embodiment of the present invention, Pd$^{II}$ salts such as PdCl$_2$, Pd(NO$_3$)$_2$, Pd(CH$_3$COO)$_2$ and PdSO$_4$; Pt$^{II}$ salts such as PtCl$_2$; Rh$^I$ salts such as [(C$_6$H$_5$)$_3$P]$_2$RhCl(CO) and [Rh(CO)$_2$Cl]$_2$; Ir$^I$ salts such as [(C$_6$H$_5$)$_3$P]$_2$IrCl(CO); Au$^{III}$ salts such as AuCl$_3$, Au(OH)$_3$ and HAuCl$_4$.aq; and Ag$^{III}$ salts preferably generated with oxidizing reagents from Ag$^I$ salts such as AgNO$_3$, AgF and AgCl can be used as source for the noble metal M atoms. More preferably, the Pd$^{II}$ source is PdCl$_2$ or Pd(CH$_3$COO)$_2$ and the Pt$^{II}$ source is PtCl$_2$. Most preferably, M is Pd and the Pd source is Pd(CH$_3$COO)$_2$.

In step (a) of said process the metal source or metal sources are reacted with at least one RCOO-containing starting material. For instance, a water-soluble carboxylic acid or preferably a salt thereof may be used as RCOO-containing starting material. It is also possible to use a water-soluble carboxylic acid ester which hydrolyses under the reaction conditions. In one embodiment of the present invention, suitable examples of RCOO-containing starting materials include HCOOH or a salt thereof; or alkyl-COOH or a salt thereof, in particular a C$_1$-C$_6$ alkyl-COOH or a salt thereof, more particularly a C$_1$-C$_4$ alkyl-COOH or a salt thereof, such as H$_3$CCOOH, H$_3$C(H$_2$C)COOH, H$_3$C(H$_2$C)$_2$COOH, H$_3$C(H$_2$C)$_3$COOH, (H$_3$C)$_2$(HC)COOH, (H$_3$C)$_3$CCOOH, or a salt thereof. In a preferred embodiment of the present invention, the RCOO-containing starting material is in the form of a salt such as the Li salt, Na salt, K salt, Mg salt or mixtures thereof, for instance K salt. In an especially preferred embodiment of the present invention the RCOO-containing starting material is any salt or derivative of H$_3$CCOO$^-$, such as Li(H$_3$CCOO), Na(H$_3$CCOO), K(H$_3$CCOO), Mg(H$_3$CCOO)$_2$ or mixtures thereof, preferably Li(H$_3$CCOO), Na(H$_3$CCOO), K(H$_3$CCOO), or mixtures thereof, and most preferably Na(H$_3$CCOO), K(H$_3$CCOO), or mixtures thereof, in particular K(H$_3$CCOO). In an especially preferred embodiment, the noble metal M source, preferably Pd(CH$_3$COO)$_2$, is reacted with K(H$_3$CCOO). In a further preferred embodiment, the noble metal M source, preferably Pd(CH$_3$COO)$_2$, and the source of M', preferably Pd(CH$_3$COO)$_2$, are reacted with K(H$_3$CCOO).

In a preferred embodiment, step (a) of said process is carried out in an aqueous solution. If the RCOO-containing starting material has only a low solubility in water (for example, because of the nature of the group R) it is possible to dissolve the RCOO-containing starting material in a small volume of organic solvent and then adding this solution to an aqueous solution of the sources of M and M' or vice versa. Examples of suitable organic solvents include, but are not limited to acetonitrile, acetone, toluene, DMF, DMSO, ethanol, methanol, n-butanol, sec-butanol, isobutanol and mixtures thereof. It is also possible to use emulsifying agents to allow the reagents of step (a) of said process to undergo a reaction.

Furthermore, in a preferred embodiment of the present invention, in step (a) of said process, the concentration of the noble metal ions originating from the at least one source of M ranges from 0.005 to 5 mole/l, preferably from 0.01 to 1 mole/l, more preferably from 0.05 to 0.5 mole/l, the concentration of the metal ions originating from the at least one source of M' ranges from 0.0005 to 0.5 mole/i, preferably 0.001 to 0.5 mole/l, more preferably 0.005 to 0.2 mole/l, and the concentration of the at least one RCOO-containing starting material ranges from 0.0005 to 5 mole/l, preferably 0.001 to 1 mole/l, more preferably 0.005 to 0.75 mole/l, with the proviso that, when M is different from M', the ratio of the molar concentration of the metal ions originating from the at least one source of M to the molar concentration of the metal ions originating from the at least one source of M' is in the range from 0.1 to 50, preferably from 1 to 20, more preferably from 1 to 10, in particular 1, 2, 3, 5, or 10.

Furthermore, in a preferred embodiment, the pH of the aqueous solution in step (a) of said process ranges from 2 to 14, preferably from 4 to 12 and more preferably from 5 to 10. Most preferably, the pH is from about 6 to about 9, for instance from about 6.5 to about 7.5. Generally, in a preferred embodiment of the present invention a buffer solution can be used for maintaining the pH value in a certain range.

In a preferred embodiment of the present invention the buffer is a carboxylate-based or at least a carboxylate-containing buffer, i.e., a RCOO-containing buffer, preferably from a RCOO-containing starting material, e.g., HCOOH or a salt thereof; or alkyl-COOH or a salt thereof, in particular a C$_1$-C$_6$ alkyl-COOH or a salt thereof, more particularly a C$_1$-C$_4$ alkyl-COOH or a salt thereof, such as H$_3$CCOOH, H$_3$C(H$_2$C)COOH, H$_3$C(H$_2$C)$_2$COOH, H$_3$C(H$_2$C)$_3$COOH, (H$_3$C)$_2$(HC)COOH, (H$_3$C)$_3$CCOOH, or a salt thereof. In a preferred embodiment of the present invention the carboxylate-based buffer is a RCOO-containing buffer derived from RCOOH, a salt thereof or mixtures thereof. In a more preferred embodiment of the present invention the carboxylate-based buffer is a RCOO-containing buffer derived from Na(RCOO) or K(RCOO), such as Na(HCOO) or K(HCOO), Na(CH$_3$COO) or K(CH$_3$COO), Na(H$_3$C(H$_2$C)COO) or K(H$_3$C(H$_2$C)COO), Na(H$_3$C(H$_2$C)$_2$COO) or K(H$_3$C(H$_2$C)$_2$COO), Na(H$_3$C(H$_2$C)$_3$COO) or K(H$_3$C(H$_2$C)$_3$COO), Na((H$_3$C)$_2$(HC)COO) or K((H$_3$C)$_2$(HC)COO), and Na((H$_3$C)$_3$CCOO) or K((H$_3$C)$_3$CCOO). In a most preferred embodiment of the present invention the carboxylate-based buffer is an acetate buffer derived from any salt or derivative of H$_3$CCOO$^-$, such as Li(H$_3$CCOO), Na(H$_3$CCOO), K(H$_3$CCOO), Mg(H$_3$CCOO)$_2$ or mixtures thereof, preferably Li(H$_3$CCOO), Na(H$_3$CCOO), K(H$_3$CCOO), or mixtures thereof, and most preferably Na(H$_3$CCOO), K(H$_3$CCOO), or mixtures thereof, in particular K(H$_3$CCOO).

In another embodiment of the present invention the buffer is a phosphate buffer, preferably derived from H$_3$PO$_4$, NaH$_2$PO$_4$, Na$_2$HPO$_4$, Na$_3$PO$_4$, KH$_2$PO$_4$, K$_2$HPO$_4$, K$_3$PO$_4$, NaKHPO$_4$, NaK$_2$PO$_4$, Na$_2$KPO$_4$ or mixtures thereof, preferably H$_3$PO$_4$, NaH$_2$PO$_4$, Na$_2$HPO$_4$, Na$_3$PO$_4$ or mixtures thereof, and most preferably NaH$_2$PO$_4$, Na$_2$HPO$_4$ or mixtures thereof, in particular NaH$_2$PO$_4$. It is preferred to have either a phosphate or an acetate buffer, whereas it is less preferred to have a mixture of phosphate and acetate buffer. In a preferred embodiment of the present invention said phosphate buffer is preferably derived from NaH$_2$PO$_4$, whereas said acetate buffer is preferably derived from K(CH$_3$COO). In a very preferred embodiment of the present invention the buffer is an acetate buffer, most preferably derived from K(CH$_3$COO).

Generally, in a preferred embodiment of the present invention, additional base solution or acid solution can be used for adjusting the pH to a certain value. It is particularly preferred to use aqueous sodium hydroxide or H$_2$SO$_4$ solution having a concentration of 1 M. In another embodiment, the concentration of the aqueous base or acid solution (preferably aqueous sodium hydroxide or H$_2$SO$_4$ solution) is from 0.1 to 12 M, preferably 0.2 to 8 M, more preferably from 0.5 to 6 M, most preferably about 1 M. Generally, in a very preferred embodiment of the present invention additional base solution can be used for adjusting the pH to a certain pH value. It is particularly preferred to use aqueous sodium hydroxide solution having a concentration of 1 M. In another embodiment, the concentration of the aqueous base solution (preferably aqueous sodium hydroxide solution) is from 0.1 to 12 M, preferably 0.2 to 8 M, more preferably from 0.5 to 6 M, most preferably about 1 M.

In the context of the present invention the pH of the aqueous solution in step (a) of said process refers to the pH as measured at the end of the reaction. In the preferred embodiment where, e.g., an aqueous sodium hydroxide solution is used for adjusting the pH-value, the pH is measured after the adjustment at the end of the reaction. pH values are at 20° C., and are determined to an accuracy of ±0.05 in accordance with the IUPAC Recommendations 2002 (R. P. Buck et al., Pure Appl. Chem., Vol. 74, No. 11, pp. 2169-2200, 2002).

A suitable and commercially available instrument for pH measurement is the Mettler Toledo FE20 pH meter. The pH calibration is carried out as 2-point calibration using a pH=4.01 standard buffer solution and a pH=7.00 standard buffer solution. The resolutions are: 0.01 pH; 1 mV; and 0.1° C. The limits of error are: ±0.01 pH; ±1 mV; and ±0.5° C.

A very preferred embodiment of the present invention is said process, wherein in step (a) the at least one source of M, the at least one source of M', and the at least one source of RCOO-containing starting material are dissolved in a solution of buffer, preferably an 0.1 to 1.0 M buffer solution, in particular a 0.25 to 0.75 M buffer solution, and most preferred a 0.5 M buffer solution.

Another very preferred embodiment of the present invention is said process, wherein in step (a) the buffer already comprises the RCOO-containing starting material and no other RCOO-containing starting material than the buffer is used in step (a). In this embodiment the buffer is most preferably a carboxylate-based buffer, wherein said carboxylate-based buffer is derived from a RCOO-containing starting material, e.g., HCOOH or a salt thereof; or alkyl-COOH or a salt thereof, in particular a $C_1$-$C_6$ alkyl-COOH or a salt thereof, more particularly a $C_1$-$C_4$ alkyl-COOH or a salt thereof, such as $H_3CCOOH$, $H_3C(H_2C)COOH$, $H_3C(H_2C)_2COOH$, $H_3C(H_2C)_3COOH$, $(H_3C)_2(HC)COOH$, $(H_3C)_3CCOOH$, or a salt thereof. In a preferred embodiment of the present invention the carboxylate-based buffer is a RCOO-containing buffer derived from Na(RCOO) or K(RCOO), such as Na(HCOO) or K(HCOO), Na($CH_3COO$) or K($CH_3COO$), Na($H_3C(H_2C)COO$) or K($H_3C(H_2C)$ COO), Na($H_3C(H_2C)_2COO$) or K($H_3C(H_2C)_2COO$), Na($H_3C(H_2C)_3COO$) or K($H_3C(H_2C)_3COO$), Na(($H_3C)_2$ (HC)COO) or K(($H_3C)_2$(HC)COO), and Na(($H_3C)_3CCOO$) or K(($H_3C)_3CCOO$). In a more preferred embodiment of the present invention the carboxylate-based buffer is an acetate buffer derived from any salt or derivative of $H_3CCOO^-$, such as Li($H_3CCOO$), Na($H_3CCOO$), K($H_3CCOO$), Mg($H_3CCOO)_2$ or mixtures thereof, preferably Li($H_3CCOO$), Na($H_3CCOO$), K($H_3CCOO$), or mixtures thereof, and most preferably Na($H_3CCOO$), K($H_3CCOO$), or mixtures thereof, in particular K($H_3CCOO$).

By using a buffer, which comprises the RCOO-containing starting material, the number of reagents and substrates required in the preparation of the respective POMs is reduced and thus the synthesis is rendered more efficient and less expensive.

In step (a) of the process of the present invention, the reaction mixture is typically heated to a temperature of from 20° C. to 100° C., preferably from 30° C. to 90° C., preferably from 40° C. to 80° C., preferably from 45° C. to 70° C., and most preferably from 50° C. to 60° C.

In step (a) of the process of the present invention, the reaction mixture is typically heated for about 10 min to about 4 h, more preferably for about 30 min to 3 h, most preferably for about 120 min. Further, it is preferred that the reaction mixture is stirred during step (a).

With regard to the present invention the term crude mixture relates to an unpurified mixture after a reaction step and is thereby used synonymously with reaction mixture of the preceding reaction step.

In a preferred embodiment of the process of the present invention, between step (a) and (b), the crude mixture is filtered. Preferably, the crude mixture is filtered immediately after the end of step (a), i.e., immediately after the stirring is turned off, and is then optionally cooled. Alternatively, if applicable the heated crude mixture is cooled first, preferably to room temperature, and subsequently filtered. The purpose of this filtration is to remove solid impurities after step (a). Thus, the product of step (a) remains in the filtrate.

In a preferred embodiment, in case cation A is not present in the crude mixture or filtrate already, or the concentration of A in the crude mixture or filtrate should be increased, in step (b) of the process, a salt of the cation A can be added to the reaction mixture of step (a) of the process or to its corresponding filtrates to form $(A_n)^{m+}[M'M_{12}O_y(RCOO)_zH_q]^{m-}$. Preferably, the salt of A is added as a solid or in the form of an aqueous solution. The counterions of A can be selected from the group consisting of any stable, non-reducing, water-soluble anion, e.g., halides, nitrate, sulfate, acetate, phosphate. Preferably, the acetate or phosphate salt is used. However, the addition of extra cations A in step (b) of the process is not necessary if the desired cations are already present during step (a) of the process, for example, as a component of the buffer preferably used as solvent in step (a) of the process or a component of any of the sources of RCOO, M and/or M' including, for example, palladium and platinum cations themselves. Preferably, all desired cations are already present during step (a) of the process, thus, that there is no optional addition of extra cations necessary.

Another very preferred embodiment of the present invention is said process, wherein in step (a) the buffer already comprises the cations A. A further even more preferred embodiment of the present invention is said process, wherein in step (a) the buffer already comprises the RCOO-containing starting material and the cations A.

By using a buffer, which comprises the RCOO-containing starting material and/or the cations A, the number of reagents and substrates required in the preparation of the respective POMs is reduced and thus the synthesis is rendered more efficient and less expensive.

In step (c) of the process of the present invention, the POMs according to the invention or solvate thereof, formed in step (a) or (b) of said process, are recovered. For example, isolation of the POMs or solvate thereof can be effected by common techniques including bulk precipitation or crystallization. In a preferred embodiment of the present invention the POMs are isolated as crystalline or amorphous solids, preferably as crystalline solids. Crystallization or precipitation can be effected by common techniques such as evaporation or partial evaporation of the solvent, cooling, change of solvent, solvents or solvent mixtures, addition of crystallization seeds, etc. In a preferred embodiment the addition of cation A in step (b) of the process can induce crystallization or precipitation of the desired POM $(A_n)^{m+}[M'M_{12}O_y$ $(RCOO)_zH_q]^{m-}$, wherein fractional crystallization is preferable. In a preferred embodiment, fractional crystallization might be accomplished by the slow addition of a specific amount of cation A to the reaction mixture of step (a) of the process or to its corresponding filtrates which might be beneficial for product purity and yield.

A preferred embodiment of the present invention is such a process wherein water is used as solvent; the at least one source of M is a water-soluble salt of $Pt^{II}$ or $Pd^{II}$, preferably selected from $PtCl_2$, $Pd(CH_3COO)_2$, $PdCl_2$, $Pd(NO_3)_2$ or $PdSO_4$, in particular a salt of $Pd^{II}$ selected from $Pd(CH_3COO)_2$, $PdCl_2$, $Pd(NO_3)_2$ or $PdSO_4$, such as $Pd(CH_3COO)_2$ or $PdCl_2$; the at least one source of M' is a water-soluble salt of $Pt^{II}$ or $Pd^{II}$, preferably platinum chloride, palladium nitrate, palladium sulphate, palladium chloride or palladium acetate, in particular a water-soluble salt of $Pd^{II}$, more preferably palladium nitrate, palladium sulphate, palladium chloride or palladium acetate; and the at least one source of RCOO-containing starting material is a water-soluble carboxylic acid or preferably a salt thereof, in particular HCOOH, $H_3CCOOH$, $H_3C(H_2C)COOH$, $H_3C(H_2C)_2COOH$, $H_3C(H_2C)_3COOH$, $(H_3C)_2(HC)COOH$, $(H_3C)_3CCOOH$, or a salt thereof, most preferably $Na(H_3CCOO)$ or $K(H_3CCOO)$, in particular $K(H_3CCOO)$.

A preferred embodiment of the present invention is such a process wherein water is used as solvent, the at least one source of M is a water-soluble salt of $Pt^{II}$ or $Pd^{II}$, preferably selected from $PtCl_2$, $Pd(CH_3COO)_2$, $PdCl_2$, $Pd(NO_3)_2$ or $PdSO_4$, in particular a salt of $Pd^{II}$ selected from $Pd(CH_3COO)_2$, $PdCl_2$, $Pd(NO_3)_2$ or $PdSO_4$, such as $Pd(CH_3COO)_2$ or $PdCl_2$; the at least one source of M' is a water-soluble gallium, thallium, indium or tin salt, preferably indium(III) nitrate or tin(IV) chloride, in particular a water-soluble indium salt, most preferably indium(III) nitrate; and the at least one source of RCOO-containing starting material is a water-soluble carboxylic acid or preferably a salt thereof, in particular HCOOH, $H_3CCOOH$, $H_3C(H_2C)COOH$, $H_3C(H_2C)_2COOH$, $H_3C(H_2C)_3COOH$, $(H_3C)_2(HC)COOH$, $(H_3C)_3CCOOH$, or a salt thereof, most preferably $Na(H_3CCOO)$ or $K(H_3CCOO)$, in particular $K(H_3CCOO)$.

A very preferred embodiment of the present invention is such a process wherein water is used as solvent, the at least one source of M is a water-soluble salt of $Pd^{II}$, preferably palladium nitrate, palladium sulfate, palladium chloride or palladium acetate, the at least one source of M' is a water-soluble salt of $Pd^{II}$, preferably palladium nitrate, palladium sulfate, palladium chloride or palladium acetate, and the at least one source of RCOO-containing starting material is a water-soluble carboxylic acid or preferably a salt thereof, in particular $Na(H_3CCOO)$ or $K(H_3CCOO)$, more particularly $K(H_3CCOO)$.

A very preferred embodiment of the present invention is such a process wherein water is used as solvent, the at least one source of M is a water-soluble salt of $Pd^{II}$, preferably palladium nitrate, palladium sulfate, palladium chloride or palladium acetate, the at least one source of M' is a water-soluble indium salt, preferably indium(III) nitrate, and the at least one source of RCOO-containing starting material is a water-soluble carboxylic acid or preferably a salt thereof, in particular $Na(H_3CCOO)$ or $K(H_3CCOO)$, more particularly $K(H_3CCOO)$.

A most preferred embodiment of the present invention is a process wherein in step (a) at least one source of M is used and all M are the same, preferably wherein all M are Pd.

According to one embodiment, the present POMs can be immobilized on a solid support. The present invention thus also relates to supported POMs comprising the POMs of the present invention or prepared by the process of the present invention on a solid support. Suitable supports include but are not limited to materials having a high surface area and/or a pore size which is sufficient to allow the POMs to be loaded, e.g., polymers, graphite, carbon nanotubes, electrode surfaces, aluminum oxide and aerogels of aluminum oxide and magnesium oxide, titanium oxide, zirconium oxide, cerium oxide, silicon dioxide, silicates, active carbon, mesoporous materials, like mesoporous silica, such as SBA-15 and MCM-41, zeolites, aluminophosphates (ALPOs), silicoaluminophosphates (SAPOs), metal organic frameworks (MOFs), zeolitic imidazolate frameworks (ZIFs), periodic mesoporous organosilicas (PMOs), and mixtures thereof and modified compounds thereof. Preferred supports are, for instance, mesoporous silica, more preferably SBA-15 or MCM-41, most preferably SBA-15. A variety of such solid supports is commercially available or can be prepared by common techniques. Furthermore, there are various common techniques to modify or functionalize solid supports, for example with regard to the size and shape of the surface or the atoms or groups available for bonding on the surface.

In a preferred embodiment of the present invention the immobilization of the POMs to the surface of the solid support is accomplished by means of adsorption, including physisorption and chemisorption, preferably physisorption. The adsorption is based on interactions between the POMs and the surface of the solid support such as van-der-Waals interactions, hydrogen-bonding interactions, ionic interactions, etc.

In a preferred embodiment the negatively charged polyanions $[M'M_{12}O_y(RCOO)_zH_q]$ are adsorbed predominantly based on ionic interactions. Therefore, a solid support bearing positively charged groups is preferably used, in particular a solid support bearing groups that can be positively charged by protonation. A variety of such solid supports is commercially available or can be prepared by common techniques. In one embodiment the solid support is functionalized with positively charged groups, preferably groups that are positively charged by protonation, and the negatively charged polyanion $[M'M_{12}O_y(RCOO)_zH_q]$ is linked to said positively charged groups by ionic interactions. In a preferred embodiment the solid support, preferably mesoporous silica, more preferably SBA-15 or MCM-41, most preferably SBA-15, is functionalized with moieties bearing positively charged groups, preferably tetrahydrocarbyl ammonium groups, more preferably groups that can be positively charged by protonation, most preferably monofunctionalized amino groups —$NH_2$. Preferably said groups are attached to the surface of the solid support by covalent bonds, preferably via a linker that comprises one or more, preferably one, of said groups, preferably an alkyl, aryl, alkenyl, alkynyl, hetero-alkyl, hetero-cycloalkyl, hetero-alkenyl, hetero-cycloalkenyl, hetero-alkynyl, hetero-aryl or cycloalkyl linker, more preferably an alkyl, aryl, hetero-alkyl or hetero-aryl linker, more preferably an alkyl linker, most preferably a methyl, ethyl, n-propyl, n-butyl, n-pentyl, n-hexyl linker, in particular a n-propyl linker. Preferably said linkers are bonded to any suitable functional group present on the surface of the solid support, such as to hydroxyl groups. Preferably said linkers are bonded to said functional groups present on the surface of the solid support either directly or via another group or atom, most preferably via another group or atom, preferably a silicon-based group, most preferably a silicon atom. In a most preferred embodiment of the present invention the POMs are supported on (3-aminopropyl)triethoxysilane (apts)-modified SBA-15.

In the supported POMs of the present invention, the POMs that are immobilized on the solid support are in the form of primary and/or secondary particles. In an especially preferred embodiment, the immobilized POMs particles are mainly in the form of primary particles (i.e., non-agglomerated primary particles), that is at least 90 wt % of the immobilized POMs particles are in the form of primary particles, preferably at least 95 wt %, more preferably at least 99 wt %, in particular substantially all the immobilized POMs particles are in the form of primary particles.

The invention is further directed to processes for preparing supported POMs according to the invention. Solid supports used in the context of this invention are as defined above. In a preferred embodiment of the present invention the surface of the solid supports is modified with positively charged groups, more preferably groups that can be positively charged by protonation. Those charged solid supports can be prepared by techniques well established in the art, for example by the surface modification of a mesoporous silica, such as SBA-15, with a suitable reagent bearing a positively charged group or a group that can be positively charged by protonation, such as 3-aminopropyltriethoxysilane (apts), is conducted by heating, preferably under reflux, under inert gas atmosphere, such as argon or nitrogen, in an inert solvent with a suitable boiling point, such as hexane, heptane or toluene, for a suitable time, such as 4-8 hours, and finally the modified solid support is isolated, preferably by filtration, purified, preferably by washing, and dried, preferably under vacuum by heating, most preferably under vacuum by heating at about 100° C.

The optionally treated support may be further calcined at a temperature of 500° C. to 800° C. For the calcination, common equipment may be used, that is commercially available. Calcination of the optionally treated support may for instance be conducted under an oxygen containing gas such as air, under vacuum, under hydrogen or under an inert gas such as argon or nitrogen, more preferably under inert gas, most preferably under nitrogen.

The POMs according to the present invention or prepared by the process of the present invention can be immobilized on the surface of the solid support by contacting said POMs with the solid support. The present invention therefore also relates to a process for the preparation of supported POMs, comprising the step of contacting the POMs provided by the present invention or prepared according to the present invention with the solid support, thereby immobilizing at least part of the POMs onto the support; and optionally isolating the resulting supported POMs.

Said contacting may be conducted employing common techniques in the art, such as blending both the solid support and the POM in the solid form. In a preferred embodiment the POM is mixed with a suitable solvent, preferably water or an aqueous solvent, and the solid support is added to this mixture. In a more preferred embodiment the solid support is mixed with a suitable solvent, preferably water or an aqueous solvent, and the POM is added to this mixture. In case a solid support with groups that can be positively charged by protonation is used, the mixture is preferably acidified, for instance by addition of $H_2SO_4$, $HNO_3$ or HCl, most preferably by addition of $H_2SO_4$ or $HNO_3$, so that the pH value of the mixture ranges from 0.1 to 6, preferably from 1 to 4 and more preferably from 1.5 to 3, most preferably is a pH of about 2. The mixture comprising POM, solid support and solvent is preferably stirred, typically for 1 min to 24 h, more preferably for 30 min to 15 h, more preferably for 1 h to 12 h, most preferably for 6 h to 10 h, in particular about 8 h. While stirring, preferably the mixture is heated to a temperature of from 20° C. to 100° C., preferably from 20° C. to 80° C., preferably from 20° C. to 60° C., preferably from 20° C. to 40° C., and most preferably about 25° C. Afterwards, the supported POM can be kept in the solvent as suspension or can be isolated. Isolation of the supported POM from the solvent may be performed by any suitable method in the art, such as by filtration, evaporation of the solvent, centrifugation or decantation, preferably by filtration or removal of the solvent in vacuum, more preferably by filtration. The isolated supported POMs may then be washed with a suitable solvent, preferably water or an aqueous solvent, and dried. Supported POMs may be dried in an oven at a temperature of, e.g., about 100° C.

In another embodiment, the supported POMs may be further calcined at a temperature not exceeding the transformation temperature of the POM i.e., the temperature at which decomposition of the POM starts to take place (usually about 150-180° C. for the present POMs according to their corresponding TGA). For the calcination, common equipment may be used, that is commercially available. Calcination of the supported POMs may for instance be conducted under an oxygen containing gas such as air, under vacuum, under hydrogen or under an inert gas such as argon or nitrogen, preferably under an oxygen containing gas such as air or an inert gas such as nitrogen, more preferably in air.

In many cases, however, and in particular if the supported POM is used as a catalyst or pre-catalyst under reductive conditions, drying of the supported POM without calcination may be sufficient. In other cases calcination might significantly improve the catalytic performance of the supported POMs according the present invention.

In a further embodiment, the supported POMs may be calcined at a temperature exceeding the transformation temperature of the POM, i.e., the temperature at which decomposition of the POM starts to take place (usually about 150-180° C. for the present POMs according to their corresponding TGA), wherein the same considerations and conclusions apply as for the calcination of non-supported POMs at a temperature exceeding the transformation temperature of the POM. A higher temperature may be used to carefully remove certain capping groups, at least partially.

In supported POMs, the POM loading levels on the solid support may be up to 30 wt % or even more, but are preferably up to 10 wt %, for instance up to 5 wt % or even up to 2 wt %. Accordingly, the POM loading level on the solid support is typically of 0.01 to 30 wt %, particularly 0.05 to 20 wt %, more particularly 0.1 to 10 wt %, often 0.2-6 wt %, more often 0.3-5 wt %, and most often 0.5-2 wt %. POM loading levels on the solid support can be determined by elemental analysis such as Inductively Coupled Plasma Mass Spectrometry (ICP-MS) analysis, for instance using a Varian Vista MPX.

According to one embodiment, the present invention also relates to a metal cluster of the formula

$$[M'M^0{}_{12}]$$

wherein
each $M^0$ is independently selected from the group consisting of $Pd^0$, $Pt^0$, $Rh^0$, $Ir^0$, $Ag^0$, and $Au^0$, preferably $Pd^0$, $Pt^0$, $Rh^0$, $Ir^0$, and $Au^0$, more preferably $Pd^0$, $Pt^0$ and $Rh^0$, most preferably $Pd^0$ and $Pt^0$, in particular $Pd^0$, and M' is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg, lanthanide metal, Ga, In, Tl, Ge, Sn, Pb, Sb and Bi, and the oxidation state of M' is 0 or greater than 0, preferably 0 to V, more preferably 0, II, or IV, most preferably 0 or II, in particular 0.

In a preferred embodiment, M' in the metal cluster [M'M$^o_{12}$] is selected from the group consisting of Sr, Sc, Ti, V, Cr, Mn, Fe, Co, Ni, Cu, Zn, Y, Zr, Ru, Rh, Pd, Ag, Cd, Lu, Re, Os, Ir, Pt and Au, preferably Ti, V, Cr, Mn, Fe, Co, Ni, Cu, Zn, Ru, Rh, Pd, Ag, Re, Os, Ir, Pt and Au, more preferably Rh, Pd, Ag, Ir, Pt and Au, even more preferably Pd, Pt and Au, most preferably Pd and Pt, in particular Pd, more particularly Pd$^o$. In another preferred embodiment, M' in the metal cluster [M'M$^o_{12}$] is selected from the group consisting of Ga, In, Tl, Ge, Sn, Pb, Sb and Bi, preferably Ga, In, Tl, Sn, Pb, Sb and Bi, more preferably Ga, In, Tl, Sn and Pb, most preferably Ga, In, Tl and Sn, in particular In or Tl, more particularly In$^o$.

In a preferred embodiment, all M$^o$ in the metal cluster [M'M$^o_{12}$] are the same, in particular all M$^o$ are Pd$^o$ or Pt$^o$, especially Pd$^o$. In case all M$^o$ in the metal cluster [M'M$^o_{12}$] are the same, the metal cluster [M'M$^o_{12}$] comprises two different types of metal atoms (M$^o$≠M') or one type of metal atoms (M$^o$=M'). Since the M$^o$ atoms are independently selected and hence may be different among each other, the metal cluster [M'M$^o_{12}$] may comprise more than two different types of metal atoms. In an embodiment of the present invention, the M$^o$ atoms are different among each other in the metal cluster [M'M$^o_{12}$] and hence, in said embodiment, the metal cluster [M'M$^o_{12}$] comprises 3 to 7 different types of metal atoms, preferably 3, 4 or 5, more preferably 3, 4, most preferably 3. However, in an especially preferred embodiment, all M$^o$ in the metal cluster [M'M$^o_{12}$] are the same and hence, in said embodiment in case M$^o$≠M', the metal cluster [M'M$^o_{12}$] comprises two different types of metal atoms.

In general in the context of the present invention, M$^o$≠M' either means that all M$^o$ are the same among each other, and hence all M$^o$ are different from M'; or that the M$^o$ are different among each other, but still all M$^o$ are different from M'.

The above considerations apply mutatis mutandis also to the formula $(A_n)^{m+}[M'M_{12}O_y(RCOO)_zH_q]^{m-}$ of the POM.

Suitable examples of metal clusters according to the invention are represented by the formulae

[M'M$^o_{12}$], e.g.,

[M'Pd$^o_{12}$], such as

[GaPd$^o_{12}$],

[InPd$^o_{12}$],

[TlPd$^o_{12}$],

[RhPd$^o_{12}$],

[OsPd$^o_{12}$],

[IrPd$^o_{12}$],

[PtPd$^o_{12}$],

[AuPd$^o_{12}$], or

[RePd$^o_{12}$];

[M'Pt$^o_{12}$];

[PdM$^o_{12}$], such as

[PdPt$^o_{12}$],

[PdRh$^o_{12}$],

[PdIr$^o_{12}$]

[PdAg$^o_{12}$], and

[PdAu$^o_{12}$].

In a further embodiment, the metal clusters of the present invention also include any metal cluster of the formula [M'M$^o_{12}$] obtainable by reduction of any of the POMs of the present invention or prepared by the process of the present invention, wherein M and M' are the same as defined above for the POMs of the present invention or prepared by the process of the present invention.

The metal clusters of the present invention are in the form of primary and/or secondary particles. In an especially preferred embodiment, the metal clusters provided by the present invention are mainly in the form of primary particles (i.e., non-agglomerated primary particles), that is at least 90 wt % of the metal clusters are in the form of primary particles, preferably at least 95 wt %, more preferably at least 99 wt %, in particular substantially all the metal clusters are in the form of primary particles. This includes metal clusters dispersed in liquid carrier media. The metal clusters of the present invention preferably have a primary particle size of about 1.0-2.0 nm, for instance about 1.5 nm.

As compared to corresponding metal clusters obtained by activation and reduction of POMs comprising other capping groups than carboxylate-based capping groups RCOO according to the present invention, e.g., capping groups being based on P, As, or Se, the metal clusters obtained by activation and reduction of POMs of the present invention or prepared by the process of the present invention (i) have been found significantly more efficient as catalysts, e.g., in the homogeneous or heterogeneous reductive conversion of organic substrate, and can be prepared in a form having (ii) a significantly higher content of primary particles, and (iii) a significantly higher degree of structural uniformity by maintaining the structural integrity of the arrangement of the former POMs with the central M' atom being entirely encapsulated by the M$_{12}$-cuboctahedron shell.

While the inventors do not wish to be bound by any particular theory, it is believed that the activation of POMs requires or is at least accompanied by the dissociation of the capping groups from the POM core. It has been found that removal of the carboxylate-based capping groups RCOO according to the present invention can be accomplished under far milder conditions, e.g., at lower temperatures, as compared to the removal of capping groups known in the art being based on P, As, or Se.

These milder activation conditions, in turn, account for (ii) a lower degree of agglomeration during said activation and further reduction and thus allowing for the preparation of metal clusters in a form having an exceptionally high content of primary particles, and (iii) an exceptionally high degree of structural uniformity with a minimum amount of point defects, i.e., the structural arrangement of the former POMs with the central M' atom being entirely encapsulated by the M$_{12}$ cuboctahedron shell is maintained.

It is believed that (ii) the lower degree of agglomeration during said calcination and, in particular, (iii) the high degree of structural integrity of the metal clusters obtained by reduction of POMs of the present invention not only account for (i) the remarkable high catalytic performance, but also allow for a very precise control of the properties of the resulting metal clusters by the specific choice of noble metal(s) in combination with the centrally located metal guest atom, i.e., in particular the high catalytic performance of the metal clusters obtained by reduction of POMs of the present invention comprising carboxylate-based capping groups RCOO can also be exceptionally well fine-tuned.

Furthermore, the milder activation conditions needed to "pretreat" the POMs of the present invention, e.g., lower temperatures, for activating POMs comprising carboxylate-based capping groups RCOO as compared to capping groups known in the art being based on P, As, or Se, also render the synthesis of the metal clusters according to the present invention more efficient and less expensive.

In this context, the conversion of a POM into its corresponding metal cluster can in general be understood as an activation of said POM followed by its reduction into the corresponding metal cluster in order to be used as catalyst in reactions in which said metal cluster provides an increased catalytic activity as compared to the POM starting material.

The preparation of metal clusters from POMs is in general accompanied with the release and potentially the subsequent conversion of the capping groups. In case of the capping groups known in the art being based on P, As, or Se, this process might be associated with the release of highly toxic substances, e.g., hydrides of Se or As as being generated under reductive conditions in the presence of reducing agents such as hydrogen. However, this is not the case for the POMs according to the present invention comprising carboxylate-based capping groups RCOO, which in general do not lead to highly toxic side products, e.g., reductive conversion of carboxylates commonly yields the corresponding alcohols or alkanes. As to the impact of the toxicity of the capping groups or their derivatised products, the same conclusion applies to any other process involving the use of POMs which use is accompanied by the release and potentially the subsequent conversion of the respective capping groups of the POM used.

In a further embodiment, the metal clusters are dispersed in a liquid carrier medium, thereby forming a dispersion of metal clusters. In one embodiment of the present invention the liquid carrier medium is an organic solvent, optionally combined with one or more dispersing agents. The organic solvent is preferably capable of dissolving the POMs used as starting material for the preparation of the metal clusters, for instance liquid n-alkanes, e.g., hexane or heptane.

The dispersing agent (or surfactant) is added to the liquid carrier medium to prevent agglomeration of the primary particles of metal cluster. Preferably, the dispersing agent is present during formation of the primary particles of metal cluster. An example of a surfactant useful as dispersing agent is citric acid or citrate. The dispersing agent preferably forms micelles, each micelle containing one primary particle of metal cluster thereby separating the primary particles from each other and preventing agglomeration thereof.

In another further embodiment, the metal clusters can be immobilized on a solid support thereby forming supported metal clusters. Suitable supports include but are not limited to materials having a high surface area and/or a pore size which is sufficient to allow the metal clusters to be loaded, e.g., polymers, graphite, carbon nanotubes, electrode surfaces, aluminum oxide and aerogels of aluminum oxide and magnesium oxide, titanium oxide, zirconium oxide, cerium oxide, silicon dioxide, silicates, active carbon, mesoporous materials, like mesoporous silica, such as SBA-15 and MCM-41, zeolites, aluminophosphates (ALPOs), silicoaluminophosphates (SAPOs), metal organic frameworks (MOFs), zeolitic imidazolate frameworks (ZIFs), periodic mesoporous organosilicas (PMOs), and mixtures thereof and modified compounds thereof. Preferred supports are, for instance, mesoporous silica, more preferably SBA-15 or MCM-41, most preferably SBA-15.

A variety of such solid supports is commercially available or can be prepared by common techniques. Furthermore, there are various common techniques to modify or functionalize solid supports, for example with regard to the size and shape of the surface or the atoms or groups available for bonding on the surface. In a preferred embodiment of the present invention the immobilization of the metal clusters to the surface of the solid support is accomplished by means of adsorption, including physisorption and chemisorption, preferably physisorption. The adsorption is based on interactions between the metal clusters and the surface of the solid support, such as van-der-Waals interactions.

In the supported metal clusters of the present invention, the metal clusters that are immobilized on the solid support are in the form of primary and/or secondary particles. In an especially preferred embodiment, the immobilized metal cluster particles are mainly in the form of primary particles (i.e., non-agglomerated primary particles), that is at least 90 wt % of the immobilized metal cluster particles are in the form of primary particles, preferably at least 95 wt %, more preferably at least 99 wt %, in particular substantially all the immobilized metal cluster particles are in the form of primary particles.

In the supported metal clusters of the present invention, the metal cluster loading levels on the solid support may be up to 30 wt % or even more, but are preferably up to 10 wt %, for instance up to 5 wt % or even up to 2 wt %. Accordingly, the metal cluster loading level on the solid support is typically of 0.01 to 30 wt %, particularly 0.05 to 20 wt %, more particularly 0.1 to 10 wt %, often 0.2-6 wt %, more often 0.3-5 wt %, and most often 0.5-2 wt %. Metal cluster loading levels on the solid support can be determined by elemental analysis such as Inductively Coupled Plasma Mass Spectrometry (ICP-MS) analysis, for instance using a Varian Vista MPX.

The invention is further directed to processes for preparing metal clusters according to the invention.

Among the preferred processes for preparing any one of the metal clusters of the present invention is a process for the preparation of a dispersion of said metal clusters dispersed in liquid carrier media. Said process comprises:
  (a) dissolving any one of the POMs provided by the present invention or prepared according to the present invention in a liquid carrier medium,
  (b) optionally providing additive means to prevent agglomeration of the metal clusters to be prepared, preferably adding compounds capable of preventing agglomeration of metal clusters to be prepared, more preferably adding surfactants to enable micelle formation, and
  (c) subjecting the dissolved POM to chemical or electrochemical reducing conditions sufficient to at least partially reduce said POM into corresponding metal clusters.

In a preferred embodiment in step (a), the liquid carrier medium capable of dissolving the POM used for the preparation of the metal clusters is an organic solvent, such as liquid n-alkanes, e.g., hexane or heptane.

In a preferred embodiment in step (b), classical capping groups such as diverse types of inorganic and organic anions, such as carboxylates, e.g., citrate, may be used to prevent agglomeration of the metal clusters to be prepared.

In a preferred embodiment in step (c), the chemical reducing conditions comprise the use of a reducing agent selected from organic and inorganic materials which are oxidizable by $Pd^{II}$, $Pt^{II}$, $Rh^{I}$, $Ir^{I}$, $Ag^{I}$ and $Ag^{III}$, and $Au^{I}$ and $Au^{III}$. Such a chemical reduction can for example be effected by using borohydrides, aluminohydrides, hydrazine, CO or hydrogen, preferably hydrogen, more preferably hydrogen at elevated temperature and pressure, preferably by using hydrogen. In the alternative, the POM in step (c) is reduced electrochemically using a common electrochemical cell.

The metal clusters of the present invention can be immobilized on the surface of a solid support. The present invention therefore also relates to processes for the preparation of supported metal clusters according to the present invention. A first process for the preparation of supported metal clusters comprises contacting the dispersion of metal clusters provided by the present invention or prepared according to the present invention with a solid support, thereby immobilizing at least part of the dispersed metal clusters onto the support; and optionally isolating the supported metal clusters.

In a preferred embodiment, the solid support is added to the dispersion of metal clusters. The resulting mixture is preferably stirred, typically for 1 min to 24 h, more preferably for 30 min to 15 h, more preferably for 1 h to 12 h, most preferably for 6 h to 10 h, in particular about 8 h. While stirring, preferably the mixture is heated to a temperature of from 20° C. to 100° C., preferably from 20° C. to 80° C., preferably from 20° C. to 60° C. preferably from 20° C. to 40° C., and most preferably about 25° C. Afterwards, the supported metal clusters are preferably isolated. Isolation of the supported metal clusters from the solvent may be performed by any suitable method in the art, such as by filtration, evaporation of the solvent, centrifugation or decantation, preferably by filtration or removal of the solvent in vacuum, more preferably by filtration. The isolated supported metal clusters may then be washed with a suitable solvent, preferably water or an aqueous solvent, and dried, for instance by heating under vacuum.

Another suitable process for the preparation of supported metal clusters according to the present invention comprises: subjecting supported POM provided by the present invention or prepared according to the present invention to chemical or electrochemical reducing conditions sufficient to at least partially reduce said POM into corresponding metal clusters; and optionally isolating the supported metal clusters.

In a preferred embodiment, the chemical reducing conditions comprise the use of a reducing agent selected from organic and inorganic materials which are oxidizable by $Pd^{II}$, $Pt^{II}$, $Rh^{I}$, $Ir^{I}$, $Ag^{I}$ and $Ag^{III}$, and $Au^{I}$ and $Au^{III}$. Such a chemical reduction can for example be effected by using borohydrides, aluminohydrides, hydrazine, CO or hydrogen, preferably hydrogen, more preferably hydrogen at elevated temperature and pressure. In the alternative, the POM is reduced electrochemically using a common electrochemical cell.

The invention is also directed to the use of optionally supported POMs provided by the present invention or prepared according to the present invention and/or optionally supported or dispersed metal clusters provided by the present invention or prepared according to the present invention, for catalyzing homogeneous and heterogeneous reductive conversion of organic substrates.

In a preferred embodiment, reductive conversion refers to homogeneous or heterogeneous reduction and/or hydroprocessing and/or hydrocracking and/or (hydro)desulfurization of organic substrate.

Within the present reductive conversion of organic substrates, a variety of reducing reagents can be used, including hydrogen or a hydrogen-containing atmosphere. In a preferred embodiment the process for the homogeneous or heterogeneous reductive conversion of organic substrate comprises contacting said organic substrate under addition of hydrogen with the optionally supported POMs provided by the present invention or prepared according to the present invention and/or optionally supported or dispersed metal clusters provided by the present invention or prepared according to the present invention.

Since the M metal atoms are not fully sterically shielded by the polyanion backbone, various noble metal coordination sites are easily accessible to the organic substrate and the reducing reagent or reduction active transfer molecule and therefore high catalytic activities are achieved. Further, the thermal stability of the optionally supported POMs of the present invention permits their use under a variety of reaction conditions.

It is contemplated that the optionally supported POMs of the present invention can be activated prior to or within the reduction reaction by any process described herein or any process known in the art, preferably by increasing the accessibility to their noble metal atoms M.

Compared with the optionally supported POMs of the present invention, the accessibility of the noble metal atoms in the optionally supported or dispersed metal clusters of the present invention is even better because of the absence of any ligands, e.g., capping groups. Further, the remarkable thermal stability of the optionally supported or dispersed metal clusters of the present invention is at least comparable to, in particular greater than, more particularly far greater than, the one of the optionally supported POMs therefore permitting their use under a variety, particularly under a great variety of reaction conditions.

It is contemplated that the optionally supported POMs of the present invention can be reduced under the reductive reaction conditions of the reductive conversion described herein. Thus, it might be possible that the optionally supported POMs are reductively converted into metal cluster-like structures or even into metal clusters under the conversion reaction conditions and it might be possible that said metal cluster-like structures or said metal clusters are actually the catalytically active species. Nevertheless, the optionally supported POMs of the present invention give excellent results in homogeneous and heterogeneous reductive conversion of organic substrates, regardless of the specific nature of the actually catalytically active species. Analogous considerations and conclusions regarding the actual catalytically active species apply to the optional activation of the optionally supported POMs.

Another useful aspect of this invention is that the optionally supported POMs and/or optionally supported or dispersed metal clusters of the present invention can be recycled and used multiple times for the reduction of organic molecules.

In a preferred embodiment this invention thus also relates to a process for reducing organic substrates comprising the steps:

(a) contacting a first organic substrate under addition of hydrogen with one or more optionally supported POMs and/or one or more supported metal clusters, (b) recovering the one or more optionally supported POMs and/or one or more supported metal clusters;

(c) contacting the one or more optionally supported POMs and/or one or more supported metal clusters with a solvent at a temperature of 50° C. or more, and/or hydrogen stripping the one or more optionally supported POMs and/or the one or more supported metal clusters at elevated temperature, and/or calcining the one or more optionally supported POMs and/or the one or more supported metal clusters at elevated temperature under an oxygen containing gas, e.g., air, or under an inert gas, e.g., nitrogen or argon, to obtain a recycled one or more optionally supported POMs and/or one or more supported metal clusters;

(d) contacting the recycled one or more optionally supported POMs and/or one or more supported metal clusters under addition of hydrogen with a second organic substrate which may be the same as or different from the first organic substrate; and (e) optionally repeating steps (b) to (d).

The contacting of organic substrate under addition of hydrogen with optionally supported POM and/or supported metal cluster in step (a) may, e.g., be carried out in a continuously stirred tank reactor (CSTR), a fixed bed reactor, a fluidized bed reactor or a moving bed reactor.

Thus, e.g., the optionally supported POMs and/or supported metal clusters of the present invention can be collected after a reduction reaction, washed with a polar or non-polar solvent such as acetone and then dried under heat (typically 50° C. or more, alternately 75° C. or more, alternately 100° C. or more, alternately 125° C. or more) for 30 minutes to 48 hours, typically for 1 to 24 hours, more typically for 2 to 10 hours, more typically for 3 to 5 hours.

Alternatively to or in addition to the washing, the optionally supported POMs and/or supported metal clusters may be subjected to hydrogen stripping at elevated temperature. Preferably, the hydrogen stripping is carried out at a temperature of 50° C. or higher, more preferably at a temperature of 75° C. or higher and most preferably at a temperature of 100° C. or higher.

Alternatively to or in addition to the washing and/or hydrogen stripping, the optionally supported POMs and/or supported metal clusters may be calcined at elevated temperature under an oxygen containing gas, e.g., air, or under an inert gas, e.g., nitrogen or argon. Preferably, the calcination is carried out at a temperature in the range from 75° C. to 150° C., such as from 90° C. to 120° C. or from 120 OC to 150° C.

In a further embodiment, any washing/drying and/or hydrogen stripping and/or calcining step of the optionally supported POMs and/or supported metal clusters can also be performed at a temperature exceeding the transformation temperature of the POM, i.e., the temperature at which decomposition of the POM starts to take place (usually about 150-180° C. for the present POMs according to their corresponding TGA), wherein in this context for the optionally supported POMs the same considerations and conclusions apply as for the general calcination of optionally supported POMs at a temperature exceeding the transformation temperature of the POM and/or the general activation of the optionally supported POMs.

The washing and/or hydrogen stripping and/or calcining has/have the effect of regenerating the optionally supported POMs and/or supported metal clusters for recycling.

The recycled optionally supported POMs and/or supported metal clusters of the present invention may be used on fresh organic molecules, or on recycled organic molecules from a recycle stream.

It is preferred to use supported POMs and/or supported metal clusters of the present invention as catalysts with regard to recovery and recycling of the catalyst in the reductive conversion processes described herein. Advantageously, the supported POMs and/or supported metal clusters of the present invention may be recycled and used again under the same or different reaction conditions. Typically the supported POMs and/or supported metal clusters are recycled at least 1 time, preferably at least 4 times, preferably at least 8 times, preferably at least 12 times, preferably at least 100 times.

Thus, this invention also relates to a process for reducing organic substrates (typically an arene) which process comprises contacting a first organic substrate with one or more supported POMs and/or supported metal clusters of the present invention, thereafter recovering the supported POMs and/or supported metal clusters of the present invention, contacting the supported POMs and/or supported metal clusters of the present invention with a solvent (such as acetone) at a temperature of 50° C. or more, and/or hydrogen stripping the supported POMs and/or supported metal clusters at elevated temperature, and/or calcining the supported POMs and/or supported metal clusters to obtain recycled supported POMs and/or supported metal clusters of the present invention, thereafter contacting the recycled supported POMs and/or supported metal clusters of the present invention with a second organic substrate, which may be the same as or different from the first organic substrate, this process may be repeated many times, preferably at least 4 times, preferably at least 8 times, preferably at least 12 times, preferably at least 100 times.

Due to the definite stoichiometry of POMs, the optionally supported POMs of the present invention can be converted (e.g., by calcination at a temperature exceeding the transformation temperature) to mixed metal-oxide catalysts in a highly reproducible manner. Consequently, the optionally supported POMs according to the present invention can also be used as a precursor for mixed metal-oxide catalysts.

Metal clusters of the present invention, optionally supported or dispersed in a liquid carrier medium, can be described as nanocatalysts of M' and M at the atomic or molecular level, i.e., particles of M' and M having an average diameter of about 1.0-2.0 nm, for instance about 1.5 nm, obtained by reduction of the POMs. In the case of the preferred embodiment, wherein all M are the same, nanocatalysts with at least one noble atom species are obtained. In another embodiment in which at least one or more M are different among each other nanocatalysts with more than one noble atom species, such as 2 to 6 noble atom species, preferably 2, 3 or 4, more preferably 2 or 3, most preferably 2, are obtained. Thus, the bottom-up approach of the present invention allows for the preparation of noble metal-rich customized nanocatalysts of very well defined size and shape, in which two or more than two metal species can be selected individually from groups that contain or consist of the noble metal elements Rh, Ir, Pd, Pt, Ag, and Au and one additional metal element selected from Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg, lanthanide metal, Ga, In, Tl, Ge, Sn, Pb, Sb and Bi comprising inter alia a variety of noble metal and post-transition-metal elements.

The obtained metal clusters can be used for a wide range of catalytic applications such as in fuel cells, for detection of organic substrates, selective hydrogenation, reforming, hydrocracking, hydrogenolysis and oligomerization.

Besides immobilizing the present POMs on a matrix surface and subsequently reducing them, the deposition of the POMs on a surface matrix and their reduction can also be carried out simultaneously.

In addition, e.g., the POMs according to the invention can be used to produce modified electrodes by electrochemical deposition of the POM on an electrode surface such as a glassy carbon (GC) electrode surface. The obtained deposits contain predominantly $M^0$ such as $Rh^0$, $Ir^0$, $Pd^0$, $Pt^0$, $Ag^0$, $Au^0$, and preferably mixtures thereof with very small amounts $M\chi^+$ such as $Pd^{II}$, $Pt^{II}$, $Rh^I$, $Ir^I$, $Ag^I$, $Ag^{III}$, $Au^I$, and $Au^{III}$ and mixtures thereof, preferably $Pd^{II}$, $Pt^{II}$, $Rh^I$, $Ir^I$, $Ag^I$, and $Au^I$. In a preferred embodiment, the obtained deposits provide improved electrochemical behaviors like improved kinetics of electrocatalytic processes compared to a film deposited using a conventional precursor of M and M'. For example, electrodes modified with a deposit of the present POMs can be used for the electrochemical reduction of organic substrates. It has been found that such modified electrodes show a very small overpotential and a remarkably high shelf life.

EXAMPLES

The invention is further illustrated by the following examples.

Example 1: Synthesis of $K_5[In^{III}Pd^{II}{}_{12}O_8(H_3CCOO)_{16}]\cdot K_2Pd(H_3CCOO)_4\cdot 4K(H_3CCOO)\cdot 20H_2O$ $Pd(CH_3COO)_2$ (0.023 g, 0.1 mmol) and $In(NO_3)_3\cdot H_2O$ (0.008 g, 0.025 mmol) were dissolved in 0.5 M $K(H_3CCOO)$ solution (2 mL, 0.2 mmol, pH 7.0). The solution was heated to 50° C. under stirring for 120 minutes. Then the solution was allowed to cool to room temperature, filtered, and the filtrate left for crystallization at room temperature in an open vial. Dark red, block-shaped crystals were obtained after 2 weeks, which were collected by filtration and air-dried. Yield: 0.015 g (50% based on Pd). This product was analyzed by XRD, IR, elemental analysis, TGA and $^{13}C$ NMR and was identified as $[In^{III}Pd^{II}{}_{12}O_8(H_3CCOO)_{16}]^{5-}$ polyanion ("InPd$_{12}$"), isolated as hydrated potassium salt $K_5[In^{III}Pd^{II}{}_{12}O_8(H_3CCOO).16]\cdot K_2Pd(H_3CCOO)_4\cdot 4K(H_3CCOO)\cdot 20H_2O$ ("K—InPd$_{12}$").

Example 2: Analysis of "K—InPd$_{12}$"

The IR spectrum with 4 cm$^{-1}$ resolution was recorded on a Nicolet Avatar 370 FT-IR spectrophotometer on KBr pellet sample (peak intensities: w=weak; m=medium; s=strong). The characteristic region of the polyanion is between 2000-400 cm$^{-1}$ due to metal-oxygen stretching vibrations: 1603 (s), 1423 (s), 1383 (s), 1328 (m), 1043 (w), 1020 (w), 692 (m), 650 (m), 617 (w), 522 (w). The FT-IR spectrum is shown in FIG. 3. Absorption bands that correspond to different vibrational modes of Pd—O groups appear in the regions between 692 and 522 cm$^{-1}$. The absorption band near 1603 cm$^{-1}$ is attributed to asymmetric vibrations of the crystal waters.

Elemental analysis for "K—InPd$_{12}$" calculated (found): K, 11.2 (11.2), In, 2.99 (2.83), Pd, 36.1 (36.3), C, 15.04 (15.30), H, 2.94 (3.11).

Thermogravimetric analysis (TGA) was performed on a SDT Q 600 device from TA Instruments with 10-30 mg samples in 100 µL alumina pans, under a 100 mL/min $N_2$ flow with a heating rate of 5° C./min between 20° C. and 800° C. (FIG. 1). Only one weight-loss step was observed on the thermogram below 180° C. while a second weight-loss step was observed between 180° C. and 240° C., wherein it is believed that the first weight-loss step can be attributed to the loss of loosely bound waters of crystallization present in the POM salt, whereas the second weight-loss step appears to be associated with the loss of more strongly bound crystal waters as well as the loss of acetate capping groups.

Example 3: Single Crystal X-Ray Diffraction (XRD) Data and Analysis of "K—InPd$_{12}$"

Besides IR, elemental analysis and TGA the product was also characterized by single-crystal XRD. The crystal was mounted in Hampton cryoloop at 100 K using light oil for data collection. Indexing and data collection were carried on a Bruker Kappa X8 APEX II CCD single crystal diffractometer with K geometry and Mo Kα radiation (λ=0.71073 Å). The SHELX software package (Bruker) was used to solve and refine the structure. An empirical absorption correction was applied using the SADABS program as disclosed in G. M. Sheldrick, SADABS, Program for empirical X-ray absorption correction, Bruker-Nonius: Madison, Wis. (1990). The structure was solved by direct method and refined by the full-matrix least squares method ($\Sigma w(|F_o|^2-|F_c|^2)^2$) with anisotropic thermal parameters for all heavy atoms included in the model. The H atoms of the crystal waters were not located. Also, it was not possible to locate all potassium counter cations by XRD, due to crystallographic disorder. The exact number of counter cations and crystal water in the POM were thus based on elemental analysis. Compound "K—InPd$_{12}$" crystallizes in the tetragonal space group I4/m. Crystallographic data are detailed in Table 1.

TABLE 1

Crystal data for "K-InPd$_{12}$".

| | |
|---|---|
| Empirical formula | $C_{48}H_{112}K_{11}O_{76}InPd_{13}$ |
| Formula weight, g/mol | 3833.47 |
| Crystal system | Tetragonal |
| Space group | I4/m |
| a, Å | 14.9260(2) |
| b, Å | 14.9260(2) |
| c, Å | 26.4376(7) |
| α, ° | 90 |
| β, ° | 90 |
| γ, ° | 90 |
| Volume, Å$^3$ | 5889.9(2) |
| Z | 2 |
| $D_{calc}$, g/cm$^3$ | 2.477 |
| Absorption coefficient, mm$^{-1}$ | 2.804 |
| F(000) | 2323 |
| Theta range for data collection, ° | 1.567 to 28.415 |
| Completeness to $\Theta_{max}$ % | 99.8 |
| Index ranges | $-18 <= h <= 40$, $-39 <= k <= 40$, $-39 <= l <= 40$ |
| Reflections collected | 29826 |
| Independent reflections | 1770 |
| R(int) | 0.0532 |
| Absorption correction | Semi-empirical from equivalents |
| Data/restraints/parameters | 2131/282/109 |
| Goodness-of-fit on F$^2$ | 1.691 |
| $R_1$[a], $wR_2$[b] (I > 2σ(I)) | $R_1 = 0.0795$, $wR_2 = 0.1572$ |
| $R_1$[a], $wR_2$[b] (all data) | $R_1 = 0.03209$, $wR_2 = 0.3606$ |
| Largest diff. peak and hole, e/Å$^3$ | 3.145 and −3.774 |

[a] $R_1 = \Sigma ||F_o| - |F_c||/\Sigma|F_o|$.
[b] $wR_2 = [\Sigma w (F_o^2 - F_c^2)^2/\Sigma w(F_o^2)^2]^{1/2}$

Example 4: Structure of "InPd$_{12}$" Polyanion

The structure of "InPd$_{12}$" polyanion is displayed in FIG. 2. The central In$^{III}$ ion has a cubic geometry and is coordinated by eight oxygen atoms leading to a InO$_8$ cuboid fragment (In—O of 2.2679(67) Å) in which each 4-oxo ligand bridges the central In$^{III}$ and three Pd$^{II}$ ions. The twelve Pd$^{II}$ ions all adopt a square-planar coordination geometry and form a distorted cuboctahedron around the central In$^{III}$. The resulting InO$_8$Pd$_{12}$ assembly is surrounded by the 16 acetate ligands, which are bonded to all twelve Pd$^{II}$ ions. Each of the twelve Pd$^{II}$ ions coordinates two carboxyl oxygen atoms from two different acetate ligands, wherein the overall 24 coordination sites of the twelve Pd$^{II}$ ions are occupied by eight bidentate acetate ligands (Pd—O of 2.0124 Å) and eight monodentate acetate ligands (Pd—O of 2.0463 Å).

Example 5: $^{13}$C NMR Spectrum of "K—InPd$_{12}$"

"K—InPd$_{12}$" crystals were dissolved in H$_2$O/D$_2$O. $^{13}$C NMR spectrum was recorded at room temperature on a 400 MHz JEOL ECX instrument, using 5 mm tube with resonance frequency 100.71 MHz. The chemical shift is reported with respect to the reference Si(CH$_3$)$_4$. The $^{13}$C NMR spectrum is shown in FIG. 4.

Example 6: Synthesis of Supported "InPd$_{12}$" POM

Synthesis of Mesoporous Silica Support SBA-15.

8.0 g of Pluronic® P-123 gel (Sigma-Aldrich) were added to 40 mL of 2 M HCl and 208 mL H$_2$O. This mixture was stirred for 2 hours in a water bath at 35° C. until it was completely dissolved. Then 18 mL of tetraethylorthosilicate (TEOS) was added dropwise, and the mixture was kept under stirring for 4 hours. Afterwards, the mixture was heated in an oven at 95° C. for 3 days. The white precipitate was collected by filtration, washed and air-dried. Finally, the product was calcined by heating the as-synthesized material to 550° C. at a rate of 1-2° C./min and kept at 550° C. for 6 hours to remove the templates.

Synthesis of Modified SBA-15-Apts.

1.61 mL of 3-aminopropyltriethoxysilane (apts) was added to 3 g of SBA-15, prepared according to the synthesis described above, in 90 mL toluene. This mixture was refluxed for 5 hours and then filtered at room temperature. The obtained modified SBA-15-apts was heated at 100° C. for 5 hours.

Preparation of "InPd$_{12}$" POM Supported on SBA-15-Apts (Supported "InPd$_{12}$" POM).

"K—InPd$_{12}$" was dissolved in water (0.056 mmol/L), resulting in a colored solution. While stirring, SBA-15-apts was slowly added to the solution of "K—InPd$_{12}$" so that the respective amounts of "K—InPd$_{12}$" and SBA-15-apts were 5 wt % and 95 wt %, respectively. The mixture was kept under stirring for 24 hours at 40° C., filtered and then washed three times with water. The filtrate was colorless, indicating that the "InPd$_{12}$" POM was quantitatively loaded on the SBA-15-apts support, leading to an "InPd$_{12}$" POM loading level on the solid support of about 5 wt %. The supported product was then collected and air-dried.

Example 7: Activation of Supported "InPd$_{12}$" POM and Preparation of Supported "InPd$_{12}$" Metal Clusters The supported "InPd$_{12}$" POM prepared according to example 6 was activated by air calcination and then transformed into the corresponding supported "InPd$_{12}$" metal clusters by H$_2$ reduction.

In a first example 7a, supported "InPd$_{12}$" POM prepared according to example 6 was activated by air calcination at 150° C. for 1 hour. In a second example 7b, supported "InPd$_{12}$" POM prepared according to example 6 was activated by air calcination at 200° C. for 1 hour. In a third example 7c, supported "InPd$_{12}$" POM prepared according to example 6 was activated by air calcination at 300° C. for 30 minutes. In a fourth example 7d, supported "InPd$_{12}$" POM prepared according to example 6 was activated by air calcination at 550° C. for 30 minutes.

The activated supported "InPd$_{12}$" POMs of examples 7a, 7b, 7c and 7d were converted into corresponding supported "InPd$_{12}$" metal clusters by H$_2$ reduction at 240° C. and 60 bar under stirring at 1500 rpm for 1-2 minutes. The H$_2$ reduction was conducted in-situ prior to the testing of the catalytic hydrogenation properties of the supported "InPd$_{12}$" metal clusters as detailed in example 8.

Without being bound by any theory, it is believed that calcination and hydrogenation helps to activate the POM by forming active sites.

Example 8: Catalytic Activity of Supported "InPd$_{12}$" Metal Clusters

The activated supported "InPd$_{12}$" POMs of examples 7a, 7b, 7c and 7d were tested for catalytic hydrogenation of o-xylene after their in-situ transformation into corresponding supported "InPd$_{12}$" metal clusters.

The hydrogenation of o-xylene was carried out in a 100 mL Parr 5513 stainless steel high-pressure compact reactor equipped with a magnetically coupled stirrer drive ensuring a well-mixed environment of reactants. The reaction mixture contained 3.5 mL of o-xylene in 47.5 mL hexane and 50 mg of activated supported "InPd$_{12}$" POMs (5 wt %) and was stirred at 1500 rpm. The autoclave was purged with H$_2$ and then heated and pressurized to the desired set point of temperature (300° C.) and pressure (90 bar) respectively. Prior to reaching the set point, the activated supported "InPd$_{12}$" POMs were reduced in-situ in the reactor at 240° C. and 60 bar and stirred at 1500 rpm for 1-2 minutes. This process is exothermic and helps reaching the desired temperature set point. The reaction starts once the desired conditions are reached. In order to prove catalyst recyclability, adding a new portion of substrate into the reactor after reaction completion followed all catalytic runs (i.e., running more than one cycle).

The reaction was followed by H$_2$ consumption and gas chromatography (GC) analysis. A GC-2010 Shimadzu instrument equipped with a flame ionization detector (FID) was used to measure substrate conversion and selectivity of obtained products via a HP-5 column (15 m×0.25 mm) providing good separation of reaction products. The carrier gas was He. This overall procedure ensured good reproducibility of the catalytic experiments.

The SBA-15-apts support alone did not show any hydrogenation activity while the supported "InPd$_{12}$" metal clusters showed catalytic performances with full conversion of o-xylene to cis/trans-1,2-dimethylcyclohexane. The conversion and cis/trans selectivity (expressed as cis/trans molar ratio) obtained for the supported "InPd$_{12}$" metal clusters derived from the activated supported "InPd$_{12}$" POMs of examples 7a, 7b, 7c and 7d are summarized in Table 4 below.

TABLE 4

Catalytic performance of supported "InPd$_{12}$" metal clusters.

| Sample | Time (min) | Conversion (mol %) | Cis/Trans Selectivity |
|---|---|---|---|
| 7a | 130 | ≈100 | 43/57 |
| 7b | 105 | ≈100 | 44/56 |
| 7c | 195 | ≈100 | 45/55 |
| 7d | 330 | ≈100 | 45/55 |

The catalytic performance of the supported "InPd$_{12}$" metal clusters was thus excellent compared to other commercial catalysts. In addition, these results show that the supported "InPd$_{12}$" POM of example 6 can be activated at quite low temperatures such as at 150° C. or 200° C. for 1 hour, as illustrated by examples 7a and 7b. The POMs of the present invention therefore present an advantage as compared to other POMs due to the lower temperature needed for their activation, i.e. just the necessary temperature to at least partially remove the carboxylate groups.

Example 9: Synthesis of K$_5$[Tl$^{III}$Pd$^{II}_{12}$O$_8$(H$_3$CCOO)$_{16}$].K$_2$Pd(H$_3$CCOO)$_4$.4K(H$_3$CCOO).20H$_2$O Pd(CH$_3$COO)$_2$ (0.069 g, 0.3 mmol) and Tl(NO$_3$)$_3$.H$_2$O (0.033 g, 0.075 mmol) were dissolved in 1 M K(H$_3$CCOO) solution (3 mL, 0.2 mmol, pH 7.0). The solution was heated to 50° C. under stirring for 120 minutes. Then the solution was allowed to cool to room temperature, filtered, and the filtrate left for crystallization at room temperature in an open vial. Dark red, block-shaped crystals were obtained after 2 weeks, which were collected by filtration and air-dried. Yield: 0.020 g (18% based on Pd). This product was analyzed by XRD, IR, TGA and $^{13}$C NMR and was identified as [Tl$^{III}$Pd$^{II}_{12}$O$_8$(H$_3$CCOO)$_{16}$]$^{5-}$ polyanion ("TlPd$_{12}$"), isolated as hydrated potassium salt K$_5$[Tl$^{III}$Pd$^{II}$12O$_8$(H$_3$CCOO)$_{16}$].K$_2$Pd(H$_3$CCOO)$_4$.4K(H$_3$CCOO).20H$_2$O ("K—TlPd$_{12}$").

Example 10: Analysis of "K—TlPd$_{12}$"

The IR spectrum with 4 cm$^{-1}$ resolution was recorded on a Nicolet Avatar 370 FT-IR spectrophotometer on KBr pellet sample (peak intensities: w=weak; m=medium; s=strong). The characteristic region of the polyanion is between 2000-400 cm$^{-1}$ due to metal-oxygen stretching vibrations: 1601 (s), 1427 (s), 1384 (s), 1329 (s), 1041 (w), 1020 (w), 689 (m), 638 (m), 591 (w), 520 (w), 489 (w). The FT-IR spectrum is shown in FIG. 7. Absorption bands that correspond to different vibrational modes of Pd—O groups appear in the regions between 689 and 489 cm$^{-1}$. The absorption band near 1601 cm$^{-1}$ is attributed to asymmetric vibrations of the crystal waters.

Thermogravimetric analysis (TGA) was performed on a SDT Q 600 device from TA Instruments with 10-30 mg samples in 100 µL alumina pans, under a 100 mL/min N$_2$ flow with a heating rate of 5° C./min between 20° C. and 800° C. (FIG. 5). Only one weight-loss step was observed on the thermogram below 180° C. while a second weight-loss step was observed between 180° C. and 240° C., wherein it is believed that the first weight-loss step can be attributed to the loss of loosely bound waters of crystallization present in the POM salt, whereas the second weight-loss step appears to be associated with the loss of more strongly bound crystal waters as well as the loss of acetate capping groups.

Example 11: Single Crystal X-Ray Diffraction (XRD) Data and Analysis of "K—TlPd$_{12}$"

Besides IR and TGA the product was also characterized by single-crystal XRD. The crystal was mounted in Hampton cryoloop at 100 K using light oil for data collection. Indexing and data collection were carried on a Bruker Kappa X8 APEX II CCD single crystal diffractometer with K geometry and Mo Kα radiation (λ=0.71073 Å). The SHELX software package (Bruker) was used to solve and refine the structure. An empirical absorption correction was applied using the SADABS program as disclosed in G. M. Sheldrick, SADABS, Program for empirical X-ray absorption correction, Bruker-Nonius: Madison, Wis. (1990). The structure was solved by direct method and refined by the full-matrix least squares method ($\Sigma w(|F_o|^2 - |F_c|^2)^2$) with anisotropic thermal parameters for all heavy atoms included in the model. The H atoms of the crystal waters were not located. Also, it was not possible to locate all potassium counter cations by XRD, due to crystallographic disorder. The exact number of counter cations and crystal water in the POM were thus based on elemental analysis. Compound "K—TlPd$_{12}$" crystallizes in the tetragonal space group I4/m. Crystallographic data are detailed in Table 2.

TABLE 2

Crystal data for "K-TlPd$_{12}$".

| | |
|---|---|
| Empirical formula | C$_{48}$H$_{112}$K$_{11}$O$_{84}$Tlpd$_{13}$ |
| Formula weight, g/mol | 3844.64 |
| Crystal system | Tetragonal |
| Space group | I4/m |
| a, Å | 14.9557(4) |
| b, Å | 14.9557(4) |
| c, Å | 26.5259(8) |
| α, ° | 90 |
| β, ° | 90 |
| γ, ° | 90 |
| Volume, Å$^3$ | 5933.1(4) |
| Z | 2 |
| D$_{calc}$, g/cm$^3$ | 2.208 |
| Absorption coefficient, mm$^{-1}$ | 3.618 |
| F(000) | 3828 |
| Theta range for data collection, ° | 1.535 to 28.325 |
| Completeness to Θ$_{max}$ % | 99.8 |
| Index ranges | −19 <= h <= 19, |
| | −14 <= k <= 19, |
| | −35 <= l <= 32 |
| Reflections collected | 25759 |
| Independent reflections | 2129 |
| R(int) | 0.0369 |
| Absorption correction | Semi-empirical from equivalents |
| Data/restraints/parameters | 2129/129/112 |
| Goodness-of-fit on F$^2$ | 1.053 |
| R$_1$[a], wR$_2$[b] (I > 2σ(I)) | R$_1$ = 0.0707 wR$_2$ = 0.2511 |
| R$_1$[a], wR$_2$[b] (all data) | R$_1$ = 0.0906, wR$_2$ = 0.2865 |
| Largest diff. peak and hole, e/Å$^3$ | 5.422 and −4.091 |

[a]R$_1$ = Σ||F$_o$| − F$_c$||/Σ|F$_o$|.
[b]wR$_2$ = [Σw (F$_o^2$ − F$_c^2$)$^2$/Σw(F$_o^2$)$^2$]$^{1/2}$

Example 12: Structure of "TlPd$_{12}$" Polyanion

The structure of "TlPd$_{12}$" polyanion is displayed in FIG. 6. The central Tl$^{III}$ ion has a cubic geometry and is coordinated by eight oxygen atoms leading to a TlO$_8$ cuboid fragment (Tl—O of 2.333(10) Å) in which each 0.4-oxo ligand bridges the central Tl$^{III}$ and three Pd$^{II}$ ions. The twelve Pd$^{II}$ ions all adopt a square-planar coordination geometry and form a distorted cuboctahedron around the central Tl$^{III}$. The resulting TlO$_8$Pd$_{12}$ assembly is surrounded by the 16 acetate ligands, which are bonded to all twelve Pd$^{II}$ ions. Each of the twelve Pd$^{II}$ ions coordinates two carboxyl oxygen atoms from two different acetate ligands, wherein the overall 24 coordination sites of the twelve Pd$^{II}$ ions are occupied by eight bidentate acetate ligands (Pd—O of 1.985(10) Å) and eight monodentate acetate ligands (Pd—O of 2.036(11) Å).

Example 13: $^{13}$C NMR Spectrum of "K—TlPd$_{12}$"

"K—TlPd$_{12}$" crystals were dissolved in H$_2$O/D$_2$0. $^{13}$C NMR spectrum was recorded at room temperature on a 400 MHz JEOL ECX instrument, using 5 mm tube with resonance frequency 100.71 MHz. The chemical shift is reported with respect to the reference Si(CH$_3$)$_4$. The $^{13}$C NMR spectrum is shown in FIG. 8.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

Additionally or alternatively, the invention relates to:

Embodiment 1

A polyoxometalate represented by the formula

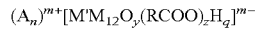

or solvates thereof, wherein
each A independently represents a cation,
n is the number of cations,
each M is independently selected from the group consisting of Pd, Pt, Rh, Ir, Ag and Au, and each M has d$^8$ valence electron configuration,
M' is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg, lanthanide metal, Ga, In, Tl, Ge, Sn, Pb, Sb, and Bi,
each RCOO is a carboxylate-based group, wherein each R is independently selected from the group consisting of a hydrogen atom and a radical which is covalently bonded to the carbon atom of the carboxylate group, wherein each R that is not hydrogen provides a carbon atom for coordination to the carbon atom of the carboxylate group,
y is a number from 8 to 16,
z is a number from 12 to 24,
q is a number from 0 to 8, and
m is a number representing the total positive charge m+ of n cations A and the corresponding negative charge m− of the polyanion [M'M$_{12}$O$_y$(RCOO)$_z$H$_q$].

Embodiment 2

Polyoxometalate according to embodiment 1, wherein all M are the same; preferably wherein all M are Pd or Pt, more preferably wherein all M are Pd.

Embodiment 3

Polyoxometalate according to embodiment 1 or 2, wherein M' is selected from the group consisting of Pd, Pt, Rh, Ir, Ag and Au, and M' has d$^8$ valence electron configuration; preferably wherein M' is selected from the group consisting of Pd, Pt and Au; more preferably wherein M' is selected from the group consisting of Pd and Pt; most preferably wherein M' is Pd.

Embodiment 4

Polyoxometalate according to any one of the preceding embodiments, wherein all M are Pd or Pt, M' is selected from the group consisting of Pd, Pt and Au, and y is 8, preferably wherein q is 0, 2, 4, 6 or 8 and z is 16, more preferably wherein q is 0 and z is 16; in particular all M are Pd, M' is Pd and y is 8; more particularly wherein q is 0 and z is 16.

Embodiment 5

Polyoxometalate according to embodiment 1 or 2, wherein M' is selected from the group consisting of Ga, In, Tl, Ge, Sn, Pb, Sb, and Bi; preferably wherein M' is selected from the group consisting of Ga, In, Tl, Sn, Pb, Sb and Bi; more preferably wherein M' is selected from the group consisting of Ga, In, Tl, Sn and Pb; more preferably wherein M' is selected from the group consisting of Ga, In, Tl and Sn; most preferably wherein M' is In or Tl; in particular all M are Pd, M' is In and y is 8; more particularly wherein q is 0 and z is 16.

Embodiment 6

Polyoxometalate according to any one of the preceding embodiments, wherein
each R is independently selected from the group consisting of a hydrogen atom and a radical which is covalently bonded to the carbon atom of the carboxylate group, wherein
each R that is not hydrogen provides a carbon atom for coordination to the carbon atom of the carboxylate group,
each R that is not hydrogen is a radical that is independently selected from the group consisting of alkyl, alkenyl, alkynyl, aryl, heteroaryl, cycloalkyl, and heterocycloalkyl, preferably an alkyl, more preferably a C$_1$-C$_6$ alkyl, most preferably a C$_1$-C$_4$ alkyl, in particular an alkyl selected from —CH$_3$, —C$_2$H$_5$, -nC$_3$H$_7$, -iC$_3$H$_7$ and -tC$_4$H$_9$.

Embodiment 7

Polyoxometalate according to embodiment 6, wherein the radical is further substituted with one or more moieties X which can be the same or different, and
each moiety X is independently selected from the group consisting of halogens, in particular F, Cl, Br or I, more particularly F or Cl;
—CN, —C(O)OR$^2$, —C(O)R$^2$, —C(O)NR$^2$R$^3$ and —COO$^−$;
—OR$^2$, —O(SO$_2$)R$^2$, —O(SO)R$^2$, —O(SO$_2$)OR$^2$, —O(SO)OR$^2$, —OS(O$_2$)NR$^2$R$^3$, —OS(O)NR$^2$R$^3$, —OPO(OR$^2$)$_2$, —OPO(OR$^2$)OR$^3$, —OPO(R$^2$)OR$^3$, —OC(O)R$^2$, —OC(O)NR$^2$R$^3$ and —OC(O)OR$^2$;
—SO$_3$R$^2$, —SR$^2$, —S(O$_2$)R$^2$, —S(O)R$^2$, —S(O)OR$^2$, —S(O)NR$^2$R$^3$ and —S(O$_2$)NR$^2$R$^3$;
—POR$^2$R$^3$, —P(R$^2$)S(O$_2$)R$^3$, —P(R$^2$)S(O$_2$)PR$^3$R$^4$, —P(R$^2$)S(O$_2$)OR$^3$, —P(R$^2$)S(O)OR$^3$, —P(R$^2$)S(O)PR$^3$R$^4$, —P(R$^2$)S(O)OR$^3$, —P(R$^2$)PO(OR$^3$)$_2$, —P(R$^2$)

PO(OR³)OR⁴, —P(R²)PO(R³)OR⁴, —P(R²)C(O)R³, —P(R²)C(O)OR³ and —P(R²)C(O)PR³R⁴; and —NR²R³, —N(R²)S(O₂)R³, —N(R²)S(O₂)NR³R⁴, —N(R²)S(O₂)OR³, —N(R²)S(O)R³, —N(R²)S(O)NR³R⁴, —N(R²)S(O)OR³, —N(R²)PO(OR³)₂, —N(R²)PO(OR³)OR⁴, —N(R²)PO(R³)OR⁴, —N(R²)C(O)R³, —N(R²)C(O)OR³, —N(R²)C(O)NR³R⁴ and —NO₂;

wherein R², R³ and R⁴ are independently selected from the group consisting of H, alkyl, alkenyl, alkynyl, aryl, heteroaryl, cycloalkyl, and heterocycloalkyl, especially H or $C_1$-$C_6$ alkyl, such as H or $C_1$-$C_4$ alkyl.

Embodiment 8

Polyoxometalate according to any one of the preceding embodiments, wherein, each A is independently selected from the group consisting of Li, Na, K, Rb, Cs, Mg, Ca, Sr, Ba, Sc, Ti, V, Cr, Mn, Fe, Co, Ni, Cu, Zn, Y, Zr, Ru, Rh, Pd, Pt, Ag, Cd, Lu, Hf, Re, Os, Ir, Pt, Au, Hg, La, lanthanide metal, actinide metal, Ga, In, Tl, Ge, Sn, Pb, Sb, Bi, Te, phosphonium, ammonium, guanidinium, tetraalkylammonium, protonated aliphatic amines, protonated aromatic amines or combinations thereof; preferably from the group consisting of Li, K, Na and combinations thereof.

Embodiment 9

Polyoxometalate according to any one of the preceding embodiments, represented by the formula

$(A_n)^{m+}[M'M_{12}O_y(RCOO)_zH_q]^{m-} \cdot wH_2O$ wherein w represents the number of attracted water molecules per polyanion $[M'M_{12}O_y(RCOO)_zH_q]$, and ranges from 1 to 100, preferably from 10 to 60, more preferably from 20 to 50.

Embodiment 10

Polyoxometalate according to any one of the preceding embodiments, wherein the polyoxometalate is in the form of particles, preferably wherein at least 90 wt % of the polyoxometalate particles are in the form of primary particles.

Embodiment 11

Process for the preparation of the polyoxometalate according to any one of embodiments 1 to 10, said process comprising:
(a) reacting at least one source of M and at least one source of M' with at least one RCOO-containing starting material to form a salt of the polyanion $[M'M_{12}O_y(RCOO)_zH_q]$ or a solvate thereof,
(b) optionally adding at least one salt of A to the reaction mixture of step (a) to form a polyoxometalate $(A_n)^{m+}[M'M_{12}O_y(RCOO)_zH_q]^{m-}$ or a solvate thereof, and
(c) recovering the polyoxometalate or solvate thereof.

Embodiment 12

Process according to embodiment 11, wherein in step (a) the concentration of the metal ions originating from the source of M ranges from 0.01 to 1 mole/l, the concentration of the metal ions originating from the sources of M' ranges from 0.001 to 0.5 mole/l, and the concentration of the RCOO-containing starting material ranges from 0.001 to 1 mole/l, with the proviso that the ratio of the molar concentration of the metal ions originating from the source of M to the molar concentration of the metal ions originating from the source of M' is in the range from 1 to 20.

Embodiment 13

Process according to embodiment 11 or 12, wherein in step (a) at least one source of M is used and wherein all M are the same; preferably wherein all M are Pd.

Embodiment 14

Process according to any one of embodiments 11 to 13, wherein water is used as solvent.

Embodiment 15

Process according to embodiment 14, wherein the at least one source of M is a water-soluble salt of $Pt^{II}$ or $Pd^{II}$, preferably platinum chloride, palladium nitrate, palladium sulphate, palladium chloride or palladium acetate, in particular a water-soluble salt of $Pd^{II}$, more preferably palladium nitrate, palladium sulphate, palladium chloride or palladium acetate; the at least one source of M' is a water-soluble salt of $Pt^{II}$ or $Pd^{II}$, preferably platinum chloride, palladium nitrate, palladium sulphate, palladium chloride or palladium acetate, in particular a water-soluble salt of $Pd^{II}$, more preferably palladium nitrate, palladium sulphate, palladium chloride or palladium acetate; and the at least one source of RCOO-containing starting material is a water-soluble carboxylic acid or preferably a salt thereof, in particular HCOOH, H₃CCOOH, H₃C(H₂C)COOH, H₃C(H₂C)₂COOH, H₃C(H₂C)₃COOH, (H₃C)₂(HC)COOH, (H₃C)₃CCOOH, or a salt thereof, most preferably Na(H₃CCOO) or K(H₃CCOO).

Embodiment 16

Process according to embodiment 14, wherein the at least one source of M is a water-soluble salt of $Pt^{II}$ or $Pd^{II}$, preferably platinum chloride, palladium nitrate, palladium sulphate, palladium chloride or palladium acetate, in particular a water-soluble salt of $Pd^{II}$, more preferably palladium nitrate, palladium sulphate, palladium chloride or palladium acetate; the at least one source of M' is a water-soluble gallium, thallium, indium or tin salt, preferably indium(III) nitrate or tin(IV) chloride, in particular a water-soluble indium salt, more preferably indium(III) nitrate; and the at least one source of RCOO-containing starting material is a water-soluble carboxylic acid RCOOH or preferably a salt thereof, in particular HCOOH, H₃CCOOH, H₃C(H₂C)COOH, H₃C(H₂C)₂COOH, H₃C(H₂C)₃COOH, (H₃C)₂(HC)COOH, (H₃C)₃CCOOH, or a salt thereof, most preferably Na(H₃CCOO) or K(H₃CCOO).

Embodiment 17

Process according to any one of embodiments 11 to 16, wherein step (a) is carried out in an aqueous solution, and the pH of the aqueous solution ranges from 4 to 12, preferably from 5 to 10, and most preferred from 6 to 9.

Embodiment 18

Process according to embodiment 17, wherein in step (a) the at least one source of M, the at least one source of M', and the at least one source of RCOO-containing starting material are dissolved in a solution of a buffer, preferably a 0.1 to 1.0 mole/l solution of a buffer, in particular a 0.25 to 0.75 mole/l solution of a buffer, and most preferred a 0.50 mole/l solution of a buffer; wherein preferably the buffer is a carboxylate-based buffer comprising the at least one source of RCOO-containing starting material and most preferably said RCOO-containing buffer is derived from Na(H$_3$CCOO) or K(H$_3$CCOO), in particular K(H$_3$CCOO).

Embodiment 19

Process according to any one of embodiments 11 to 18, wherein in step (a) the reaction mixture is heated to a temperature of from 20° C. to 100° C., preferably from 50° C. to 80° C.

Embodiment 20

Supported polyoxometalate comprising polyoxometalate according to any one of embodiments 1 to 10 or prepared according to any one of embodiments 11 to 19, on a solid support.

Embodiment 21

Supported polyoxometalate according to embodiment 20, wherein the solid support is selected from polymers, graphite, carbon nanotubes, electrode surfaces, aluminum oxide and aerogels of aluminum oxide and magnesium oxide, titanium oxide, zirconium oxide, cerium oxide, silicon dioxide, silicates, active carbon, mesoporous silica, zeolites, aluminophosphates (ALPOs), silicoaluminophosphates (SAPOs), metal organic frameworks (MOFs), zeolitic imidazolate frameworks (ZIFs), periodic mesoporous organosilicas (PMOs), and mixtures thereof.

Embodiment 22

Process for the preparation of supported polyoxometalate according to embodiment 20 or 21, comprising the step of contacting polyoxometalate according to any one of embodiments 1 to 10 or prepared according to any one of embodiments 11 to 19, with a solid support.

Embodiment 23

Metal cluster of the formula $$[M'M^0{}_{12}]$$

wherein
each $M^0$ is independently selected from the group consisting of $Pd^0$, $Pt^0$, $Rh^0$, $Ir^0$, $Ag^0$, and $Au^0$, preferably $Pd^0$ and $Pt^0$, most preferably $Pd^0$; in particular wherein all $M^0$ are the same, preferably wherein all $M^0$ are Pd, and
M' is selected from the group consisting of Li, Na, K, Mg, Ca, Sr, Sc, Ti, V, Cr, Mn, Fe, Co, Ni, Cu, Zn, Y, Zr, Ru, Rh, Pd, Ag, Cd, Lu, Hf, Re, Os, Ir, Pt, Au, Hg, lanthanide metal, Ga, In, Tl, Ge, Sn, Pb, Sb and Bi, and the oxidation state of M' is 0 or greater than 0; preferably M' is Pd or Pt or is selected from the group consisting of Ga, In, Tl, Ge, Sn, Pb, Sb, and Bi; more preferably M' is Pd or is selected from the group consisting of Ga, In, Tl and Sn; most preferably $Pd^0$ or $In^0$ or $Tl^0$, in particular $In^0$.

Embodiment 24

Metal cluster of the formula $$[M'M^0{}_{12}]$$

obtainable by reduction of the polyoxometalate of any one of embodiments 1 to 10 or prepared 30 according to any one of embodiments 11 to 19.

Embodiment 25

Metal cluster according to embodiment 23 or 24, wherein the metal cluster is in the form of particles, preferably wherein at least 90 wt % of the metal cluster particles are in the form of primary particles.

Embodiment 26

Metal cluster according to any one of embodiments 23 to 25, wherein the metal cluster is dispersed in a liquid carrier medium thereby forming a dispersion of metal cluster in said liquid carrier medium; and wherein preferably a dispersing agent is present to prevent agglomeration of the primary particles of metal cluster, and in particular the dispersing agent forms micelles containing one primary particle of metal cluster per micelle.

Embodiment 27

Metal cluster according to any one of embodiments 23 to 25, wherein the metal cluster is immobilized on a solid support thereby forming supported metal cluster.

Embodiment 28

Supported metal cluster according to embodiment 27, wherein the solid support is selected from polymers, graphite, carbon nanotubes, electrode surfaces, aluminum oxide and aerogels of aluminum oxide and magnesium oxide, titanium oxide, zirconium oxide, cerium oxide, silicon dioxide, silicates, active carbon, mesoporous silica, zeolites, aluminophosphates (ALPOs), silicoaluminophosphates (SAPOs), metal organic frameworks (MOFs), zeolitic imidazolate frameworks (ZIFs), periodic mesoporous organosilicas (PMOs), and mixtures thereof.

Embodiment 29

Process for the preparation of the dispersion of metal cluster of embodiment 26, said process comprising the steps of
(a) dissolving the polyoxometalate of any one of embodiments 1 to 10 or prepared according to any one of embodiments 11 to 19, in a liquid carrier medium,
(b) optionally providing additive means to prevent agglomeration of the metal cluster to be prepared, and
(c) subjecting the dissolved polyoxometalate to chemical or electrochemical reducing conditions sufficient to at least partially reduce said polyoxometalate into corresponding metal cluster.

Embodiment 30

Process for the preparation of the supported metal clusters of embodiment 27 or 28, comprising the steps of
(a) contacting the dispersion of metal cluster of embodiment 26 or prepared according to embodiment 29 with a solid support, thereby immobilizing at least part of the dispersed metal cluster onto the support; and
(b) optionally isolating the supported metal cluster.

Embodiment 31

Process for the preparation of the supported metal clusters of embodiment 27 or 28, comprising the steps of
(a) subjecting the supported polyoxometalate of embodiment 20 or 21 or prepared according to embodiment 22 to chemical or electrochemical reducing conditions sufficient to at least partially reduce said polyoxometalate into corresponding metal cluster; and
(b) optionally isolating the supported metal cluster.

Embodiment 32

Process according to any one of embodiments 29 or 31, wherein the chemical reducing conditions comprise the use of a reducing agent selected from organic and inorganic materials which are oxidizable by $Pd^{II}$, $Pt^{II}$, Rh, Ir, $Ag^{I}$ and $Ag^{III}$, and $Au^{I}$ and $Au^{III}$.

Embodiment 33

Process for the homogeneous or heterogeneous reductive conversion of organic substrate comprising contacting said organic substrate under addition of hydrogen with the polyoxometalate of any one of embodiments 1 to 10 or prepared according to any one of embodiments 11 to 19, and/or with the supported polyoxometalate of embodiment 20 or 21 or prepared according to embodiment 22, and/or with the metal cluster of any one of embodiments 23 to 25, and/or with the dispersion of metal cluster of embodiment 26 or prepared according to embodiment 29 or 32, and/or with the supported metal cluster of embodiment 27 or 28 or prepared according to any one of embodiments 30 to 32.

Embodiment 34

Process according to embodiment 33, comprising:
(a) contacting a first organic substrate under addition of hydrogen with one or more optionally supported polyoxometalates and/or one or more supported metal clusters,
(b) recovering the one or more optionally supported polyoxometalates and/or the one or more supported metal clusters;
(c) contacting the one or more optionally supported polyoxometalates and/or the one or more supported metal clusters with a solvent at a temperature of 50° C. or more, and/or hydrogen stripping the one or more optionally supported polyoxometalates and/or the one or more supported metal clusters at elevated temperature, and/or calcining the one or more optionally supported polyoxometalates and/or the one or more supported metal clusters at elevated temperature under an oxygen containing gas, e.g. air, or under an inert gas, e.g. nitrogen or argon, to obtain recycled one or more optionally supported polyoxometalates and/or one or more supported metal clusters;
(d) contacting the recycled one or more optionally supported polyoxometalates and/or the one or more supported metal clusters under addition of hydrogen with a second organic substrate which may be the same as or different from the first organic substrate; and
(e) optionally repeating steps (b) to (d).

The invention claimed is:
1. Polyoxometalate represented by the formula

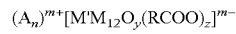

or solvates thereof, wherein
each A independently represents a cation and is selected from the group consisting of tetraalkylammonium, Li, K, Na and combinations thereof,
n is the number of cations with n ranging from 1 to 45,
all M are the same and are selected from the group consisting of Pd and Pt, and each M has $d^8$ valence electron configuration,
M' is selected from the group consisting of Ga, In, Tl, Sn, and Pb,
each RCOO is a carboxylate-based group, wherein each R is independently selected from the group consisting of a hydrogen atom and alkyl groups containing 1 to 6 carbon atoms, optionally substituted with F or Cl,
y is 8,
z is 16, and
m is a number representing a total positive charge of n cations A and a corresponding negative charge of polyanion $[M'M_{12}O_y(RCOO)_z]$, and m ranges from 1 to 45.

2. The polyoxometalate according to claim 1, wherein all M are Pd, and M' is selected from the group consisting of Ga, In, Tl and Sn.

3. The polyoxometalate according to claim 1, wherein R is selected from H and alkyl groups containing 1 to 4 carbon atoms.

4. Polyoxometalato The polyoxometalate according to claim 1, wherein the polyoxometalate is in the form of particles.

5. The polyoxometalate according to claim 1, wherein m is 3, 5, 6, 9, 10, 12, 14, 22, 30 or 35.

6. The polyoxometalate according to claim 1, wherein m is 5 or 6.

7. The polyoxometalate according to claim 1, wherein n is 3, 5, 6, 10, 12, 14, 22, or 30.

8. The polyoxometalate according to claim 1, wherein n is 5 or 6.

9. Process for the preparation of the polyoxometalate according to claim 1, said process comprising:
(a) reacting at least one source of M and at least one source of M' with at least one RCOO-containing starting material to form a salt of the polyanion $[M'M_{12}O_y(RCOO)_z]$ or a solvate thereof,
(b) adding at least one salt of A to the reaction mixture of step (a) to form a polyoxometalate $(A_n)^{m+}[M'M_{12}O_y(RCOO)_z]^{m-}$ or a solvate thereof, and
(c) recovering the polyoxometalate or solvate thereof,
wherein
water is used as solvent,
the at least one source of M is a water-soluble salt of $Pt^{II}$ or $Pd^{II}$,
the at least one source of M' is a water-soluble gallium, thallium, indium, tin or lead salt,
the at least one RCOO-containing starting material is a water-soluble carboxylic acid RCOOH or a salt thereof,
the pH of the aqueous solution in step (a) ranges from 2 to 14, and
the reaction mixture in step (a) is heated to a temperature of from 20° C. to 100° C.

10. The process according to claim 9, wherein the at least one source of M is platinum chloride, palladium nitrate, palladium sulphate, palladium chloride or palladium acetate, the at least one source of M' is a chloride, acetate, bromide or nitrate salt of gallium, thallium, indium or tin, or chloride or acetate salt of lead, and the at least one source of RCOO-containing starting material is HCOOH, H$_3$CCOOH, H$_3$C(H$_2$C)COOH, H$_3$C(H$_2$C)$_2$COOH, H$_3$C(H$_2$C)$_3$COOH, (H$_3$C)$_2$(HC)COOH, (H$_3$C)$_3$CCOOH, or a salt thereof.

11. A supported polyoxometalate comprising the polyoxometalate according to claim 1, on a solid support.

12. Process for the homogeneous or heterogeneous reductive conversion of organic substrate comprising contacting said organic substrate under addition of hydrogen with the polyoxometalate of claim 1.

* * * * *